United States Patent
Shin et al.

(10) Patent No.: US 9,905,776 B2
(45) Date of Patent: *Feb. 27, 2018

(54) PYRENE-BASED COMPOUND AND ORGANIC LIGHT-EMITTING DIODE COMPRISING THE SAME

(71) Applicant: SAMSUNG DISPLAY CO., LTD., Yongin, Gyeonggi-do (KR)

(72) Inventors: Dong-Woo Shin, Yongin (KR); O-Hyun Kwon, Yongin (KR); Seul-Ong Kim, Yongin (KR); Mie-Hwa Park, Yongin (KR); Sung-Wook Kim, Yongin (KR)

(73) Assignee: Samsung Display Co., Ltd., Yongin-si (KR)

(*) Notice: Subject to any disclaimer, the term of this patent is extended or adjusted under 35 U.S.C. 154(b) by 647 days.

This patent is subject to a terminal disclaimer.

(21) Appl. No.: 14/080,627

(22) Filed: Nov. 14, 2013

(65) Prior Publication Data

US 2014/0183468 A1 Jul. 3, 2014

(30) Foreign Application Priority Data

Dec. 27, 2012 (KR) .................. 10-2012-0155319

(51) Int. Cl.
*H01L 51/00* (2006.01)
*C07C 211/61* (2006.01)
(Continued)

(52) U.S. Cl.
CPC .......... *H01L 51/006* (2013.01); *C07B 59/001* (2013.01); *C07C 211/61* (2013.01);
(Continued)

(58) Field of Classification Search
None
See application file for complete search history.

(56) References Cited

U.S. PATENT DOCUMENTS

| | | | |
|---|---|---|---|
| 5,153,073 A | 10/1992 | Ohnuma et al. | |
| 8,686,406 B2 * | 4/2014 | Shin ................. | H01L 51/006 257/103 |

(Continued)

FOREIGN PATENT DOCUMENTS

| KR | 10-2010-0075101 A | 7/2010 |
|---|---|---|
| KR | 10-2011-0081698 A | 7/2011 |

*Primary Examiner* — Francisco W Tschen
(74) *Attorney, Agent, or Firm* — H.C. Park & Associates, PLC

(57) ABSTRACT

A pyrene-based compound and an organic light-emitting diode including the pyrene-based compound are provided. The pyrene-based compound of Formula 1 above may emit blue light having high color purity. For example, an organic light-emitting diode including the pyrene-based compounds of the invention may emit blue light having a y coordinate with a color purity of 0.1 or less, for example, a color purity of 0.09 or less, which is near to the NTSC or sRGB specification. A thin film including the pyrene-based compounds of the invention may be highly amorphous, and thus may have improved electrical stability. Accordingly, an organic light-emitting diode including the pyrene-based compounds of the invention may have improved lifetime characteristics.

16 Claims, 1 Drawing Sheet

(51) Int. Cl.
*C07B 59/00* (2006.01)
*C09K 11/06* (2006.01)
*H01L 51/50* (2006.01)

(52) U.S. Cl.
CPC .......... C09K 11/06 (2013.01); *C07C 2603/50* (2017.05); *C09K 2211/1014* (2013.01); *H01L 51/0054* (2013.01); *H01L 51/0058* (2013.01); *H01L 51/5012* (2013.01); *H01L 2251/308* (2013.01)

(56) References Cited

U.S. PATENT DOCUMENTS

| | | | |
|---|---|---|---|
| 2003/0044643 A1* | 3/2003 | Arakane | C09K 11/06 428/690 |
| 2010/0052526 A1* | 3/2010 | Je | C07C 211/61 313/504 |
| 2011/0193064 A1* | 8/2011 | Funahashi | C07C 211/61 257/40 |
| 2013/0228752 A1* | 9/2013 | Shin | H01L 51/006 257/40 |

* cited by examiner

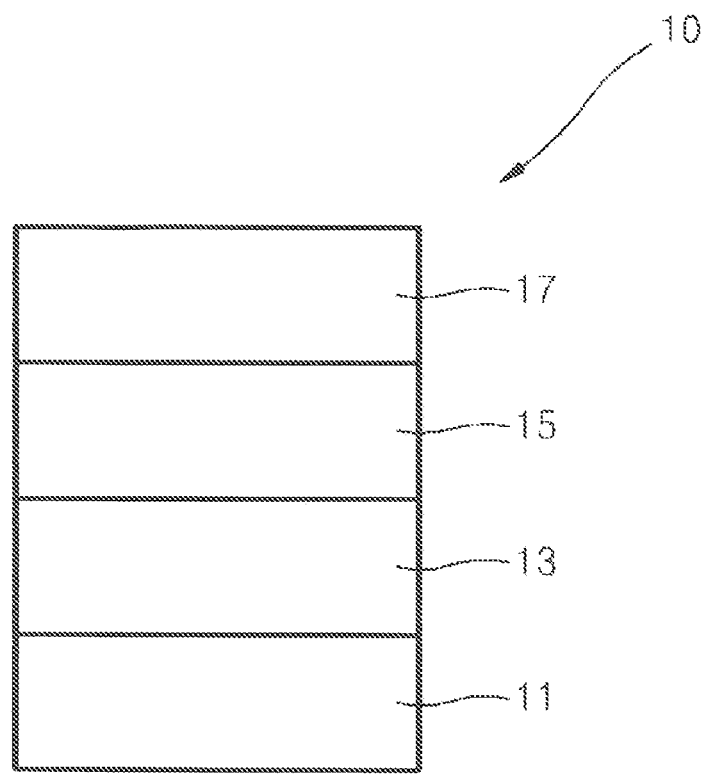

PYRENE-BASED COMPOUND AND ORGANIC LIGHT-EMITTING DIODE COMPRISING THE SAME

CLAIM OF PRIORITY

This application makes reference to, incorporates the same herein, and claims all benefits accruing under 35 U.S.C. § 119 from an application for PYRENE-BASED COMPOUND AND ORGANIC LIGHT-EMITTING DIODE COMPRISING THE SAME, earlier filed in the Korean Intellectual Property Office on Dec. 27, 2012 and there duly assigned Serial No. 10-2012-0155319.

BACKGROUND OF THE INVENTION

Field of the Invention

One or more embodiments of the present invention relate to a compound for organic light-emitting diodes, and an organic light-emitting diode including the compound.

Description of the Related Art

Organic light-emitting diodes (OLEDs), which are self-emitting diodes, have advantages such as wide viewing angles, excellent contrast, quick response, high brightness, excellent driving voltage characteristics, and can provide multicolored images.

An exemplary organic light emitting diode has a structure that includes an anode, a hole transport layer (HTL), an emission layer, an electron transport layer (ETL) and a cathode that are sequentially formed on a substrate. The HTL, the EML, and the ETL are normally organic thin films formed of organic compounds.

An operating principle of an OLED having the above-described structure is as follows.

Holes injected from the anode move to the EML via the HTL, while electrons injected from the cathode move to the EML via the ETL. The holes and electrons recombine in the EML to generate excitons. When the excitons drop from an excited state to a ground state, light is emitted.

SUMMARY OF THE INVENTION

One or more embodiments of the present invention include a pyrene-based compound having a novel structure, and an organic light-emitting diode including the pyrene-based compound.

Additional aspects will be set forth in part in the description which follows and, in part, will be apparent from the description, or may be learned by practice of the presented embodiments.

According to one or more embodiments of the present invention, there is provided a pyrene-based compound represented by Formula 1 below:

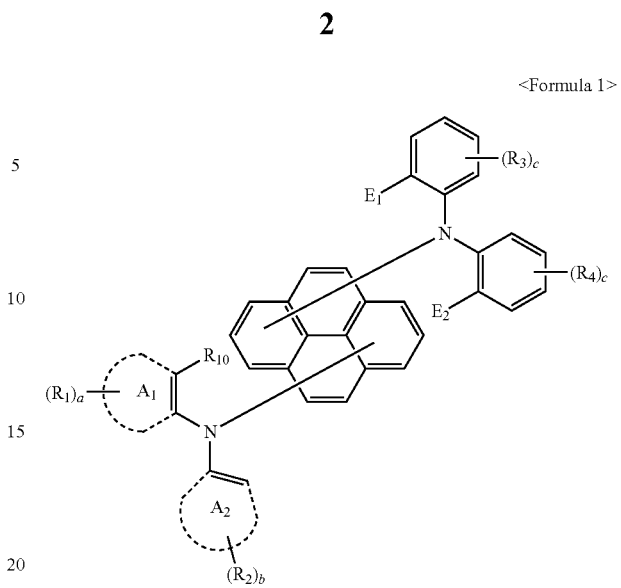

<Formula 1> wherein, in Formula 1, $E_1$ and $E_2$ are each independently an electron withdrawing group selected from —F; —CN; and a $C_1$-$C_{60}$ alkyl group substituted with at least one —F;

a $A_1$ ring and a $A_2$ ring are each independently a $C_6$-$C_{30}$ aromatic ring;

$R_{10}$ is selected from a hydrogen atom, a deuterium atom, a hydroxyl group, a carboxyl group or a salt thereof, a sulfonic acid group or a salt thereof, a phosphoric acid group or a salt thereof, a $C_1$-$C_{60}$ alkyl group, a $C_1$-$C_{60}$ alkoxy group, and a $C_6$-$C_{60}$ aryl group;

$R_1$ to $R_4$ are each independently at least one selected from, a hydrogen atom, a deuterium atom, —F, —Cl, —Br, —I, —CN, a hydroxy group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkoxy group, a $C_2$-$C_{60}$ alkenyl group, and a $C_2$-$C_{60}$ alkynyl group, a $C_1$-$C_{60}$ alkyl group, a $C_1$-$C_{60}$ alkoxy group, a $C_2$-$C_{60}$ alkenyl group, and a $C_2$-$C_{60}$ alkynyl group, substituted with at last one of a deuterium atom, —F, —Cl, —Br, —I, —CN, a hydroxyl group, a nitro group, an amino group, an amidino group, a hydrazine, a hydrazone, a carboxyl group or a salt thereof, a sulfonic acid group or a salt thereof, and a phosphoric acid group or a salt thereof, a $C_3$-$C_{10}$ cycloalkyl group, a $C_3$-$C_{10}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthio group, a $C_3$-$C_{10}$ cycloalkyl group, a $C_3$-$C_{10}$ cycloalkenyl group $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthio group, substituted with at least one of a deuterium atom, —F, —Cl, —Br, —I, —CN, a hydroxyl group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, a $C_6$-$C_{60}$ aryl group substituted with at least one —F, and a $C_2$-$C_{60}$ heteroaryl group, and —N($Q_1$)($Q_2$) and —Si($Q_3$)($Q_4$)($Q_5$), where $Q_1$ to $Q_5$ are each independently selected from a $C_1$-$C_{60}$ alkyl group, a $C_1$-$C_{60}$alkoxy group, a $C_2$-$C_{60}$ alkenyl group, a $C_2$-$C_{60}$ alkynyl group, a $C_3$-$C_{60}$cycloalkyl group, a $C_3$-$C_{60}$cycloalkenyl group, a $C_6$-$C_{60}$ aryl group, a $C_2$-$C_{60}$heteroaryl group, a $C_6$-$C_{60}$ aralkyl group, a $C_6$-$C_{60}$ aryloxy group, and a $C_6$-$C_{60}$ arylthio group, and a to d are each independently an integer from 1 to 4.

According to one or more embodiments of the present invention, an organic light-emitting diode includes: a first electrode; a second electrode disposed opposite to the first electrode; and an organic layer disposed between the first electrode and the second electrode and comprising an emission layer, the organic layer comprising at least one of the pyrene-based compounds of Formula 1 above.

BRIEF DESCRIPTION OF THE DRAWING

A more complete appreciation of the invention and many of the attendant advantages thereof will be readily apparent as the same becomes better understood by reference to the following detailed description when considered in conjunction with the accompanying drawings in which like reference symbols indicate the same or similar components, wherein:

FIG. 1 is a schematic view of a structure of an organic light-emitting diode according to an embodiment of the present invention;

DETAILED DESCRIPTION OF THE INVENTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

According to an embodiment of the present invention, there is provided a pyrene-based compound represented by Formula 1 below:

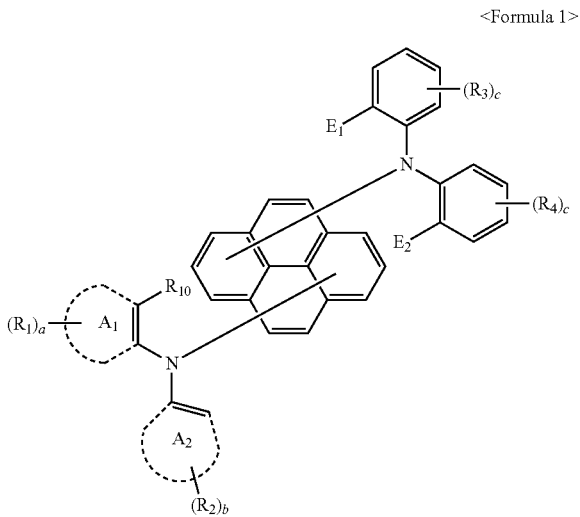

<Formula 1>

In Formula 1, $E_1$ and $E_2$ may be each independently an electron withdrawing group selected from —F; —CN; and a $C_1$-$C_{60}$ alkyl group substituted with at least one —F. For example, $E_1$ and $E_2$ in Formula 1 may both be —F.

In Formula 1, a $A_1$ ring and a $A_2$ ring may be each independently a $C_6$-$C_{30}$ aromatic ring. In some embodiments, the $A_1$ ring and the $A_2$ may be each independently a benzene ring, a naphthalene ring, an anthracene ring, a fluorene ring, a pyrene ring, a chrysene ring, or a phenanthrene ring. For example, the $A_1$ ring and the $A_2$ ring may be each independently a benzene ring or a naphthalene ring.

In Formula 1, $R_{10}$ may be a hydrogen atom, a deuterium atom, a hydroxyl group, a carboxyl group or a salt thereof, a sulfonic acid group or a salt thereof, a phosphoric acid group or a salt thereof, a $C_1$-$C_{60}$ alkyl group, a $C_1$-$C_{60}$ alkoxy group, or a $C_6$-$C_{60}$ aryl group. In some embodiments, $R_{10}$ may be a hydrogen atom, a deuterium atom, a hydroxyl group, a carboxyl group or a salt thereof, a sulfonic acid group or a salt thereof, a phosphoric acid group or a salt thereof, a $C_1$-$C_{10}$ an alkyl group, a phenyl group, a naphthyl group, or an anthryl group. For example, $R_{10}$ may be a hydrogen atom. However, embodiments of the present invention are not limited thereto.

In Formula 1, $R_1$ to $R_4$ may be each independently at least one selected from, a hydrogen atom, a deuterium atom, —F, —Cl, —Br, —I, —CN, a hydroxy group, a nitro group; an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkoxy group, a $C_2$-$C_{60}$ alkenyl group, and a $C_2$-$C_{60}$ alkynyl group;

a $C_1$-$C_{60}$alkyl group, a $C_1$-$C_{60}$ alkoxy group, a $C_2$-$C_{60}$ alkenyl group, and a $C_2$-$C_{60}$ alkynyl group, substituted with at last one of a deuterium atom, —F, —Cl, —Br, —I, —CN, a hydroxyl group, a nitro group, an amino group, an amidino group, a hydrazine, a hydrazone, a carboxyl group or a salt thereof, a sulfonic acid group or a salt thereof, and a phosphoric acid group or a salt thereof;

a $C_3$-$C_{10}$ cycloalkyl group, a $C_3$-$C_{10}$ cycloalkenyl group, a $C_6$-$C_{60}$ aryl group, a $C_2$-$C_{60}$ heteroaryl group, a $C_6$-$C_{60}$aralkyl group, a $C_6$-$C_{60}$ aryloxy group, and a $C_6$-$C_{60}$ arylthio group;

a $C_3$-$C_{10}$ cycloalkyl group, a $C_3$-$C_{10}$ cycloalkenyl group $C_6$-$C_{60}$ aryl group, a $C_2$-$C_{60}$heteroaryl group, a $C_6$-$C_{60}$ aralkyl group, a $C_6$-$C_{60}$ aryloxy group, and a $C_6$-$C_{60}$ arylthio group, substituted with at least one of a deuterium atom, —F, —Cl, —Br, —I, —CN, a hydroxyl group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$aryl group, a $C_6$-$C_{60}$ aryl group substituted with at least one —F, and a $C_2$-$C_{60}$heteroaryl group; and —N($Q_1$)($Q_2$) and —Si($Q_3$)($Q_4$)($Q_5$), where $Q_1$ to $Q_5$ are each independently one of a $C_1$-$C_{60}$ alkyl group, a $C_1$-$C_{60}$alkoxy group, a $C_2$-$C_{60}$ alkenyl group, a $C_2$-$C_{60}$ alkynyl group, a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$aryloxy group, and a $C_6$-$C_{60}$ arylthio group.

In some embodiments, $R_1$ to $R_4$ may be each independently, not limited to, one selected from, a hydrogen atom, a deuterium atom, —F, —Cl, —Br, —I, —CN, a hydroxy group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$alkyl group, and a $C_1$-$C_{10}$alkoxy group;

a $C_1$-$C_{10}$alkyl group, and a $C_1$-$C_{10}$alkoxy group, substituted with at least one of a deuterium atom, —F, —Cl, —Br, —I, —CN, a hydroxyl group, a nitro group, an amino group, an amidino group, a hydrazine, a hydrazone, a carboxyl group or a salt thereof, a sulfonic acid group or a salt thereof, and a phosphoric acid group or a salt thereof;

a phenyl group, a naphthyl group, an anthryl group, a pyrenyl group, a phenanthrenyl group, a fluorenyl group, a spiro-fluorenyl group, a dibenzofuranyl group, and a dibenzothiophenyl group; and a phenyl group, a naphthyl group, an anthryl group, a pyrenyl group, a phenanthrenyl group, a fluorenyl group, a spiro-fluorenyl group, a dibenzofuranyl group, and a dibenzothiophenyl group, substituted with at least one of a deuterium atom, —F, —Cl, —Br, —I, —CN, a hydroxyl group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$alkyl group substituted with at least one —F, a $C_1$-$C_{10}$alkoxy group, a $C_1$-$C_{10}$alkoxy group substituted with at least one —F, a phenyl group, a naphthyl group, and an anthryl group.

$R_{10}$ and $R_1$ are substituent groups of the $A_1$ ring of Formula 1 above, and $R_2$ is a substituent group of the $A_2$ ring of Formula 1 above. When $R_{10}$ and $R_1$ both are hydrogen atoms, the $A_1$ ring has no substituent group. When $R_2$ is a hydrogen atom, the $A_2$ ring has no substituent group.

$R_1$ may be substituted at any site of the $A_1$ ring except for the site with $R_{10}$. $R_2$ may be substituted at any site of the $A_2$ ring.

In Formula 1 above, a to d are each independently an integer from 1 to 4. In Formula 1, a indicates number of $R_1$s. When a is 2 or greater, the at least two $R_1$s may be identical to or differ from each other. In Formula 1, b indicates number of $R_2$s. When b is 2 or greater, the at least two $R_2$s may be identical to or differ from each other. In Formula 1, c indicates number of $R_3$s. When c is 2 or greater, the at least two $R_3$s may be identical to or differ from each other. In Formula 1, d indicates number of $R_4$s. When d is 2 or greater, the at least two $R_4$s may be identical to or differ from each other.

In some embodiments, in Formula 1, a first diarylamino group represented by

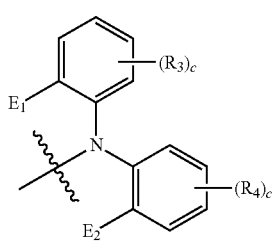

may be selected from, not limited to, the groups represented by the following formulae:

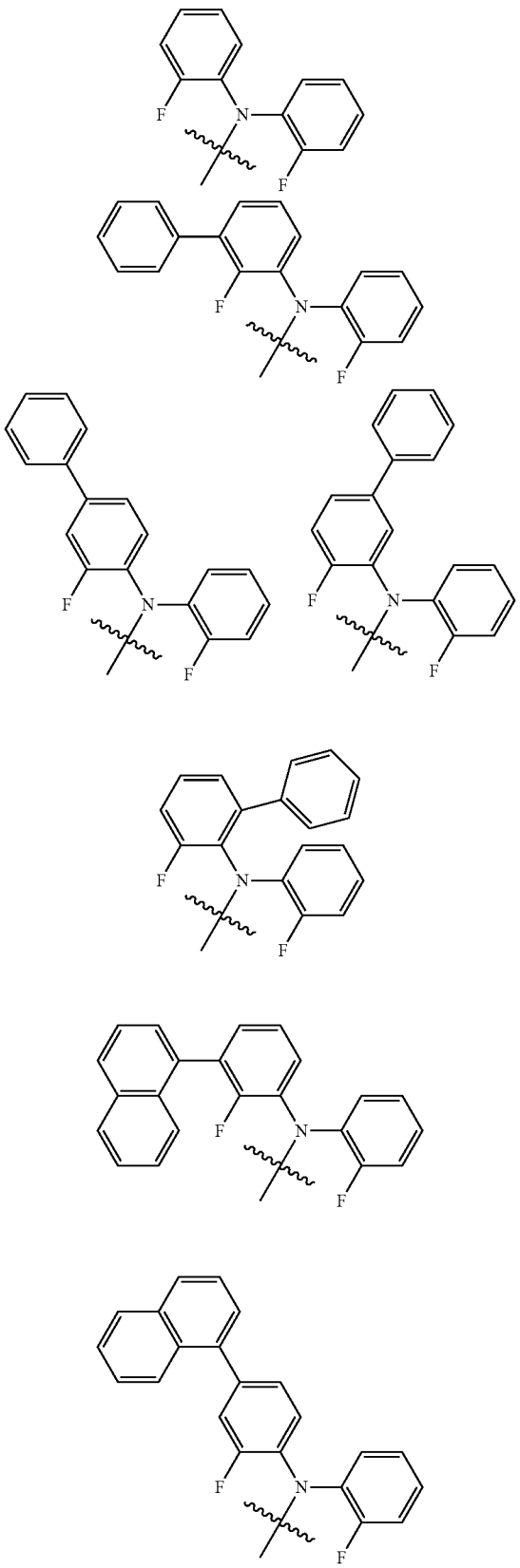

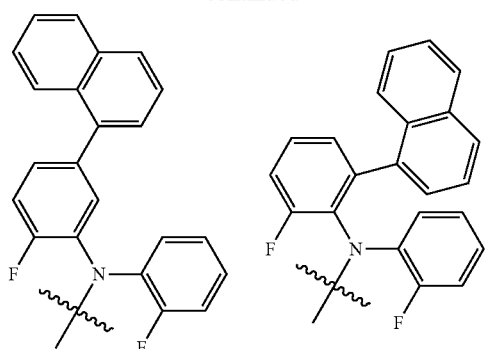
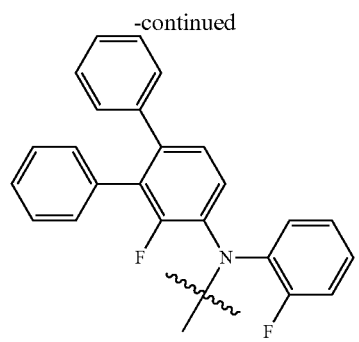
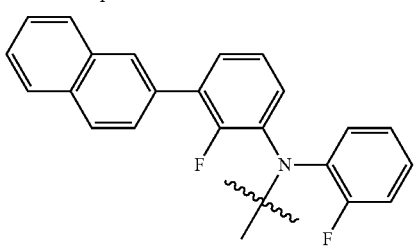
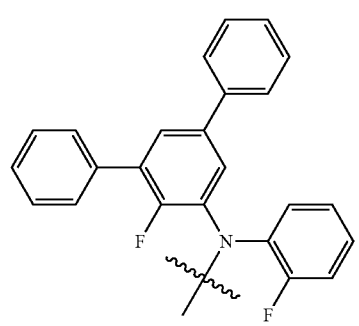
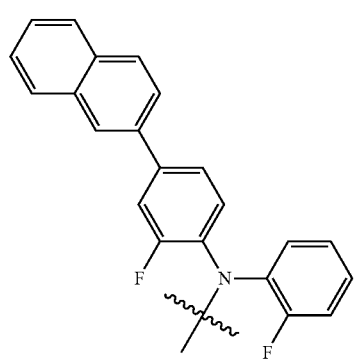
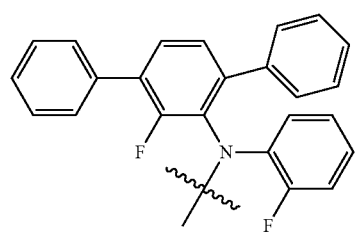
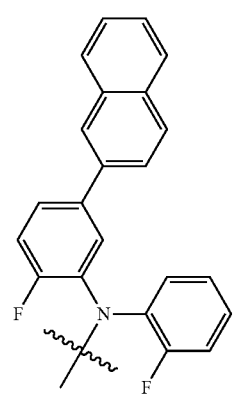
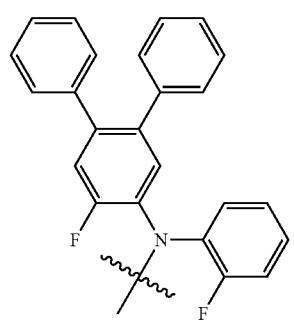
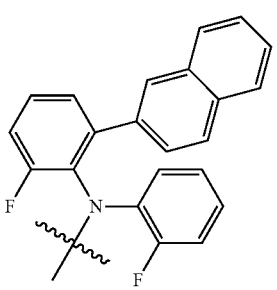
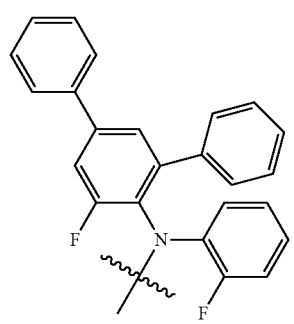

-continued
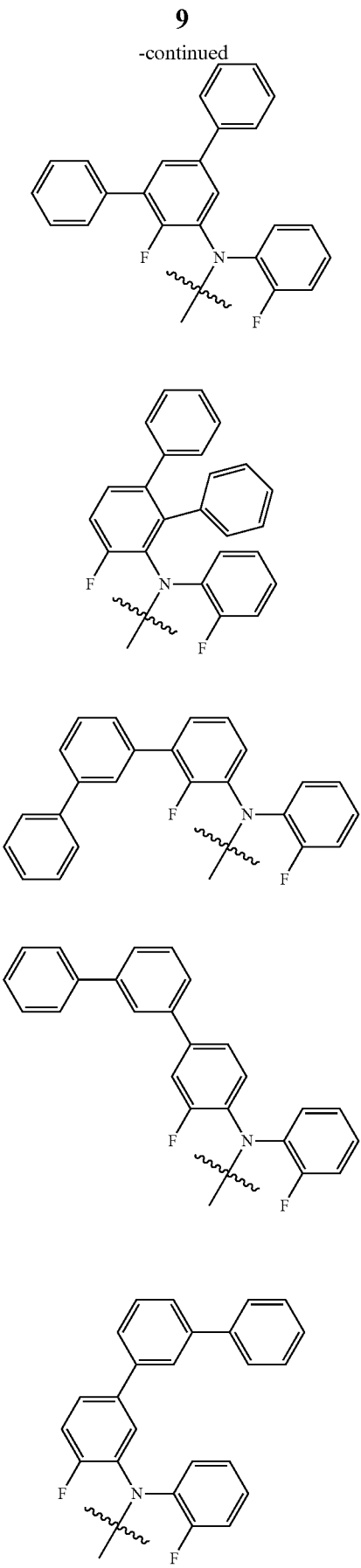
-continued
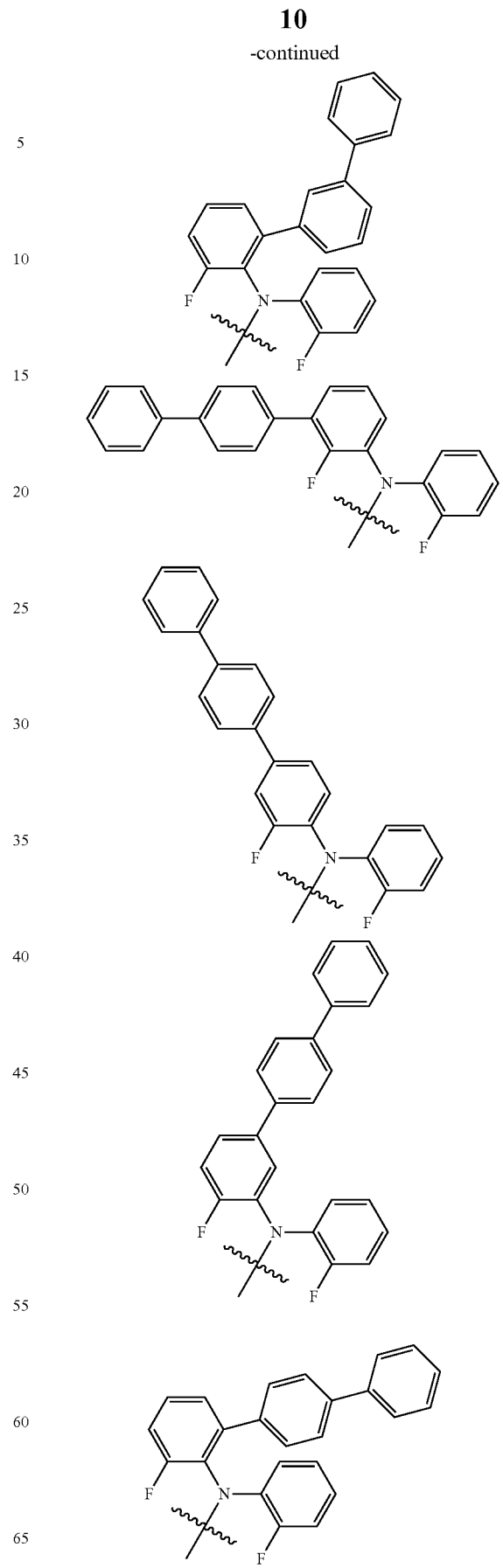

-continued
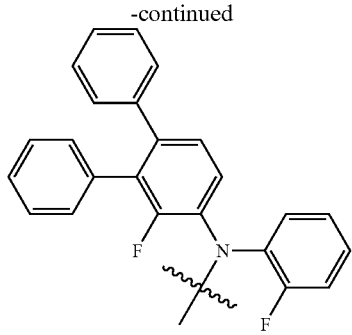
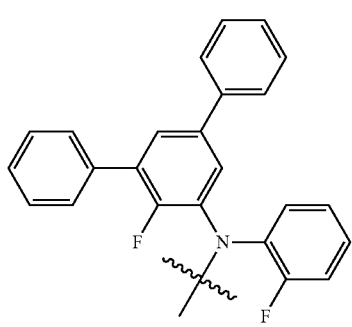
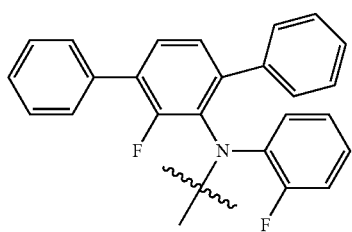
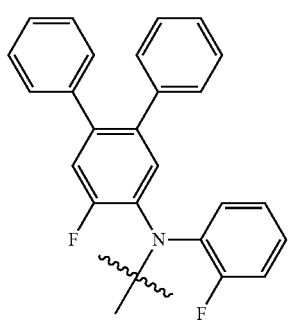
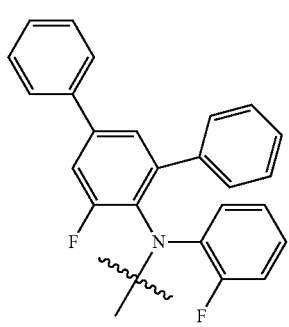
-continued
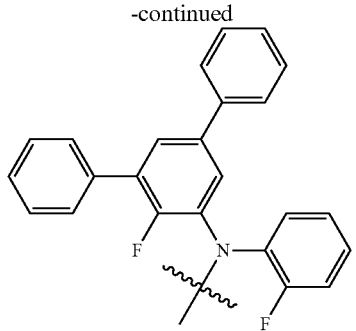
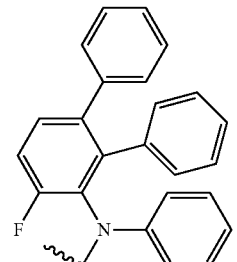
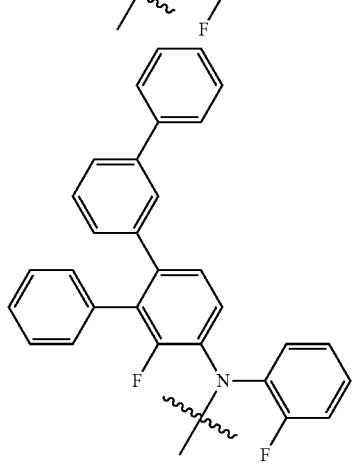
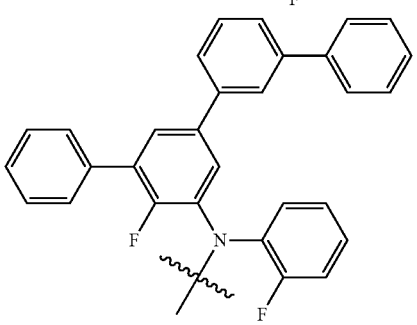
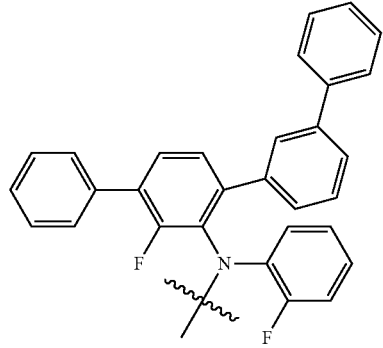

-continued
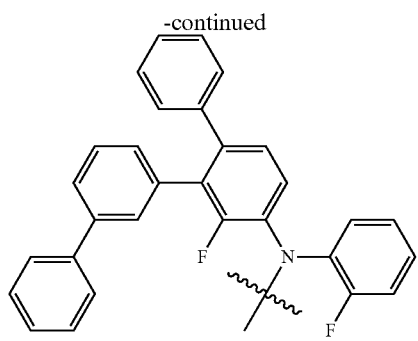
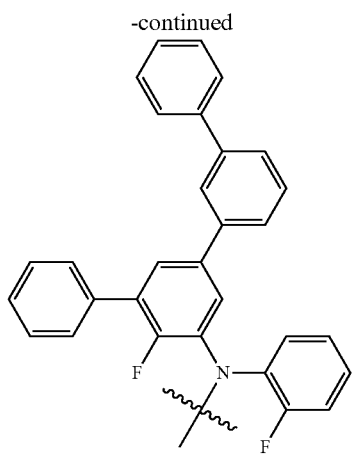
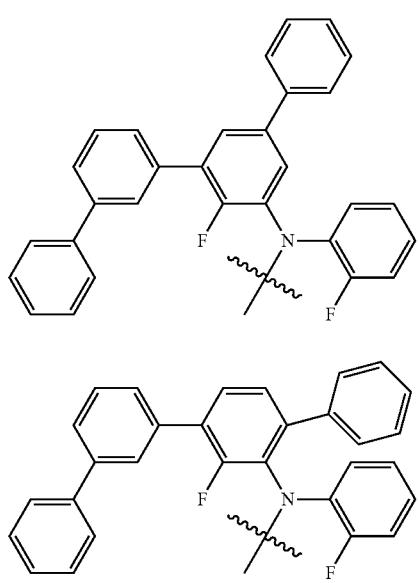
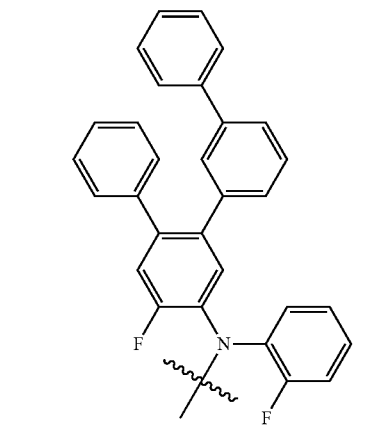
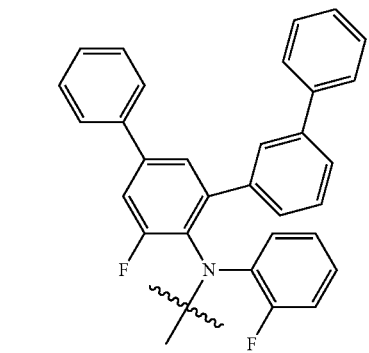

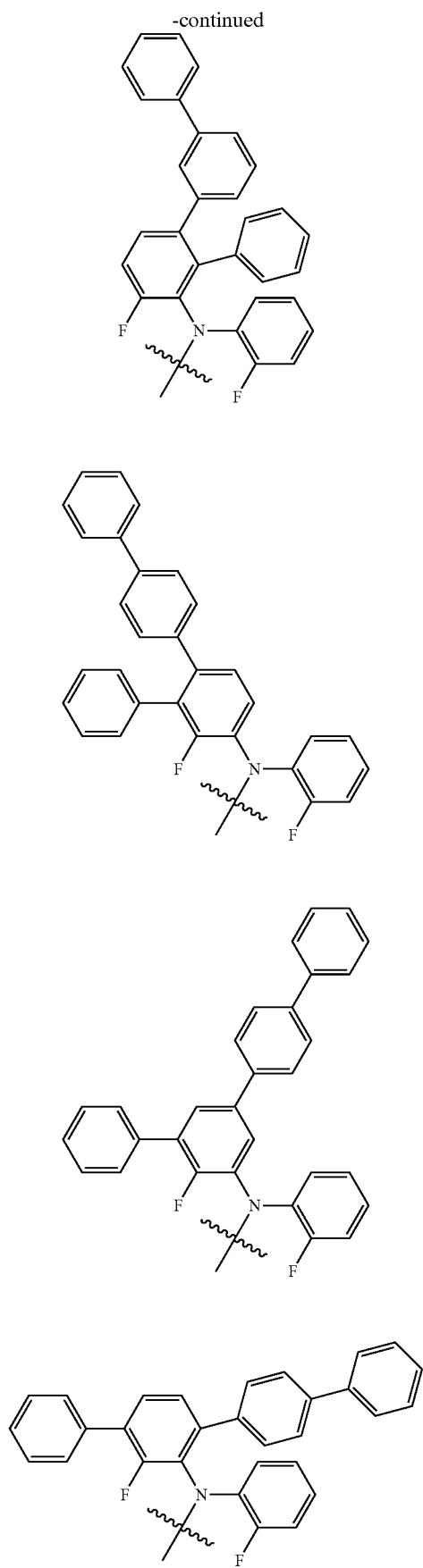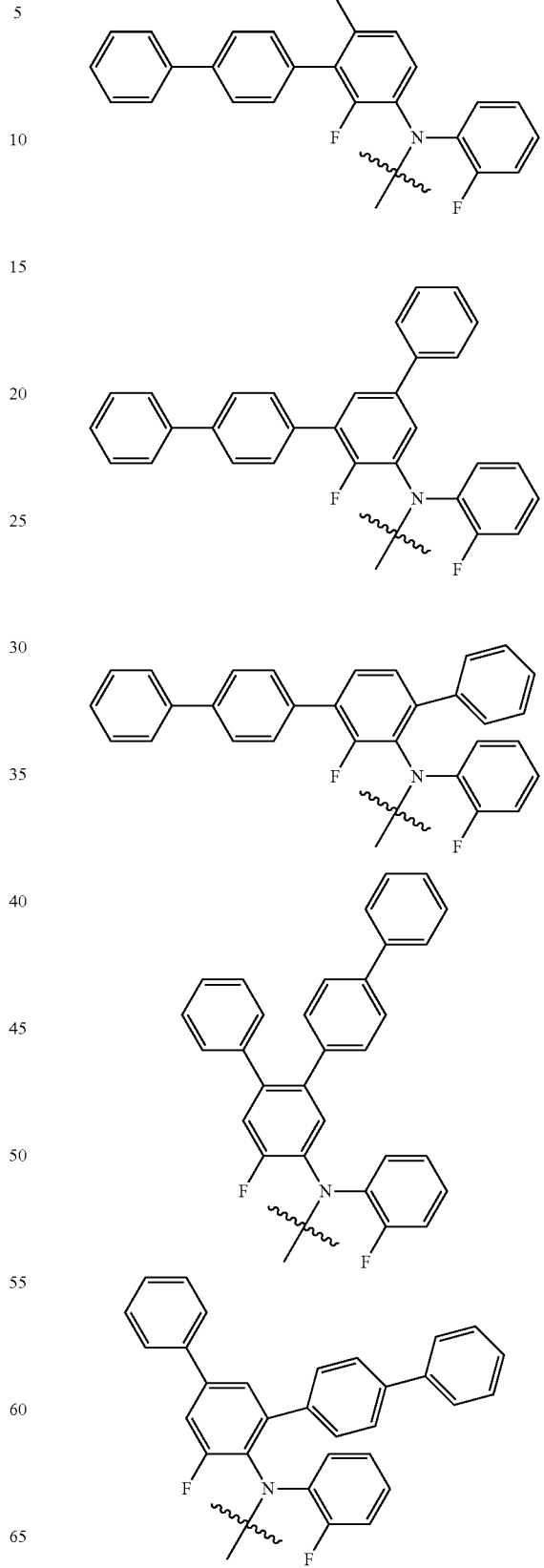

-continued
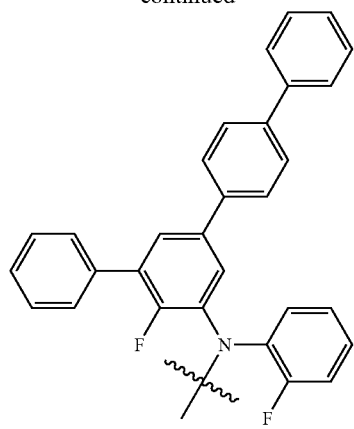
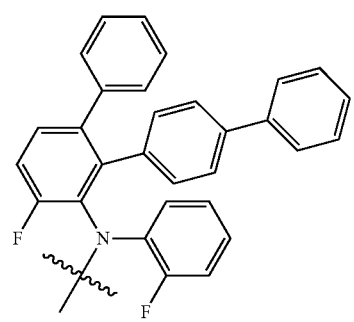
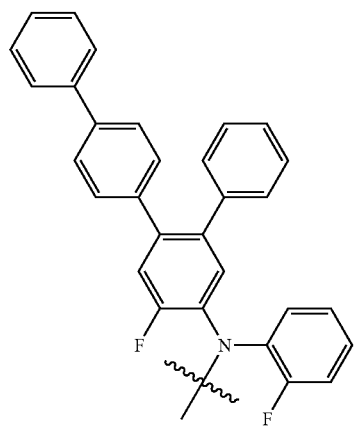
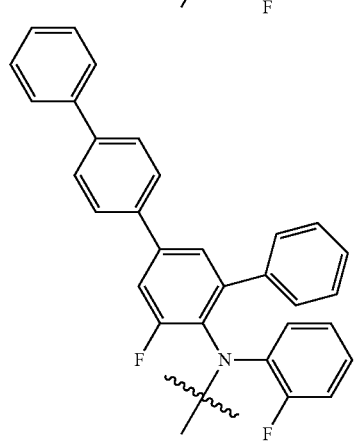
-continued
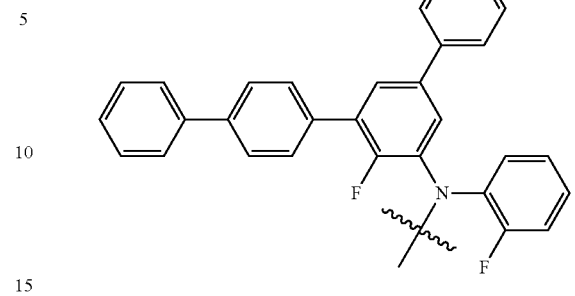
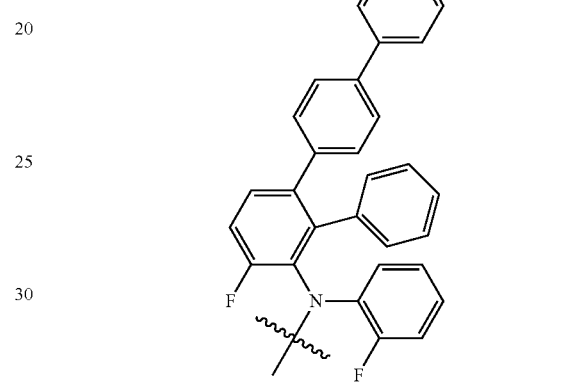
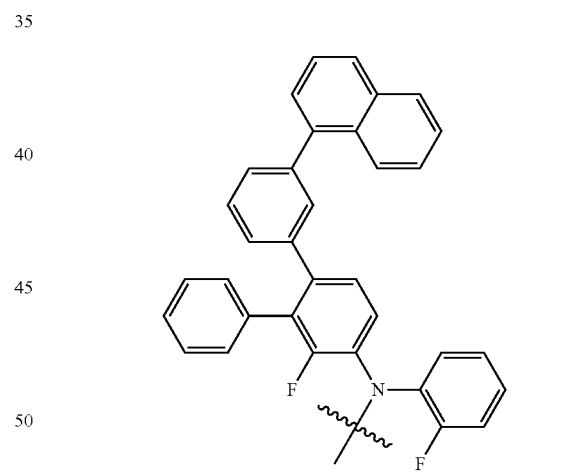
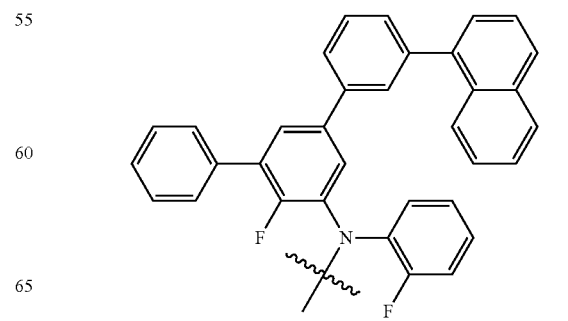

-continued
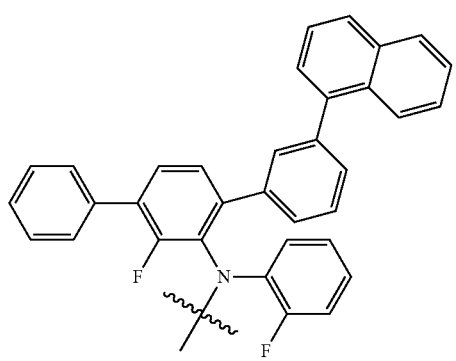
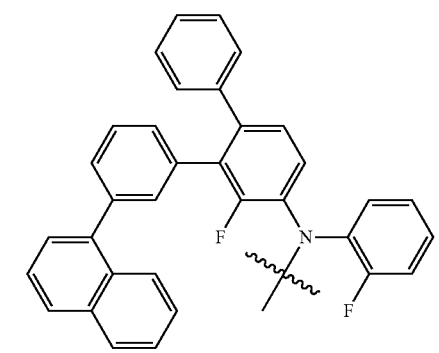
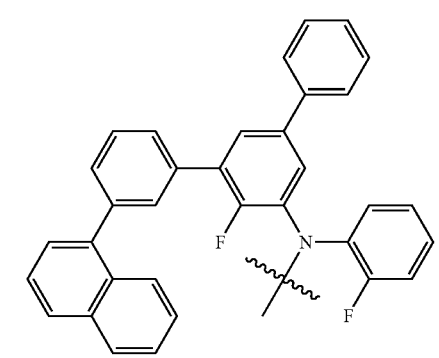
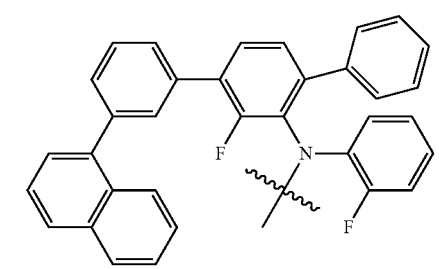
-continued
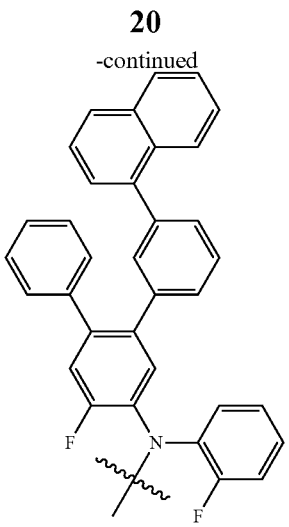
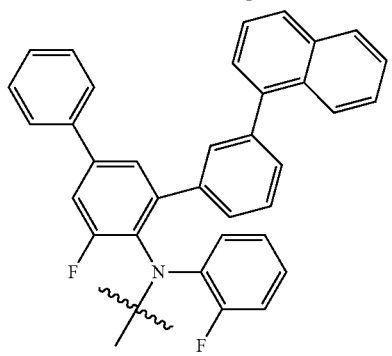
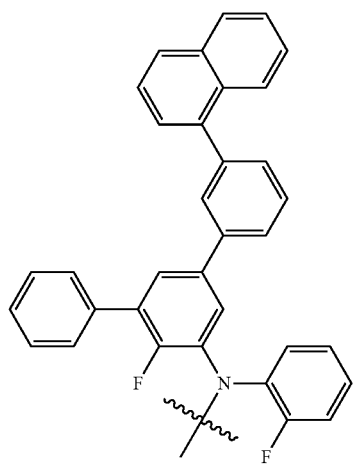
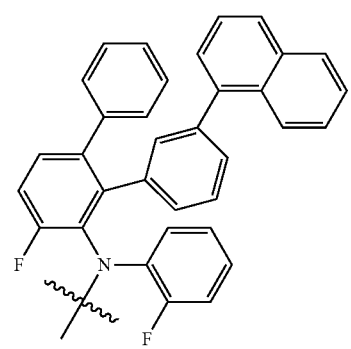

21
-continued
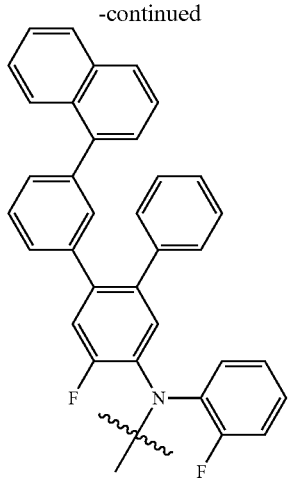
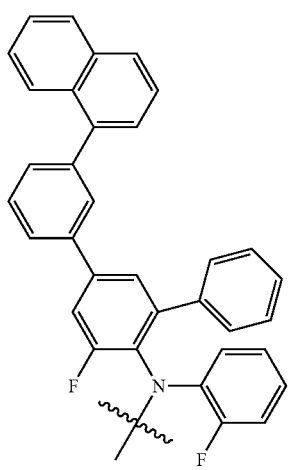
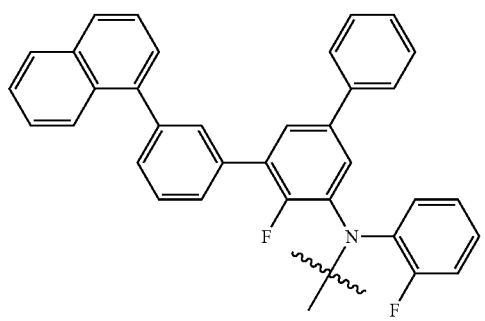
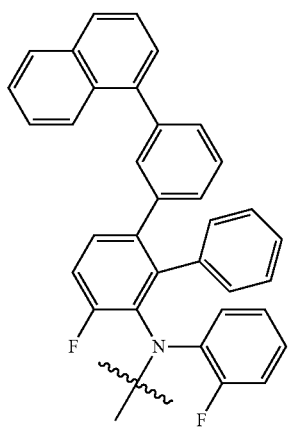
22
-continued
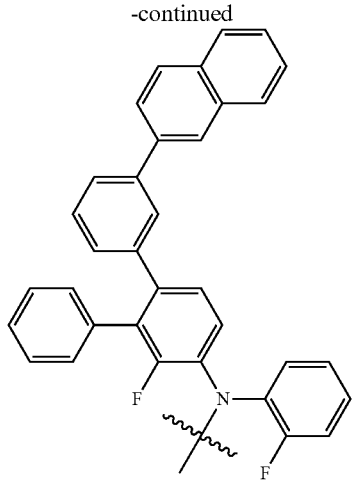
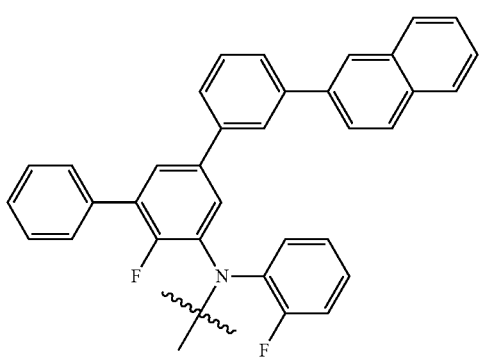
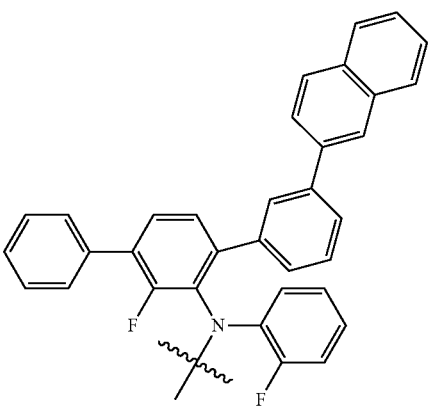
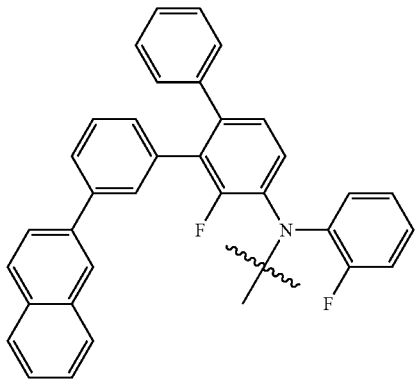

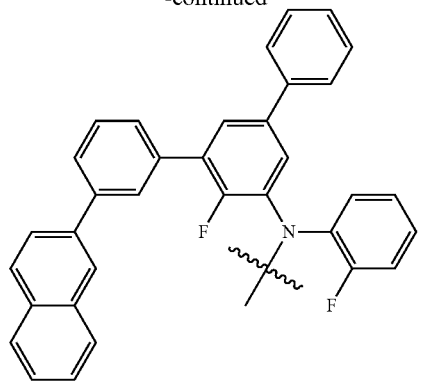
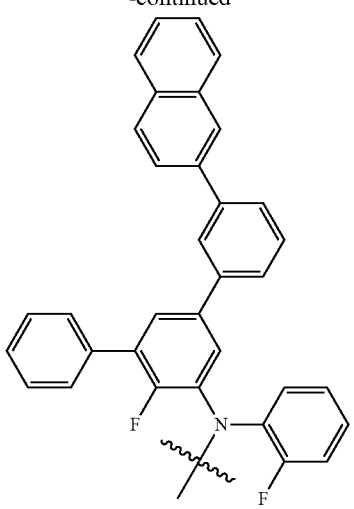
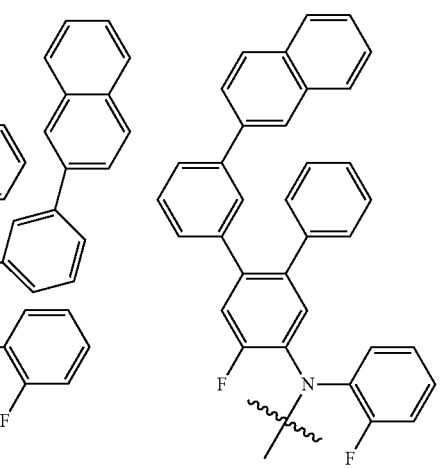
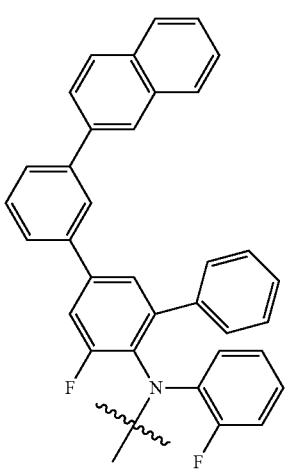

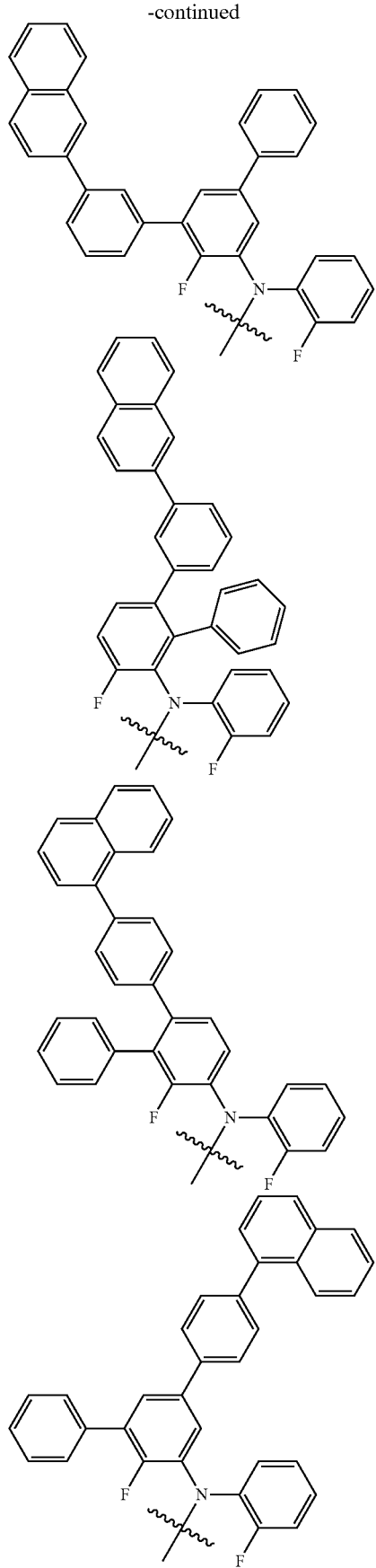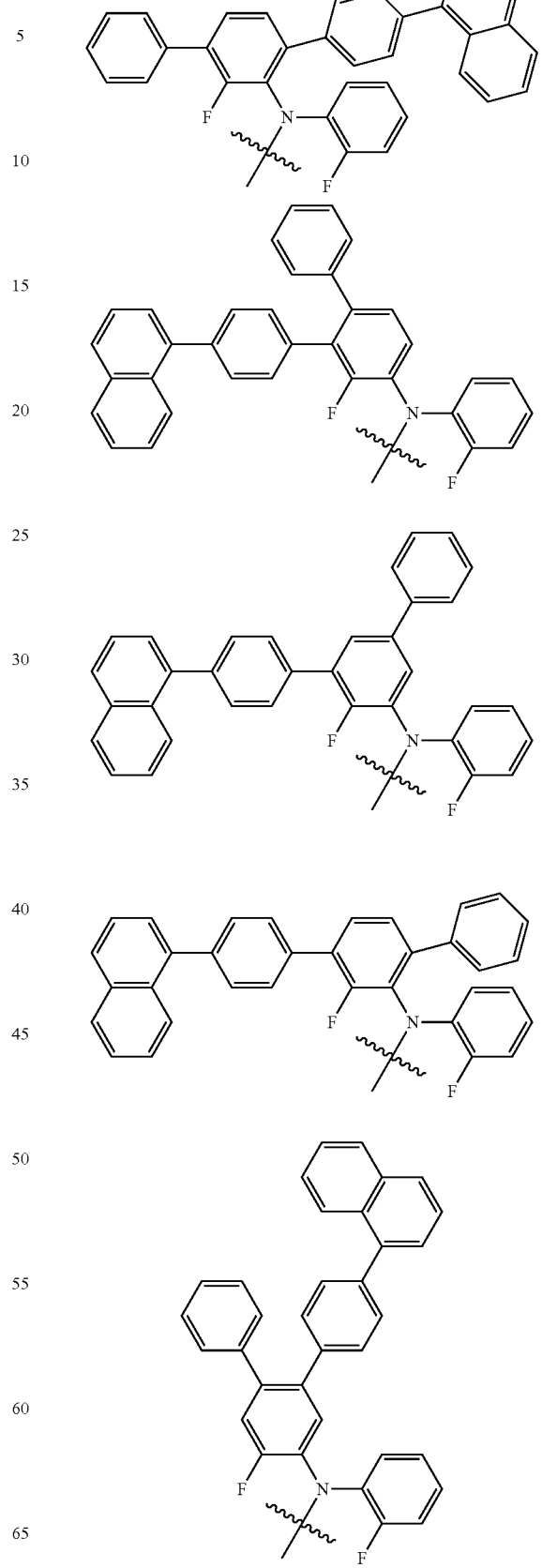

-continued
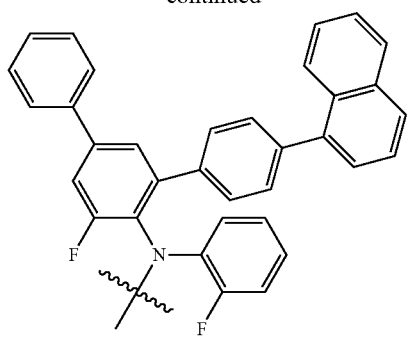
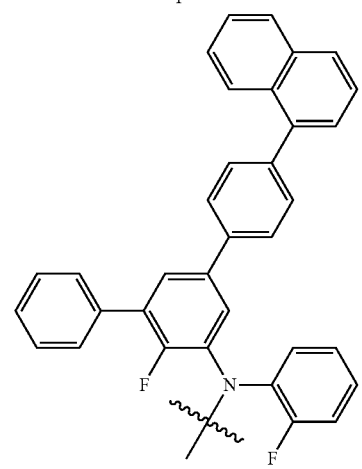
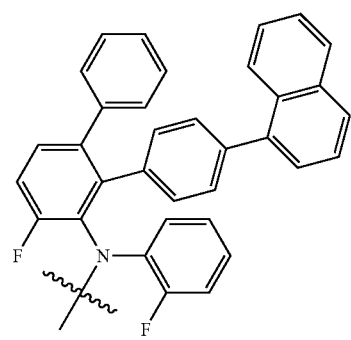
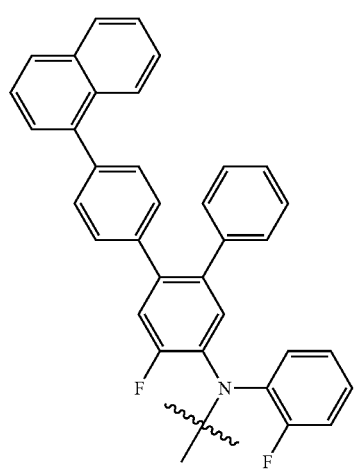
-continued
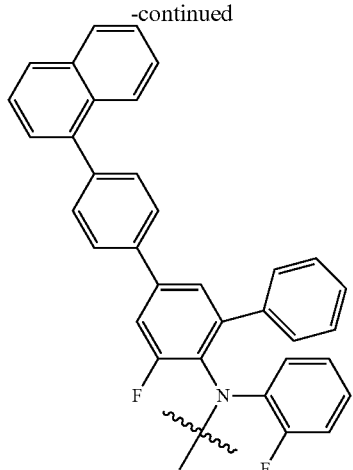
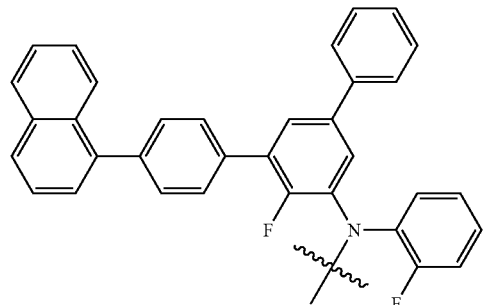
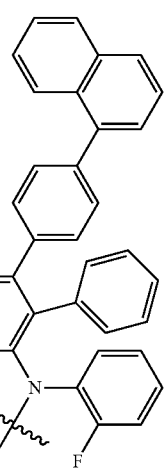
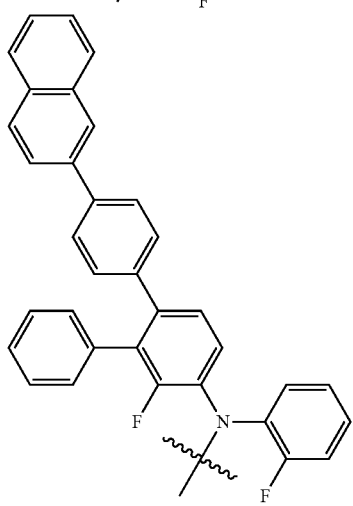

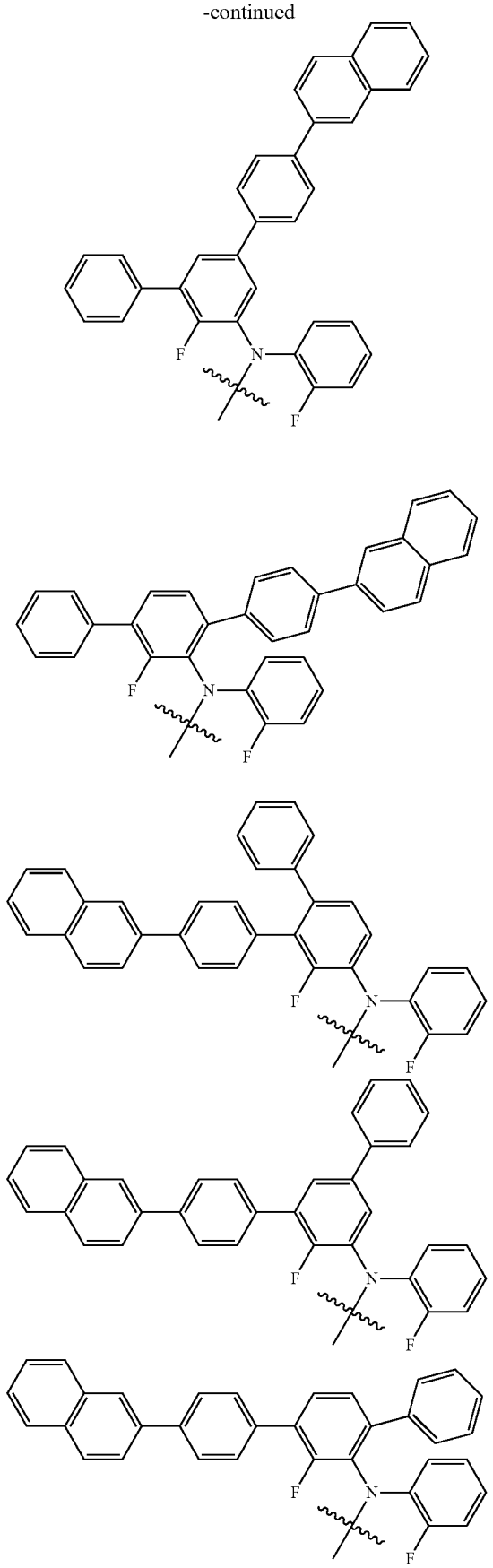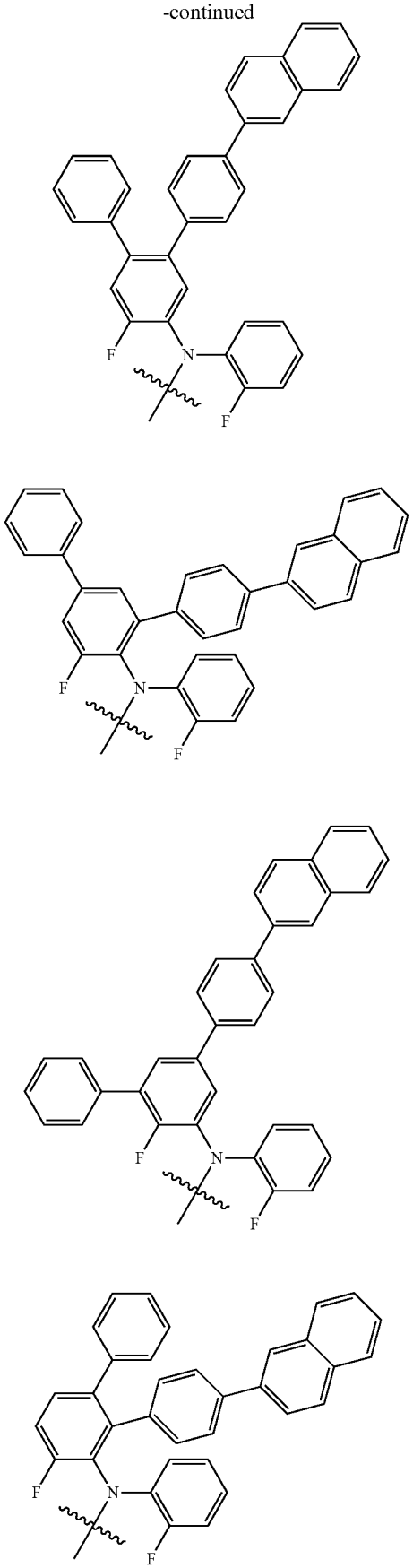

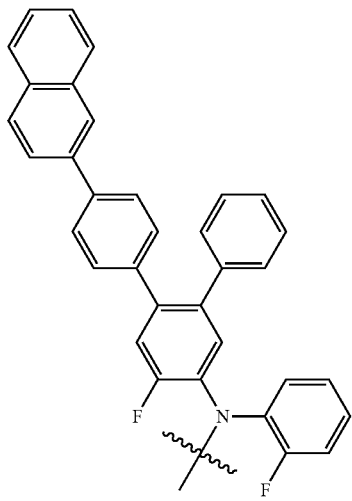
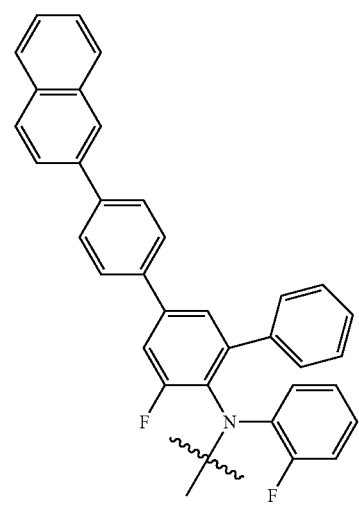
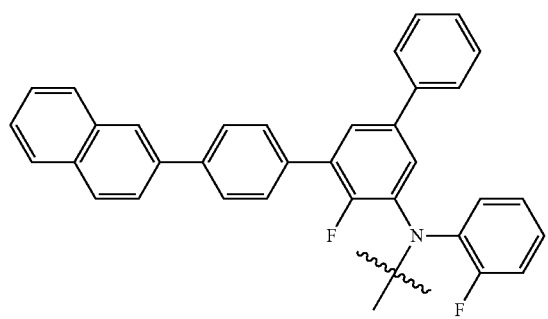
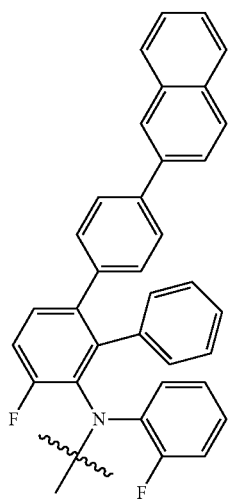
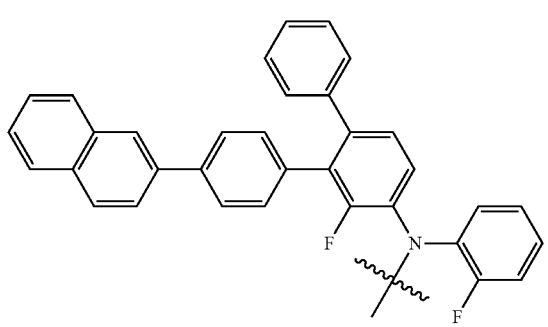
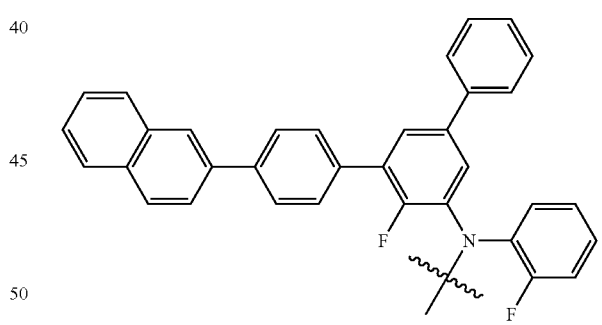
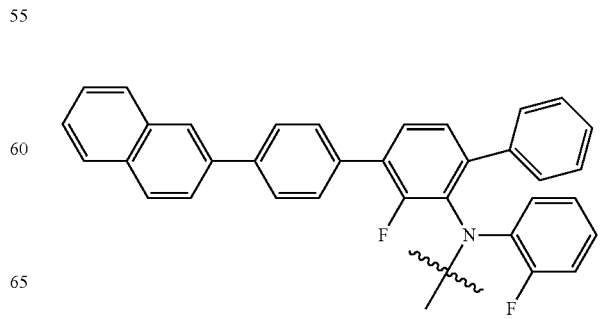

33
-continued
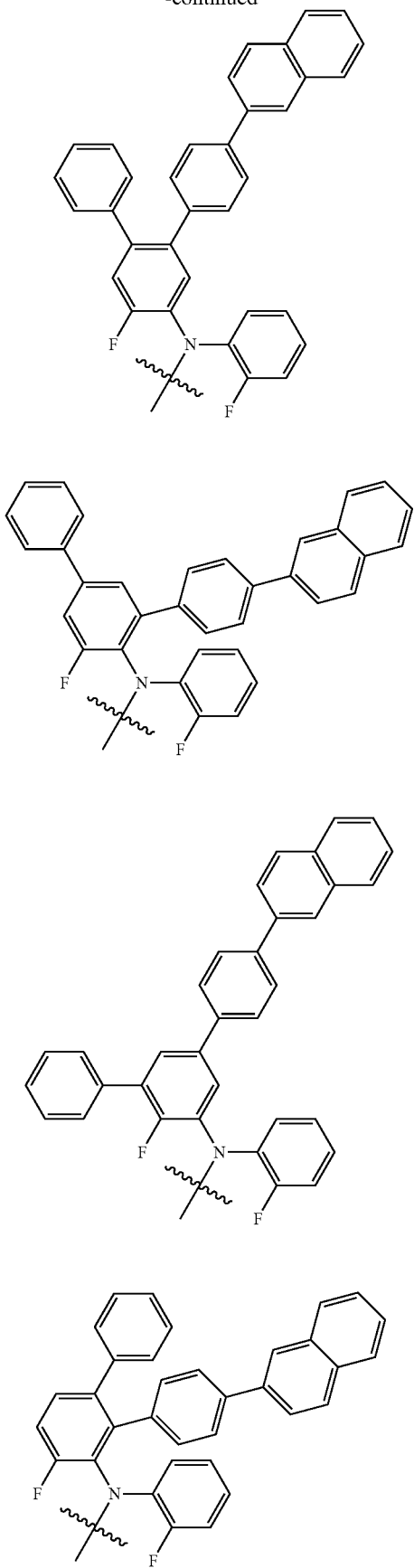
34
-continued
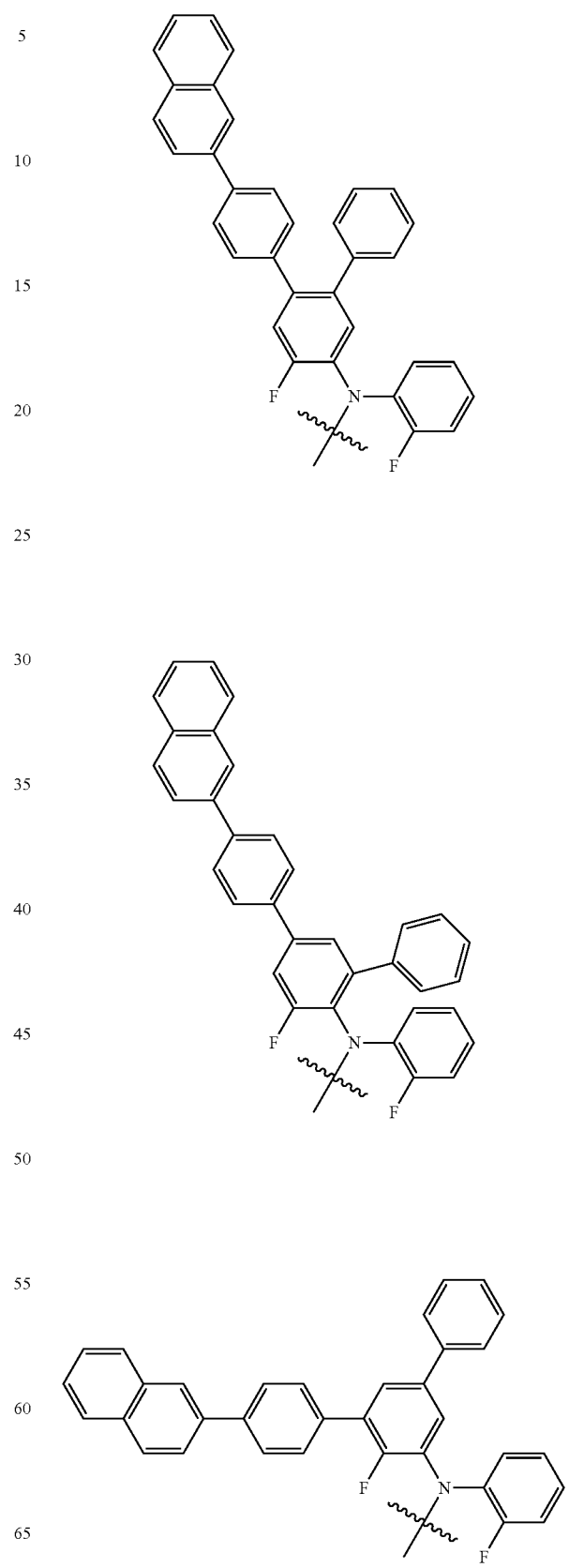

-continued
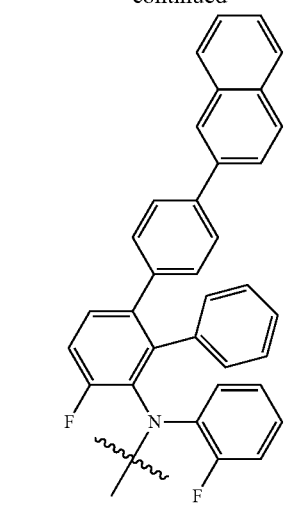
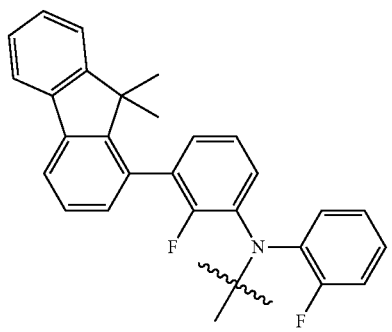
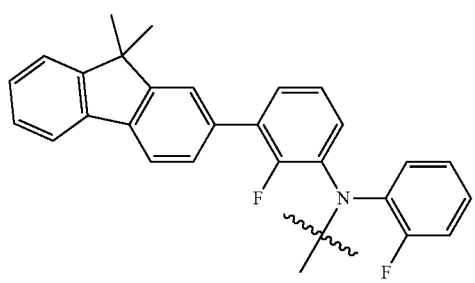
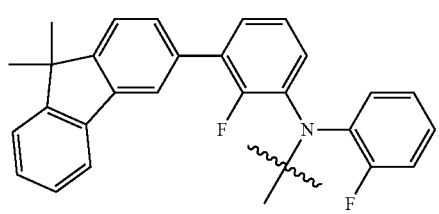
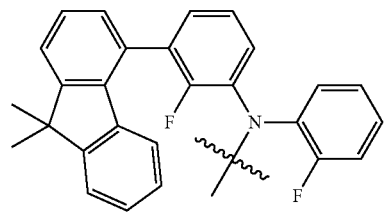
-continued
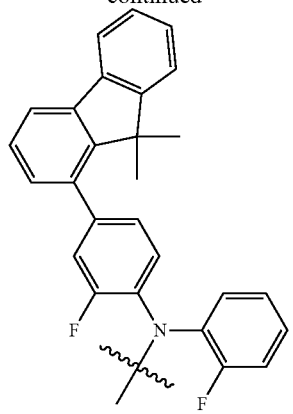
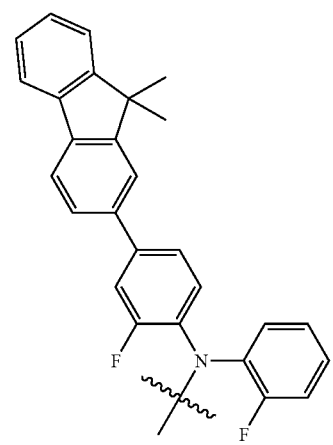
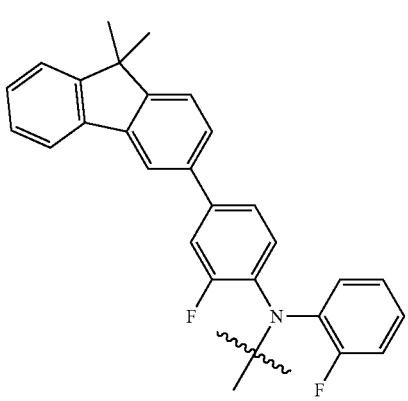
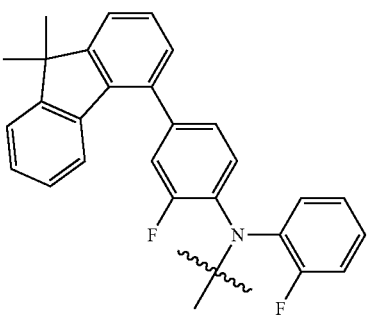

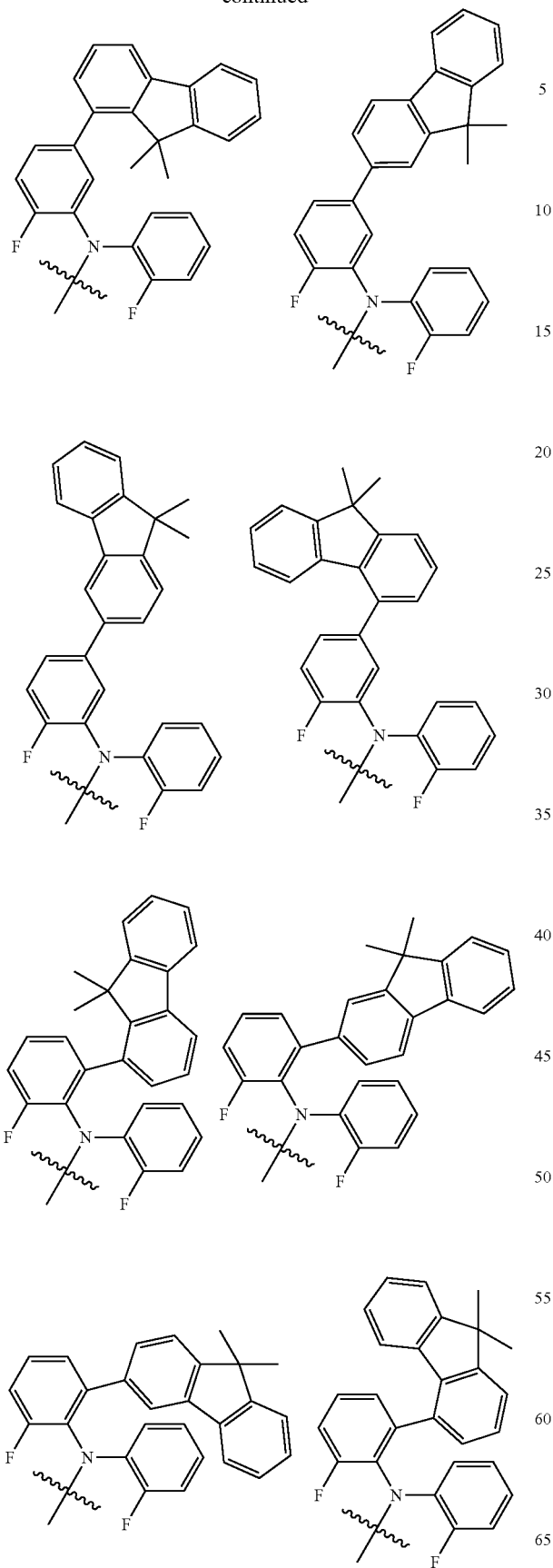
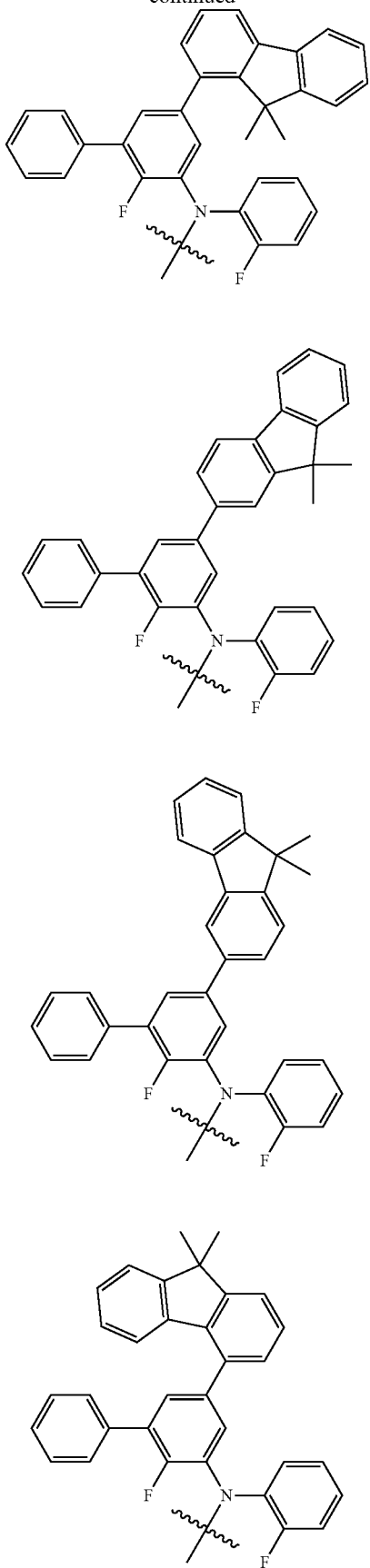

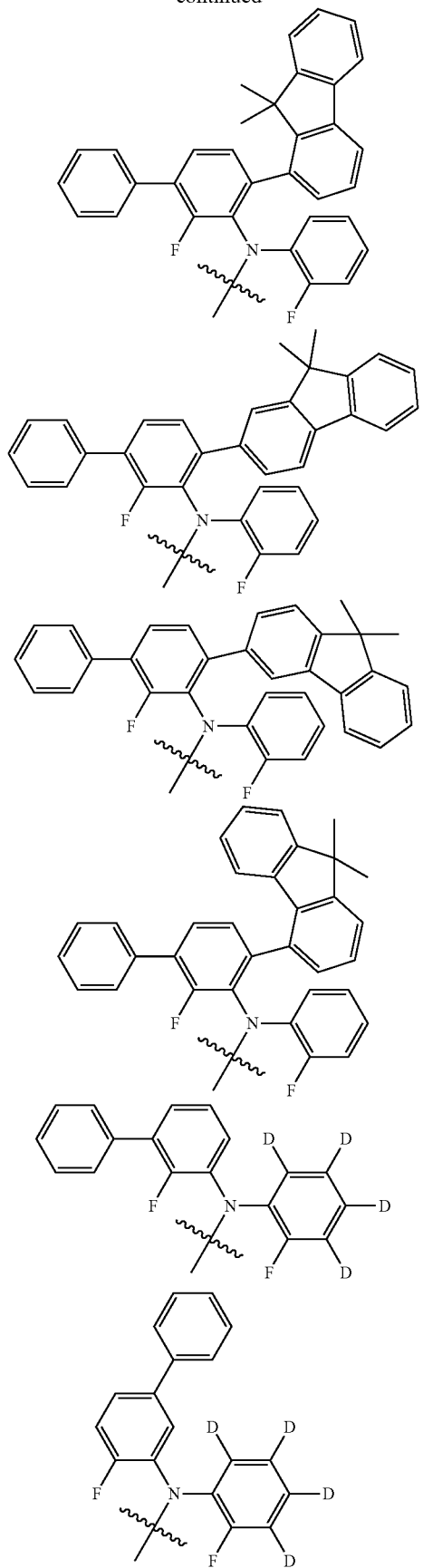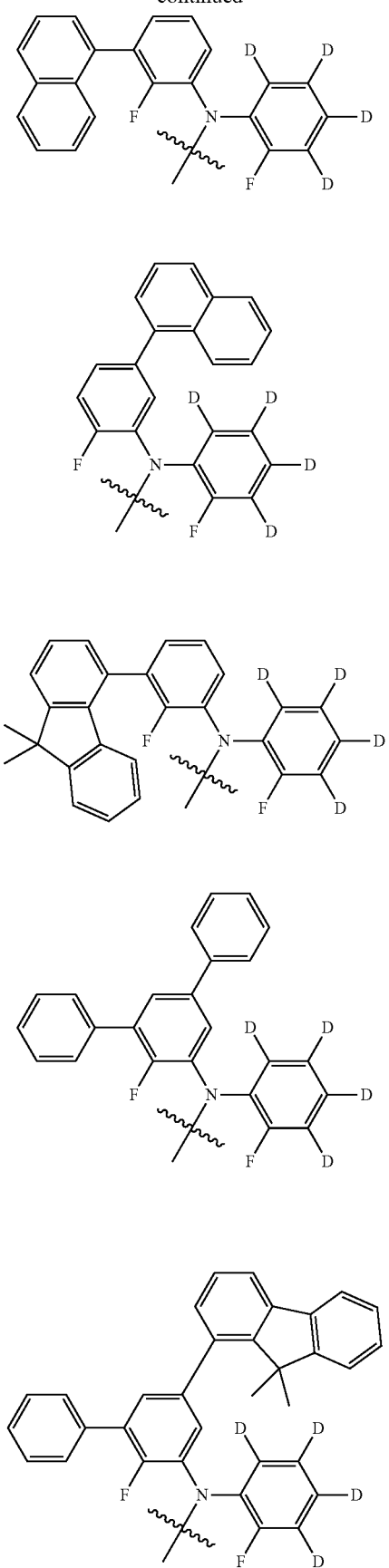

-continued
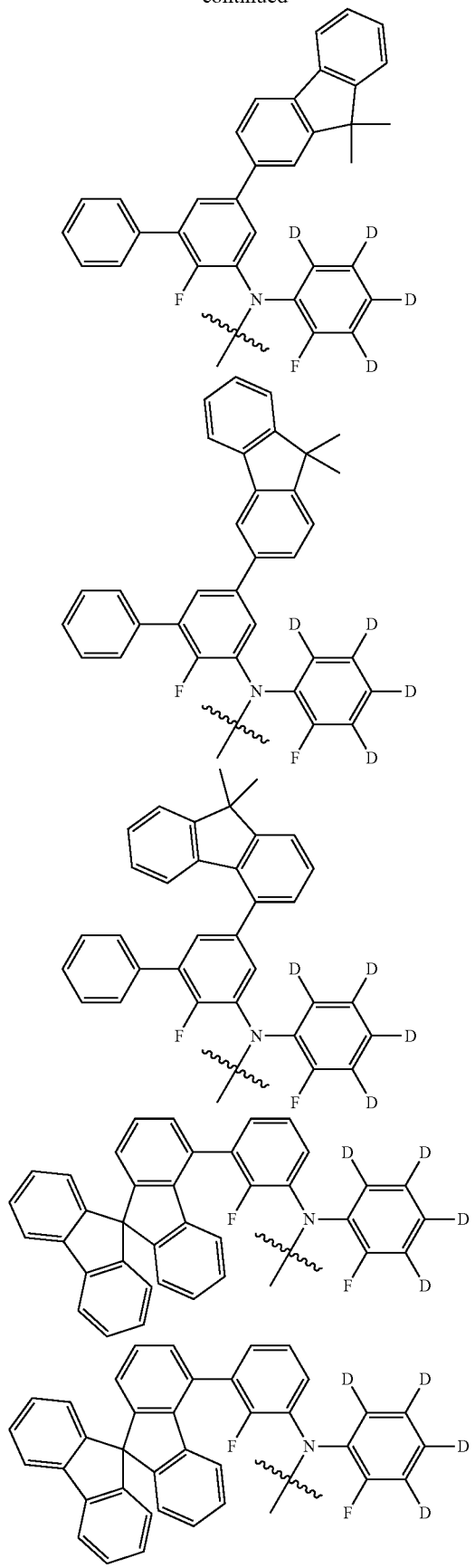
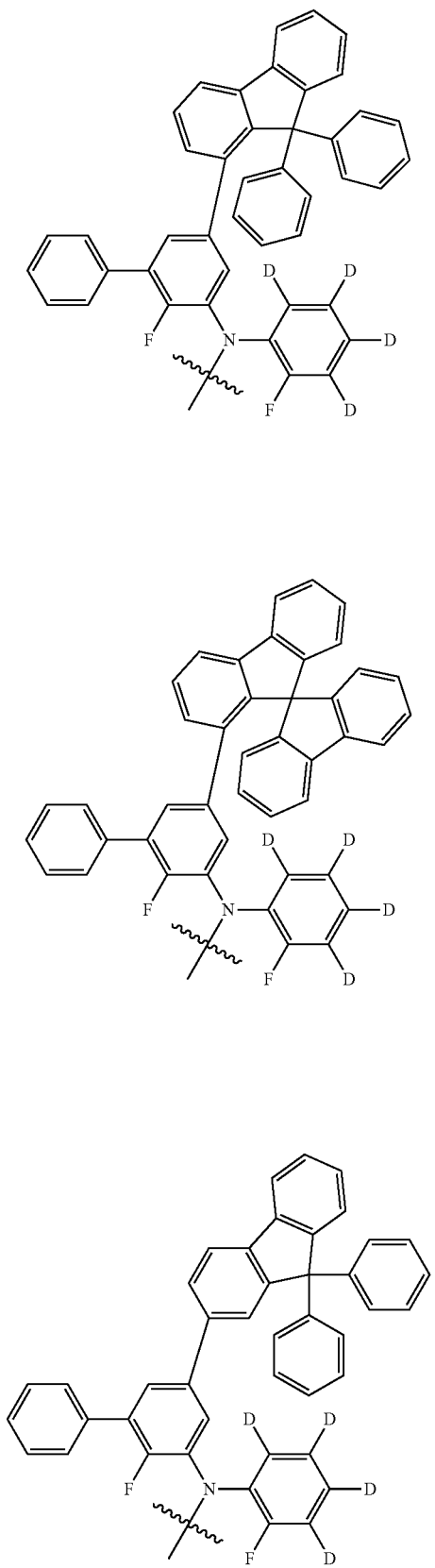

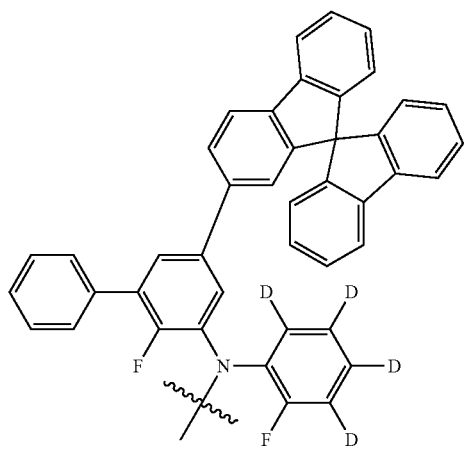
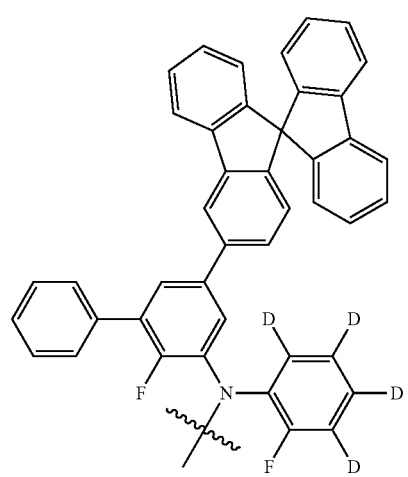
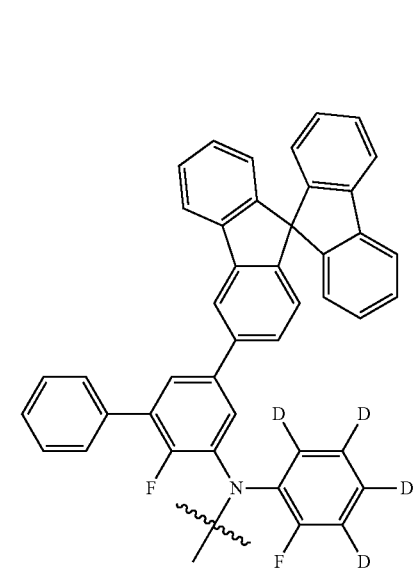
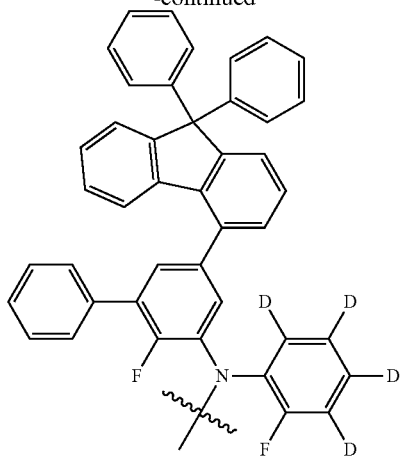
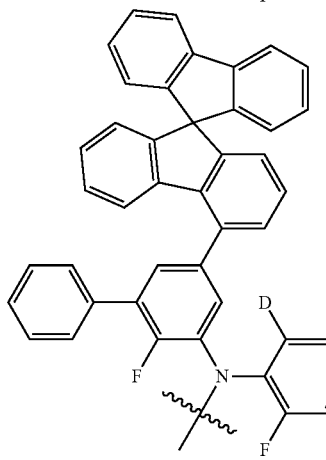
In some other embodiments, in Formula 1, a first aryl group of
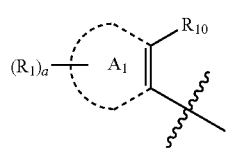
in a second diarylamino group represented by
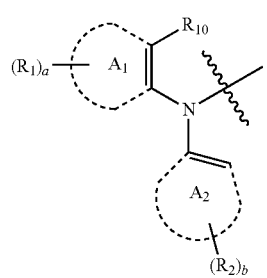
may be selected from, not limited to, the groups represented by the following formulae:

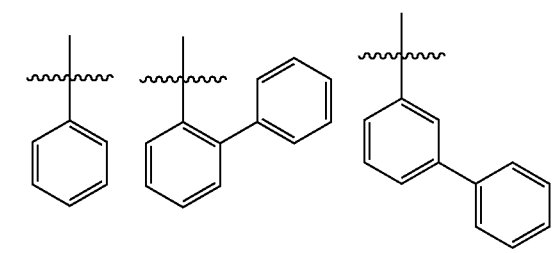
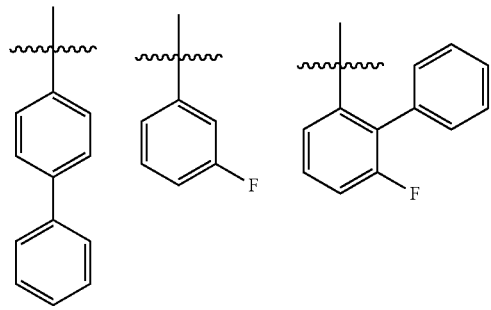
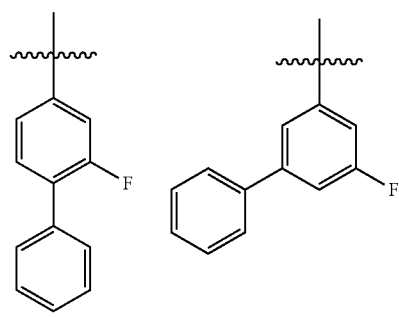
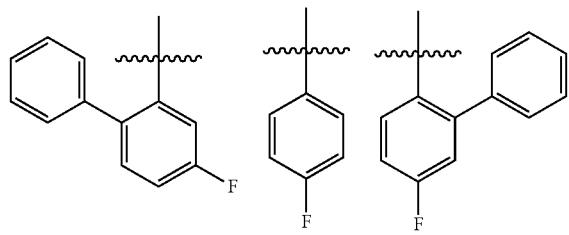
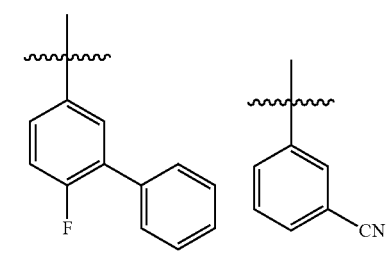
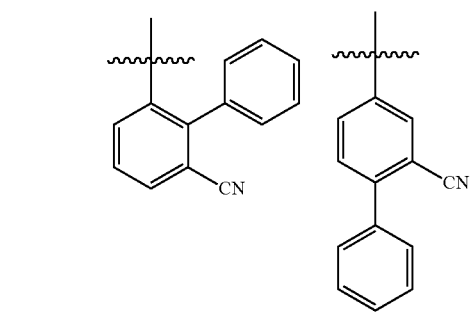
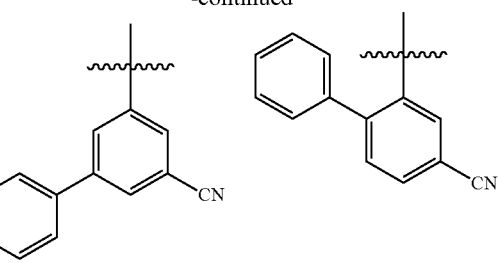
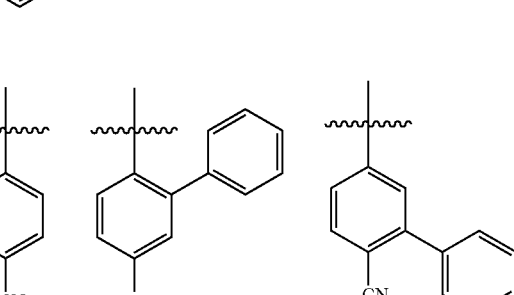
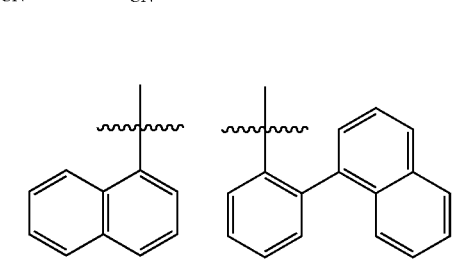
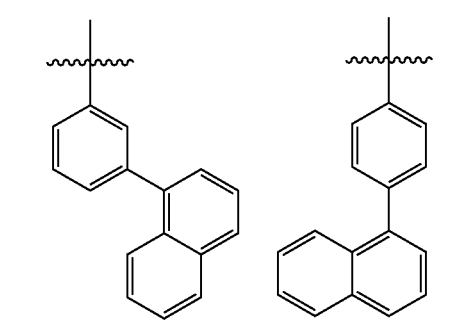
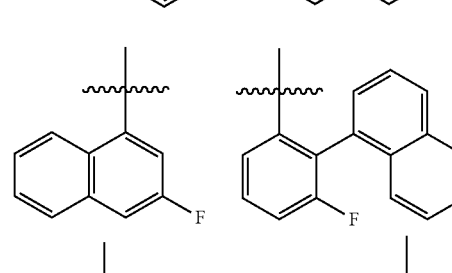
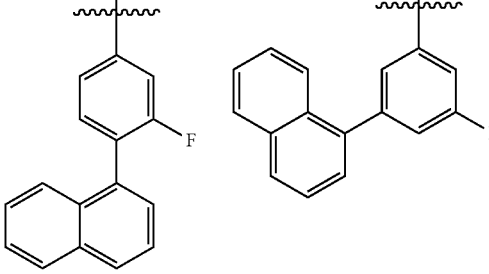

-continued
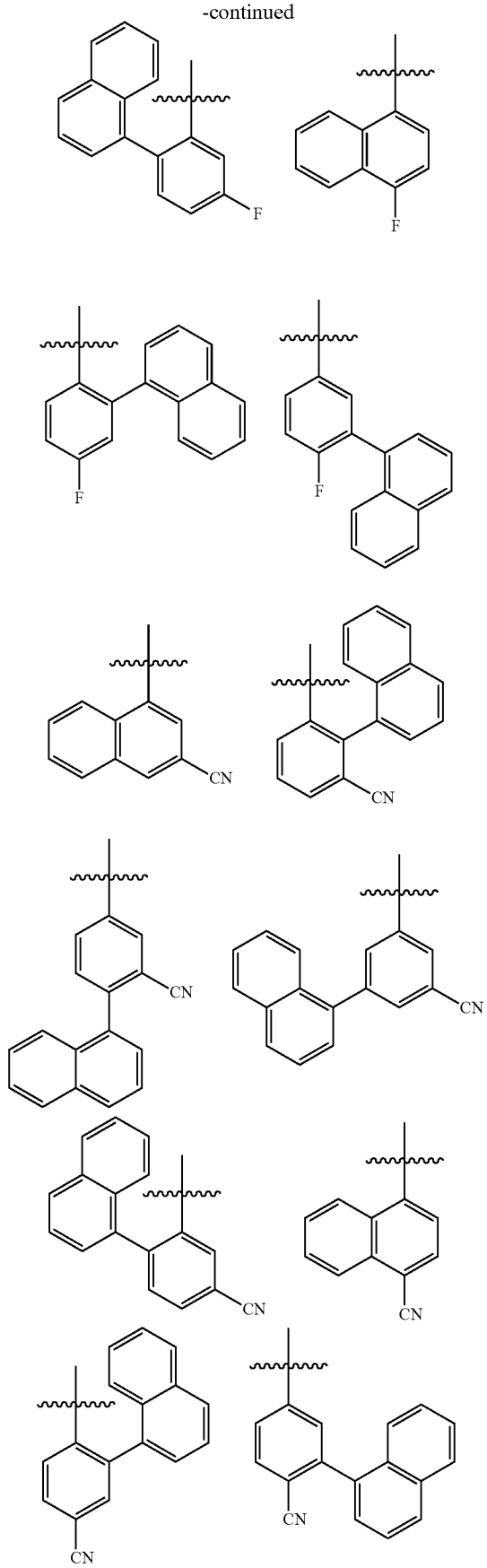
-continued
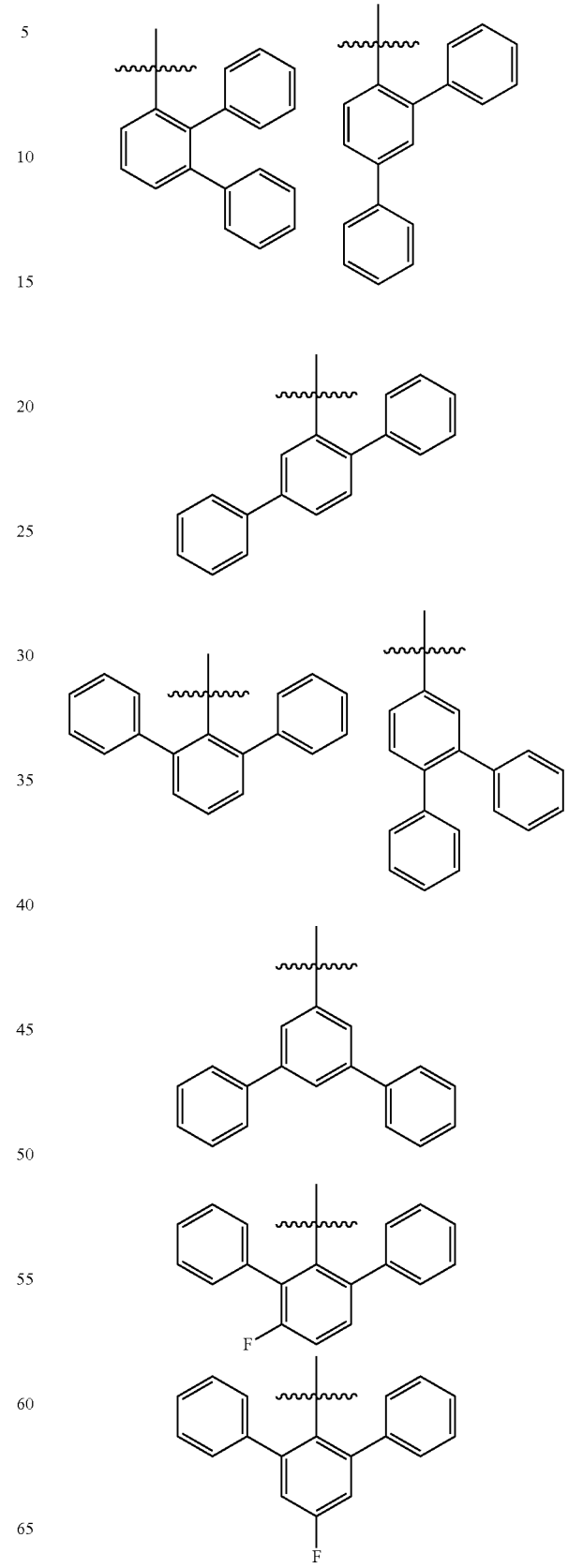

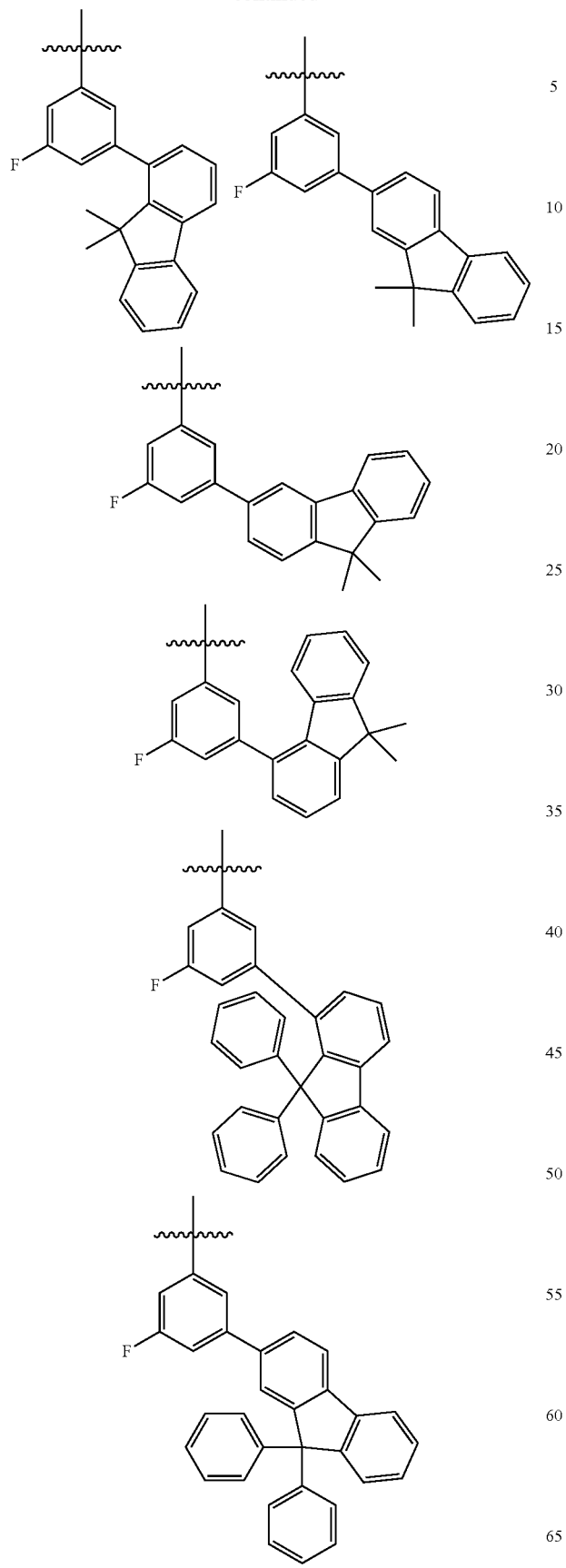
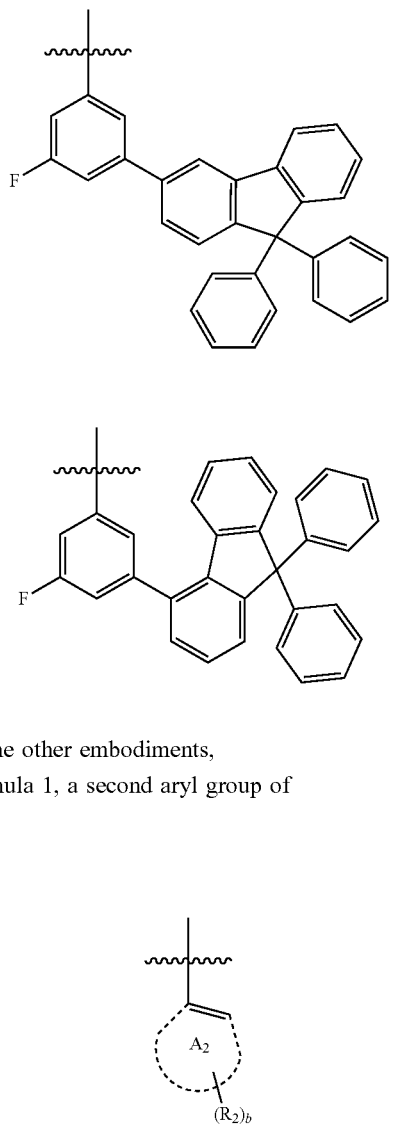
In some other embodiments, , in Formula 1, a second aryl group of
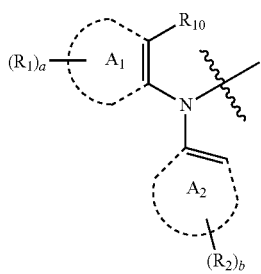
in a second diarylamino group represented by
may be selected from, not limited to, the groups represented by the following formulae:

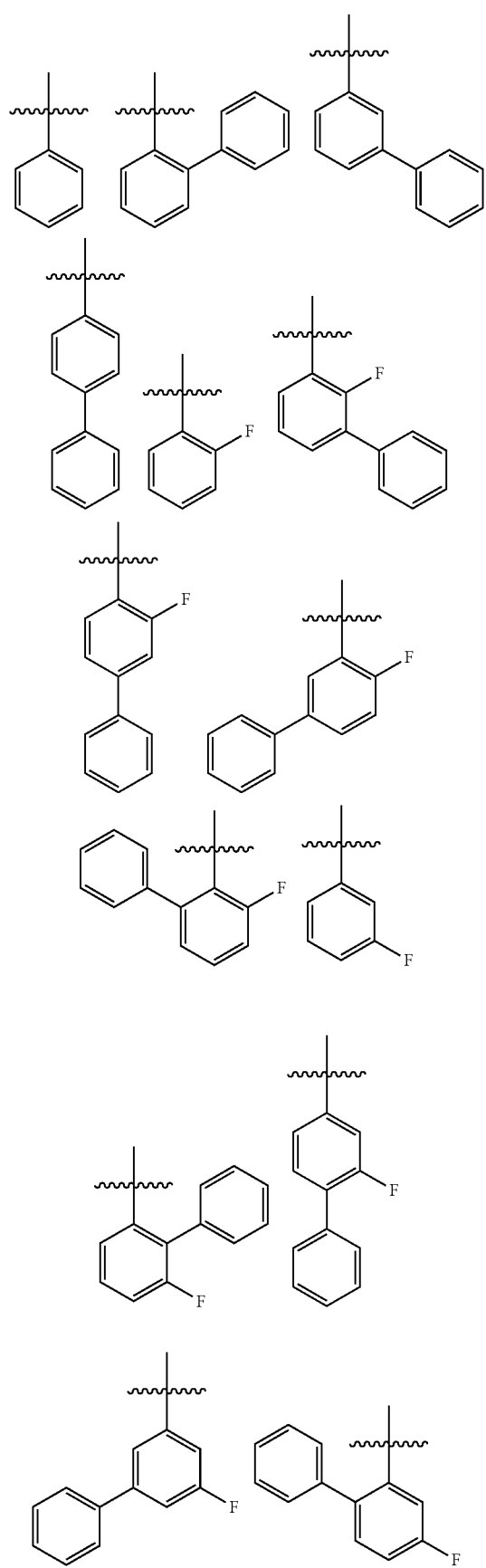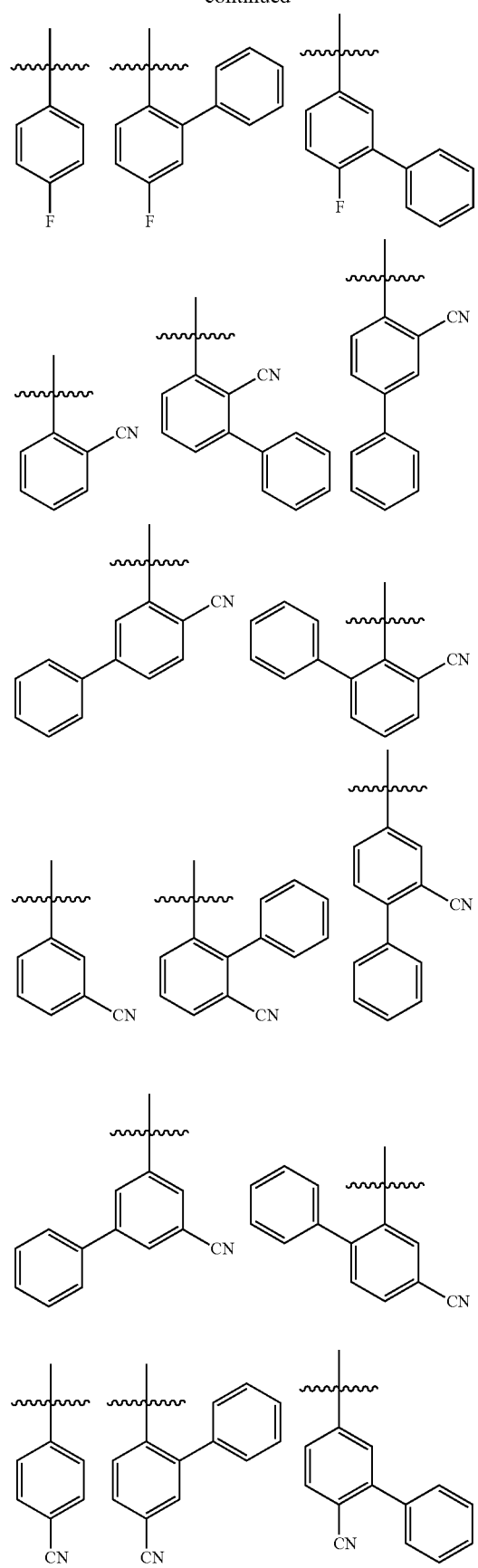

53
-continued
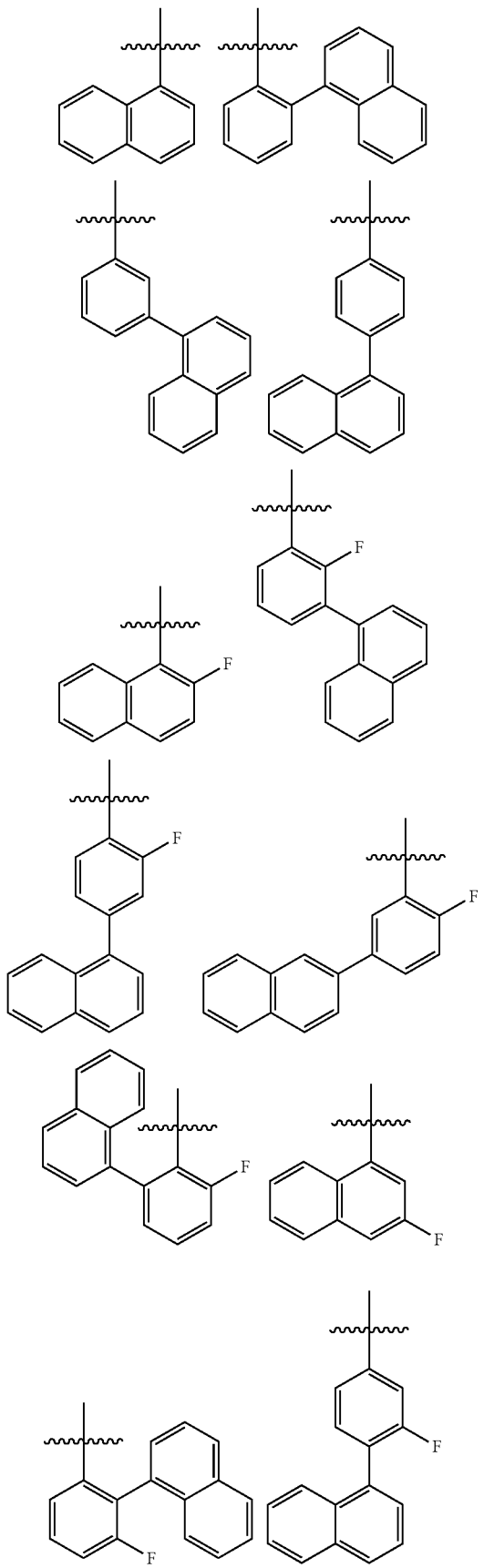
54
-continued
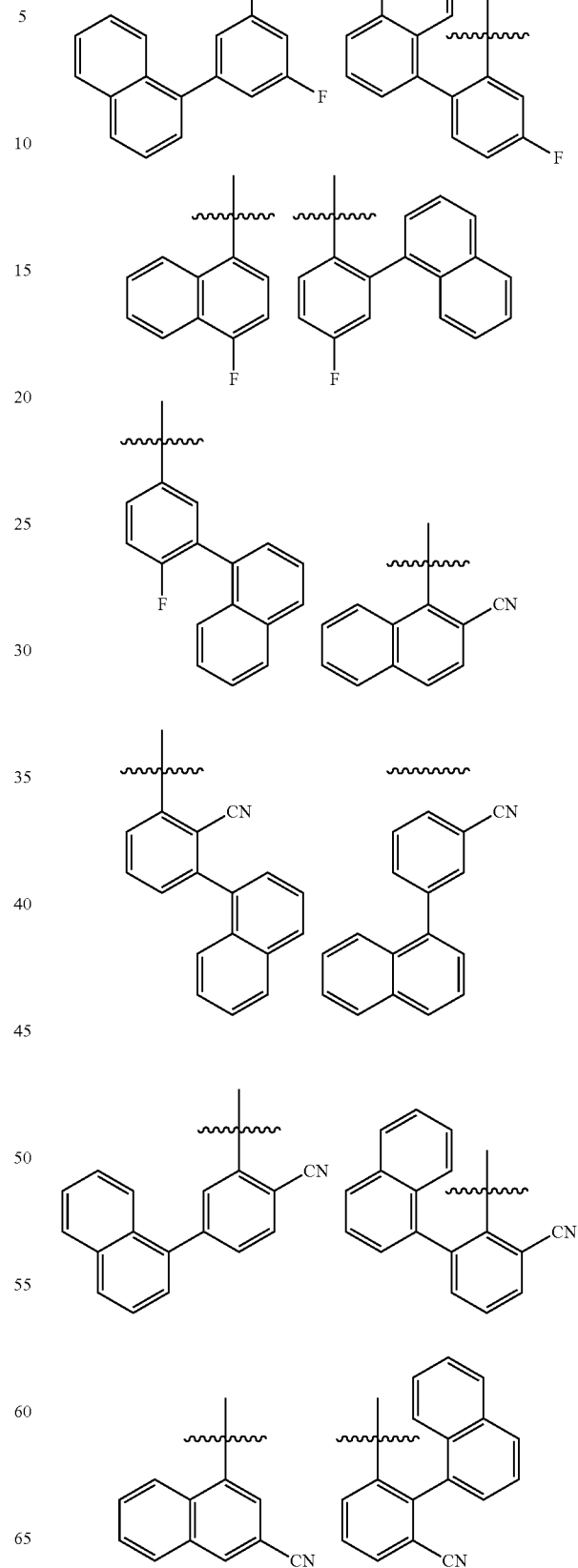

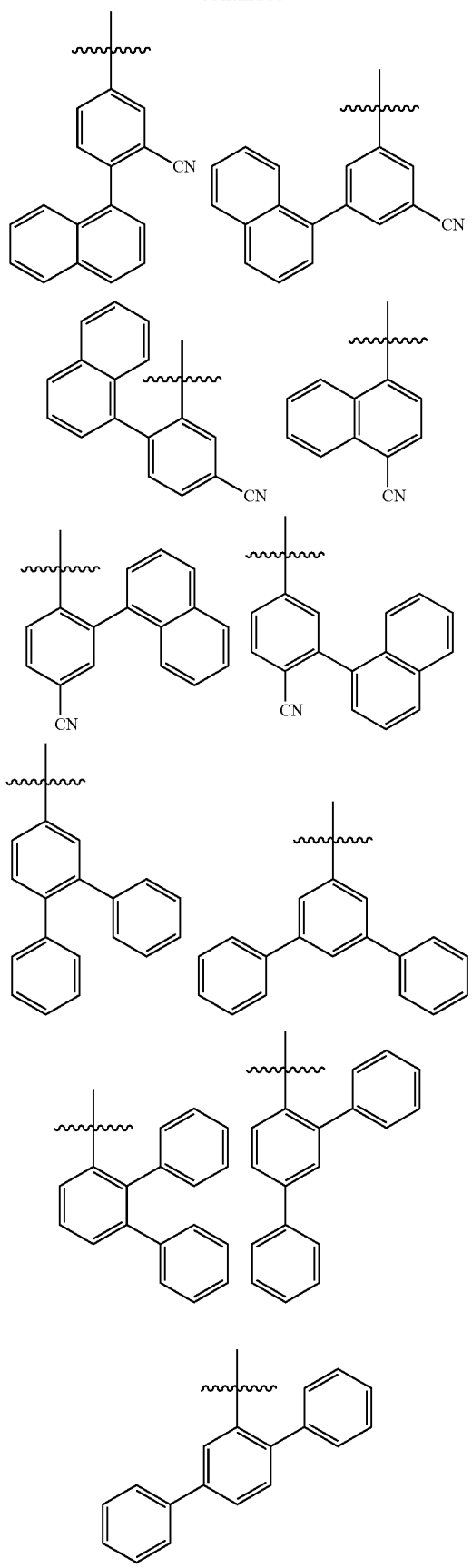
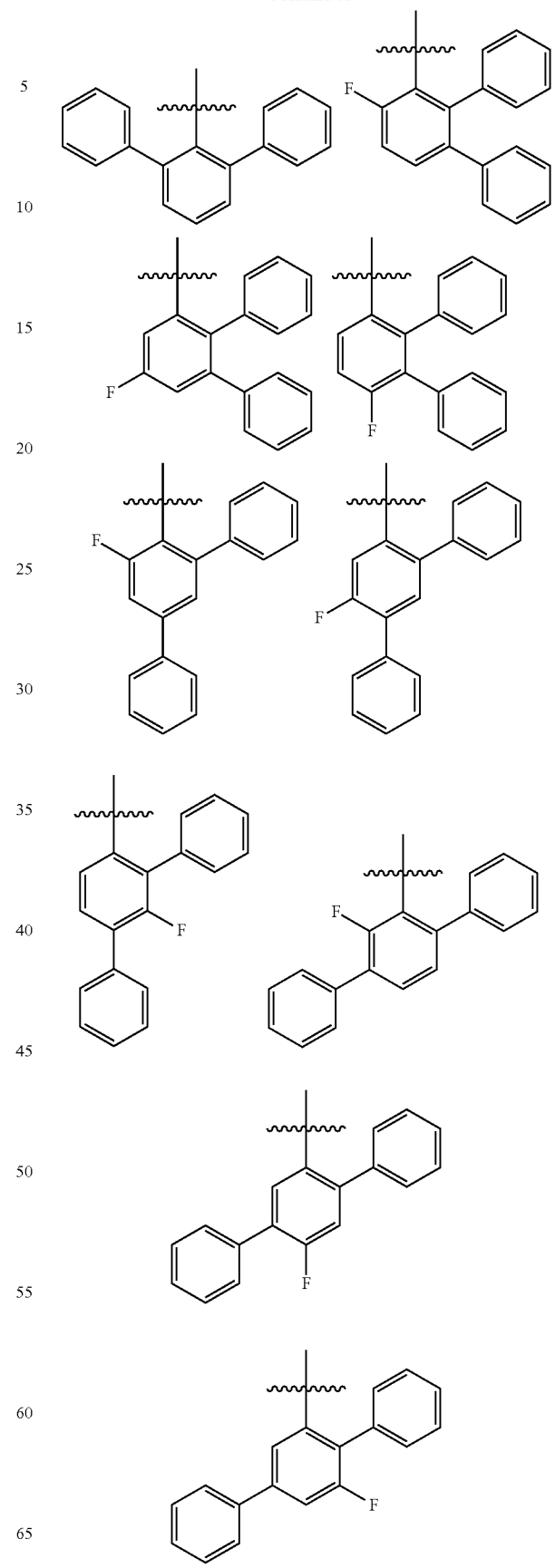

57
-continued
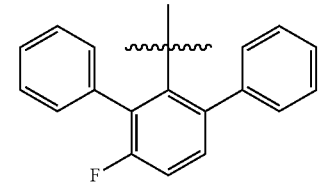
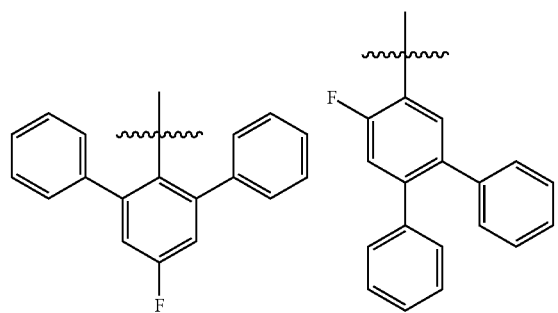
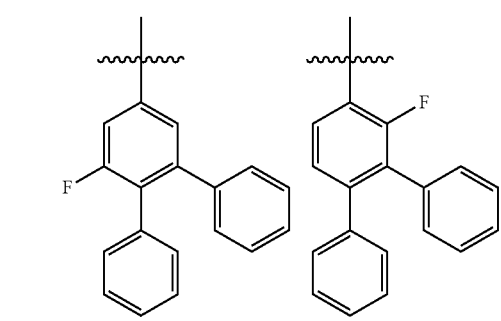
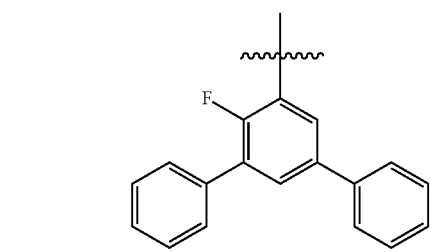
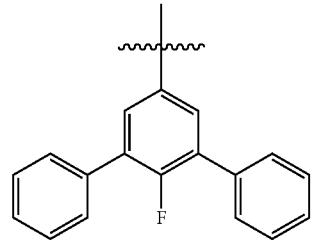
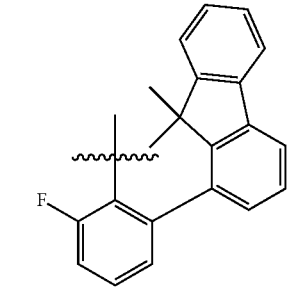
58
-continued
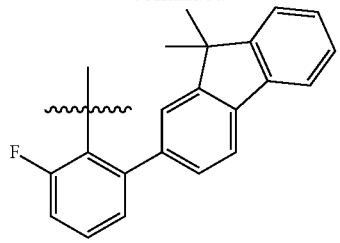
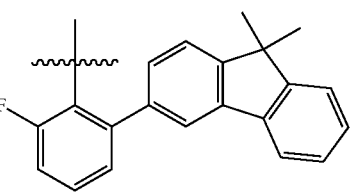
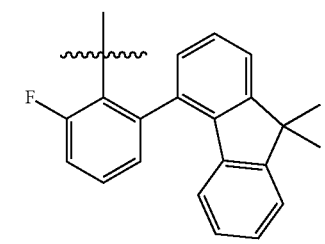
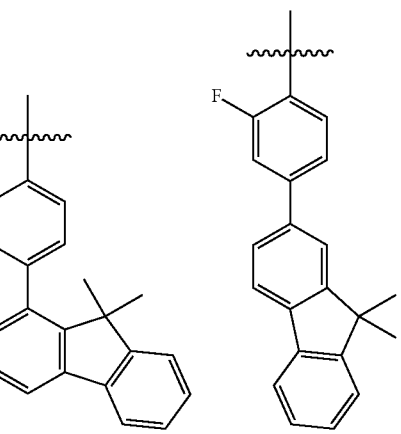
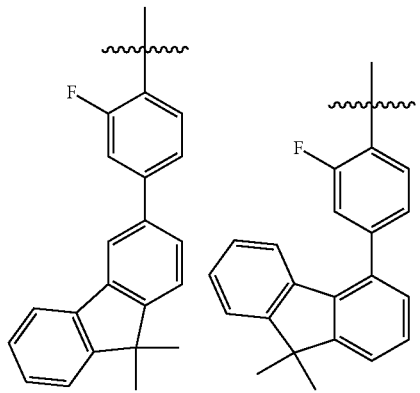

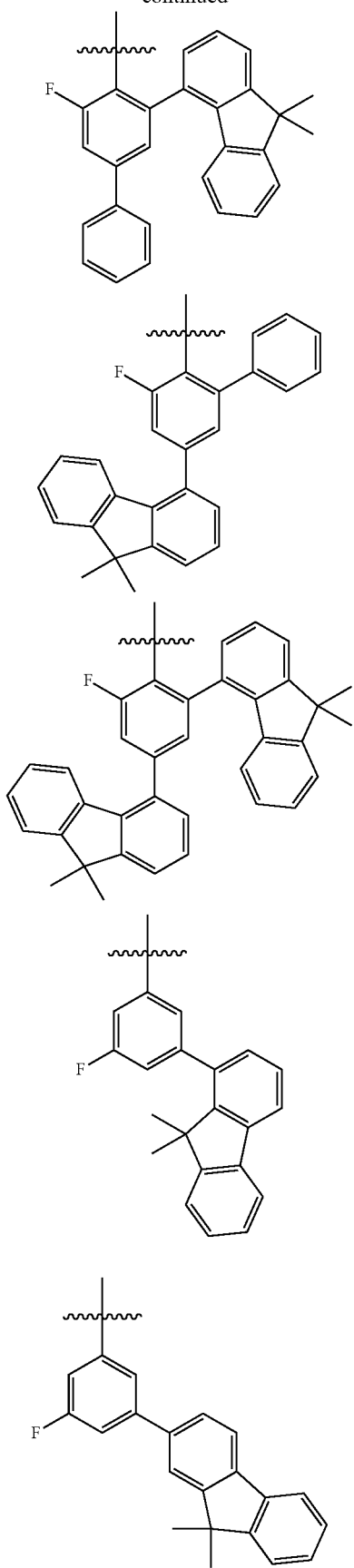
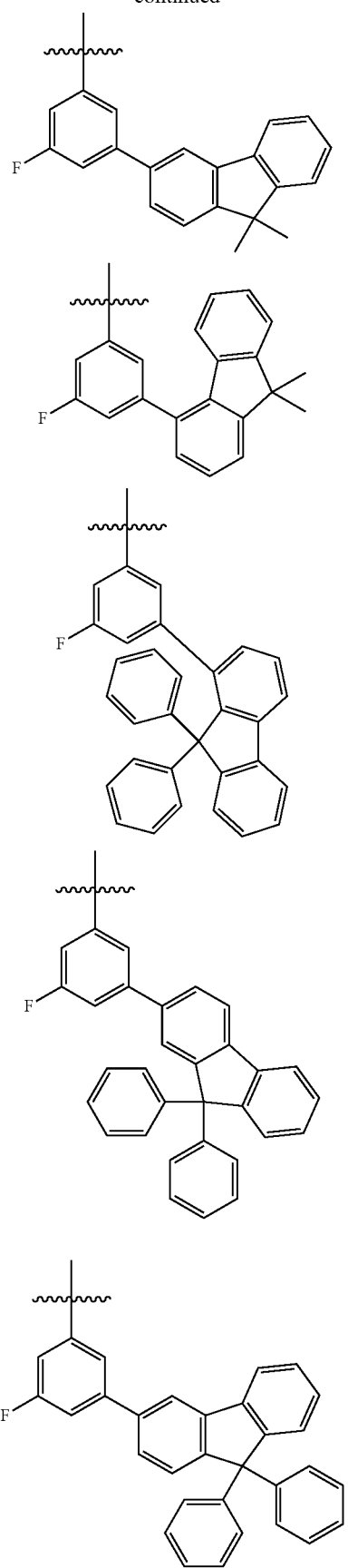

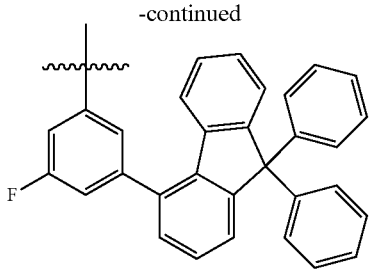
In some embodiments, the pyrene-based compound of Formula 1 above may be one of Compounds 1 to 9 below, but is not limited to:
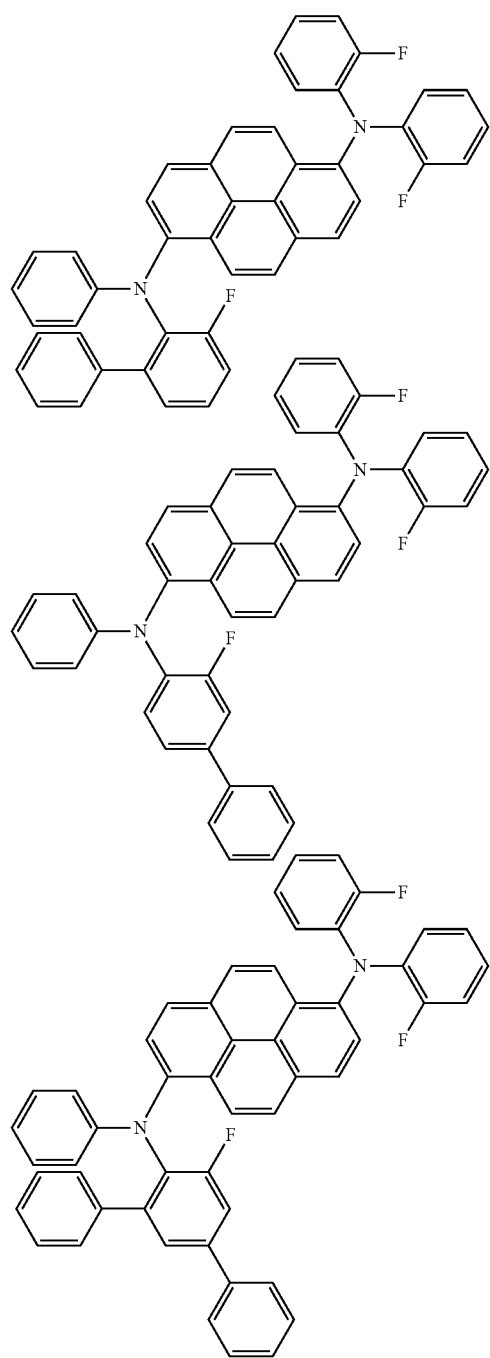
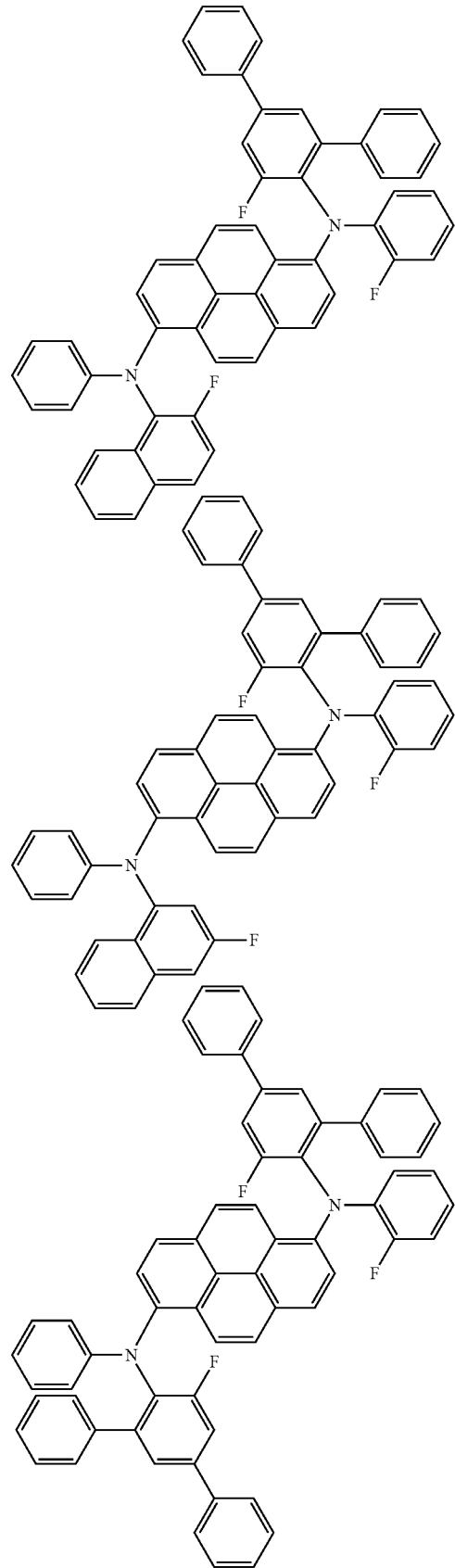

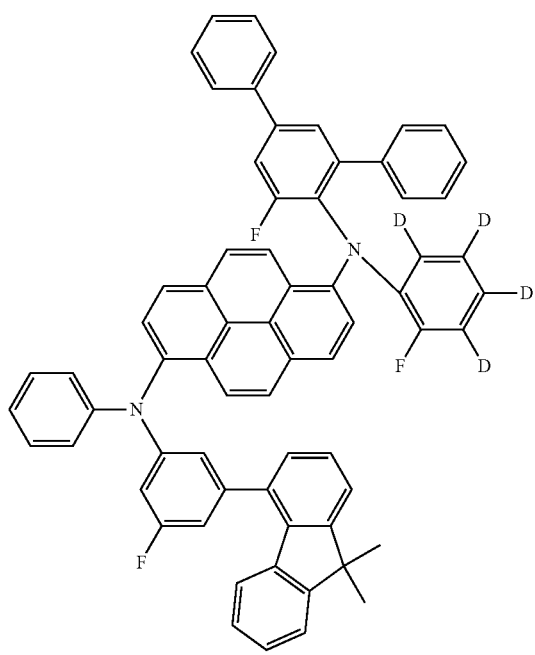

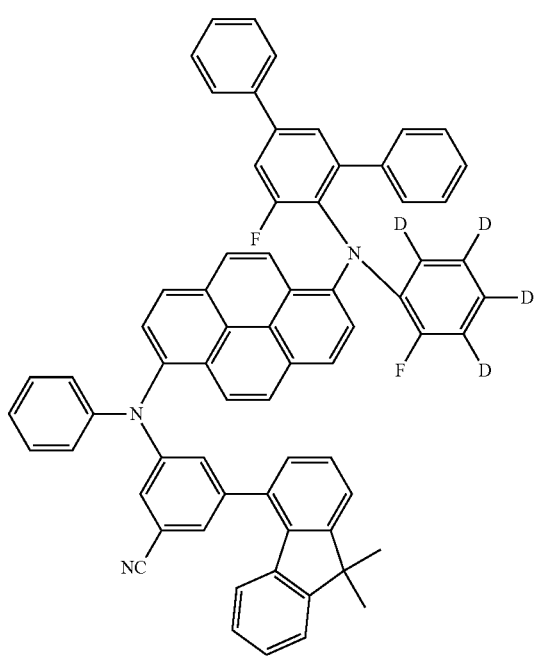

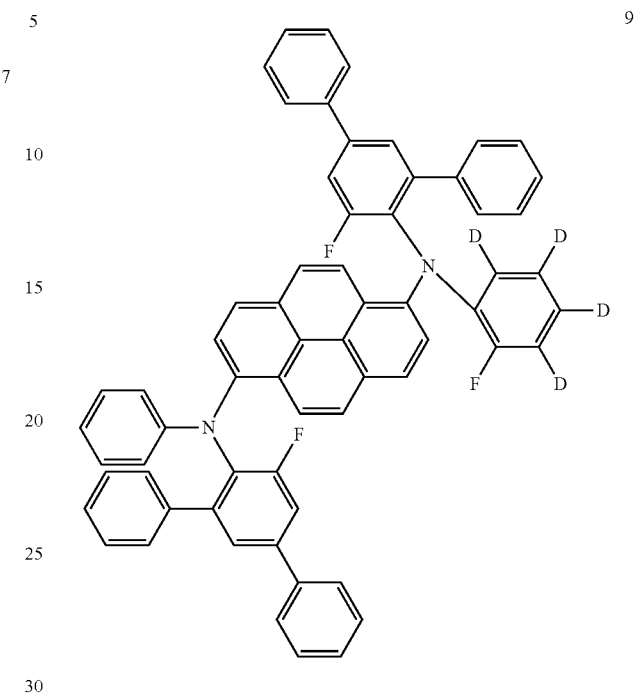

In Formula 1 above, $E_1$ and $E_2$ in the first diarylamino group represented by

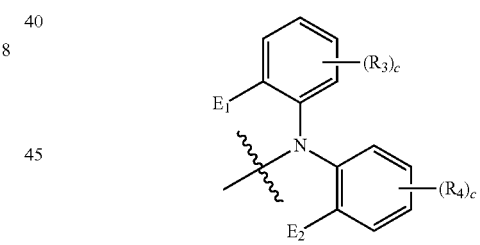

may be each independently an electron withdrawing group selected from —F; —CN; and a $C_1$-$C_{60}$ alkyl group substituted with at least one —F. Accordingly, the pyrene-based compound of Formula 1 may emit blue light having a relatively short wavelength. For example, the pyrene-based compound of Formula 1 above in toluene may have a maximum peak of about 450 nm or less in photoluminescence (PL) spectra. Accordingly, the pyrene-based compound of Formula 1 above may emit blue light having high color purity. For example, an organic light-emitting diode including the pyrene-based compound of Formula 1 above may emit blue light having a y coordinate with a color purity of 0.1 or less, for example, a color purity of 0.09 or less, which is near to the NTSC or sRGB specification.

Since the second diarylamino group represented by

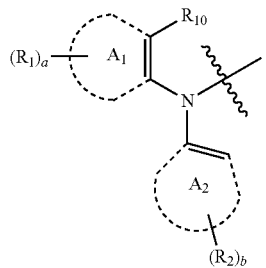

in Formula 1 above has a different structure from the first diarylamino group, the pyrene-based compound of Formula 1 above may be asymmetrical. A thin film including the pyrene-based compound of Formula 1 may be highly amorphous, and thus may have improved electrical stability. Accordingly, an organic light-emitting diode including the pyrene-based compound of Formula 1 may have improved lifetime characteristics.

Therefore, an organic light-emitting diode including the pyrene-based compound of Formula 1 above may have improved electrical characteristics (a low driving voltage, a high current density, and a long lifetime, and the like), and improved color purity.

The pyrene-based compound of Formula 1 may be synthesized by using organic synthesis. A synthesis method of the pyrene-based compound of Formula 1 may be understood by those of ordinary skill in the art from the examples that will be described below.

At least one of the pyrene-based compounds of Formula 1 above may be used between a pair of electrodes of an organic light-emitting diode, for example, in an emission layer of an organic light-emitting diode.

According to another embodiment of the present invention, an organic light-emitting diode includes a first electrode, a second electrode disposed opposite to the first electrode, and an organic layer disposed between the first electrode and the second electrode, wherein the first layer includes at least one of the pyrene-based compounds of Formula 1 described above.

As used herein, "(for example, the organic layer) including at least one pyrene-based compound means that "(the organic layer) including one of the pyrene-based compounds of Formula 1 above, or at least two different pyrene-based compounds of Formula 1 above".

In some embodiments, the organic layer may include only Compound 3 above as the pyrene-based compound. Compound 3 may be in the EML layer of the organic light-emitting diode. In some embodiments, the organic layer may include Compounds 3 and 3 as the pyrene-based compounds of Formula 1 above. in this regard, Compounds 3 and 6 may be in the same layer (for example, both in the ETL) or may be in different layers (for example, in the EML and HTL, respectively).

The organic layer may include at least one layer selected from a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

The term "organic layer" as used herein refers to a single layer and/or a plurality of layers disposed between the first and second electrodes of the organic light-emitting diode.

The organic layer may include an EML, wherein at least one of the pyrene-based compounds of Formula 1 above may be in the EML.

The pyrene-based compound in the EML may serve as a dopant. For example, the pyrene-based compound may serve as a fluorescent dopant. The EML including the pyrene-based compound may emit blue light. In this regard, the EML may further include a host, in addition to the pyrene-based compound.

The host may include at least one of an anthracene-based compound of Formula 400 below and an anthracene-based compound of Formula 401 below:

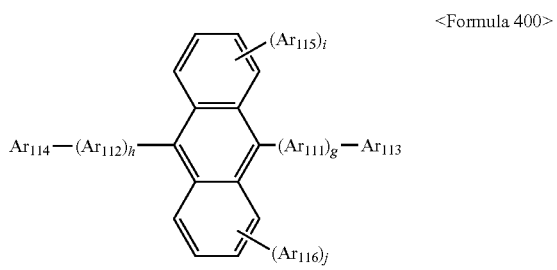

<Formula 400>

In Formula 400, $Ar_{111}$ and $Ar_{112}$ are each independently a substituted or unsubstituted $C_6$-$C_{60}$ arylene group; $Ar_{113}$ to $Ar_{116}$ are each independently a substituted or unsubstituted $C_1$-$C_{10}$ alkyl group, or a substituted or unsubstituted $C_5$-$C_{60}$ aryl group; and g, h, I, and j are each independently an integer from 0 to 4.

In some embodiments, $Ar_{111}$ and $Ar_{112}$ in Formula 400 may be each independently a phenylene group, a naphthylene group, a phenanthrenylene group, or a pyrenylene group; or a phenylene group, a naphthylene group, a phenanthrenylene group, a fluorenyl group, or a pyrenylene group that are substituted with at least one of a phenyl group, a naphthyl group, and an anthryl group.

In Formula 400 above, g, h, I, and j may be each independently 0, 1, or 2.

In some embodiments, $Ar_{113}$ to $Ar_{116}$ in Formula 400 may be each independently one of a $C_1$-$C_{10}$ alkyl group substituted with at least one of a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one of a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a phenyl group, a naphthyl group, an anthryl group, a pyrenyl group, a phenanthrenyl group, and a fluorenyl group; and

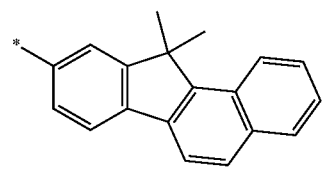 [SMILES: *c1ccc2c(c1)C(C)(C)c1c-2ccc2ccccc12]

but are not limited thereto.

For example, the anthracene-based compound of Formula 400 above may be one of the compounds represented by the following formulae, but is not limited thereto:
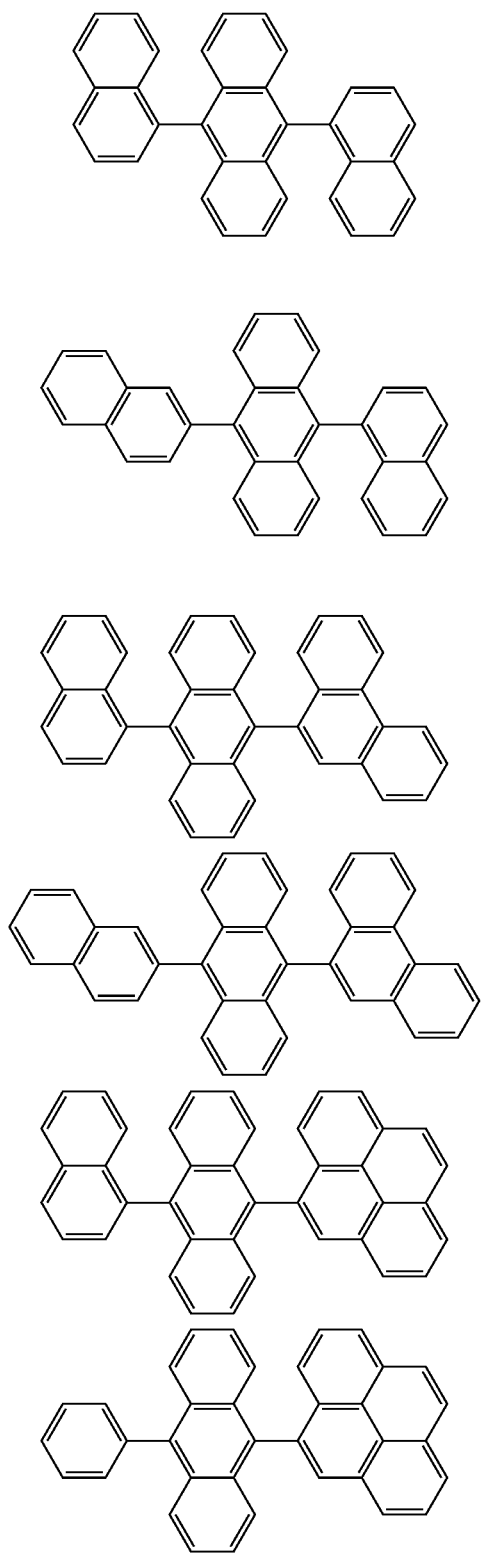
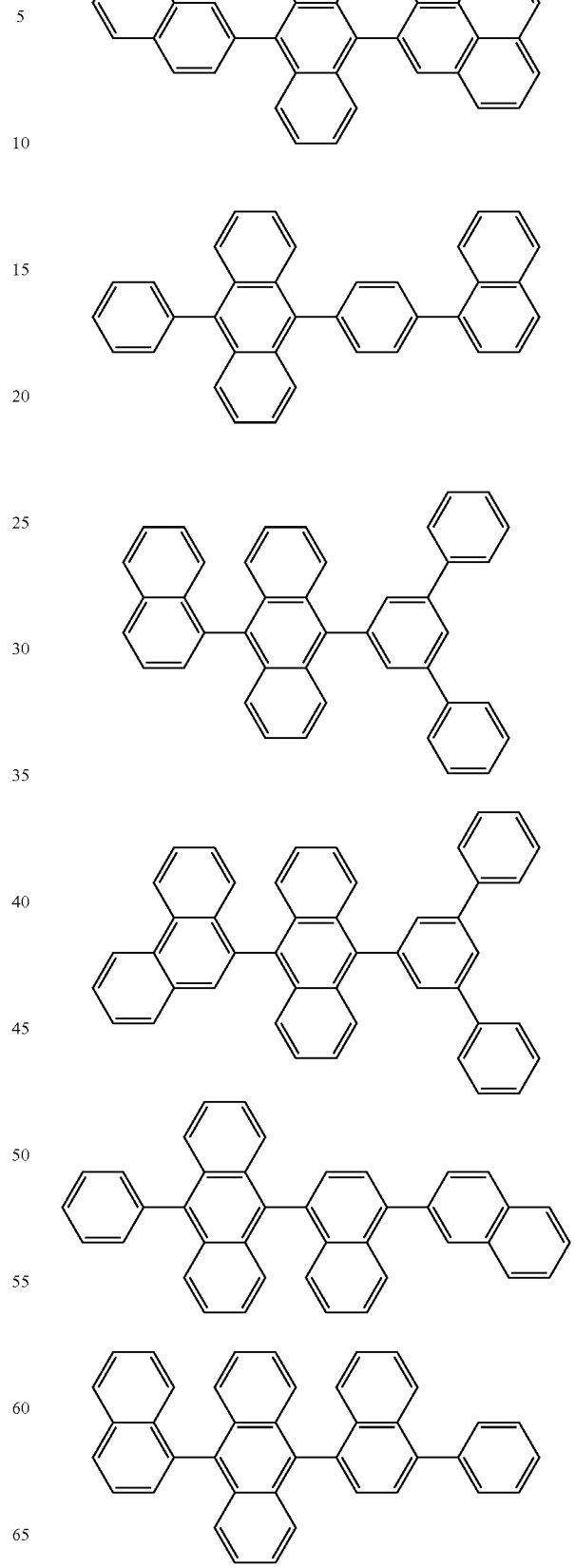

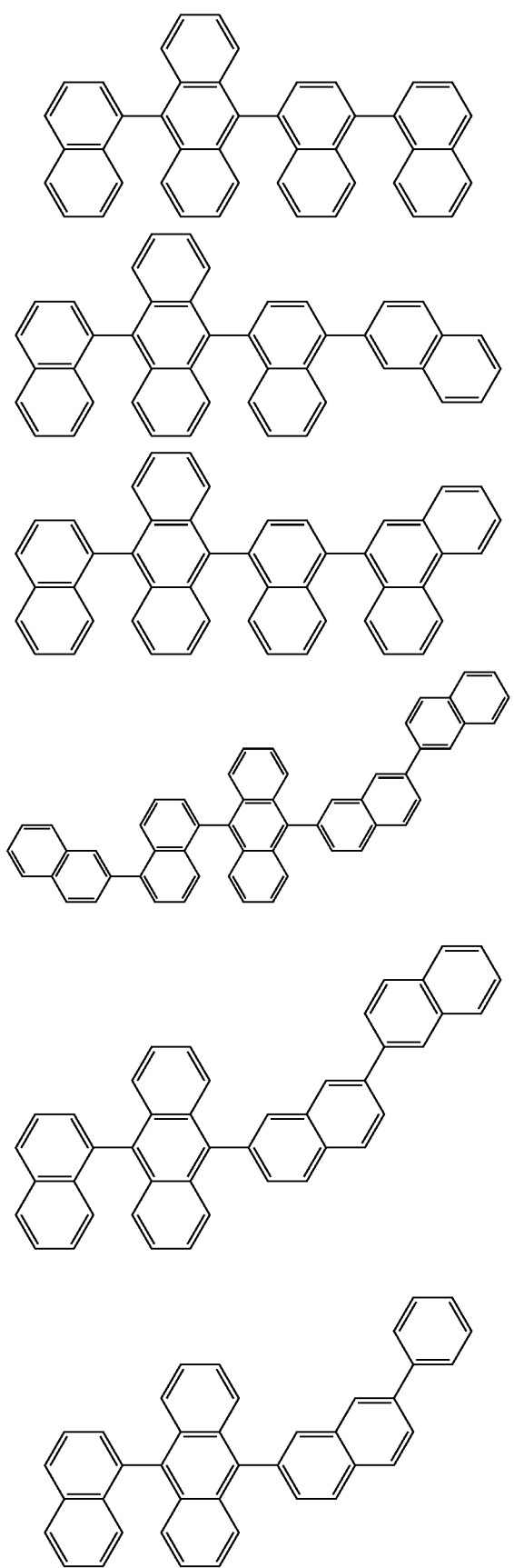
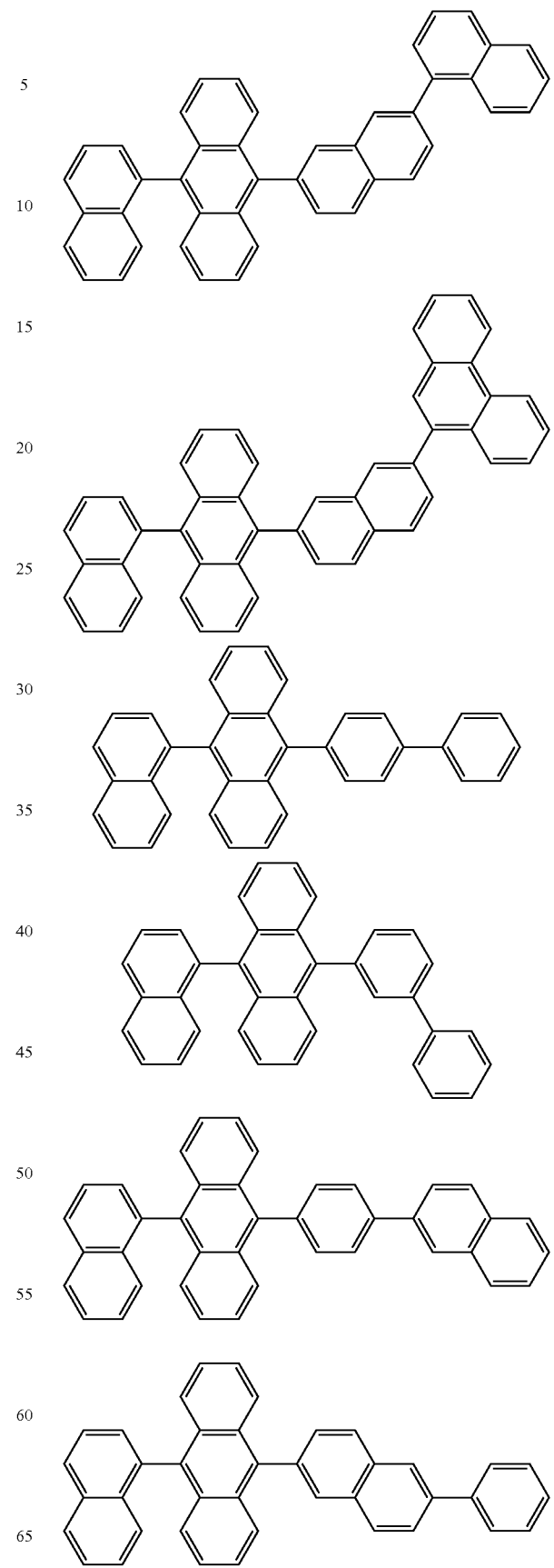

-continued
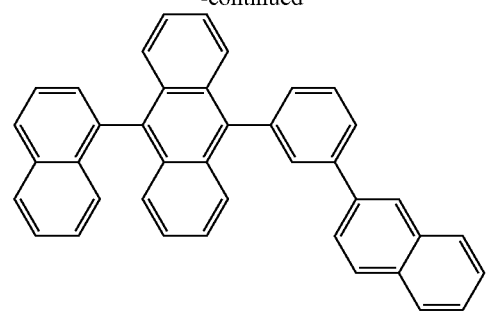
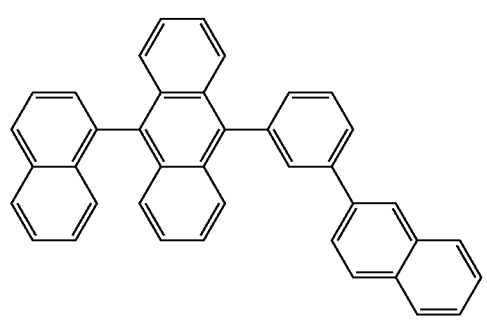
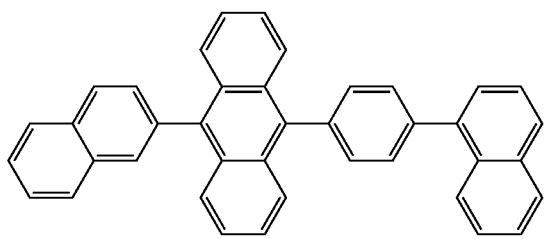
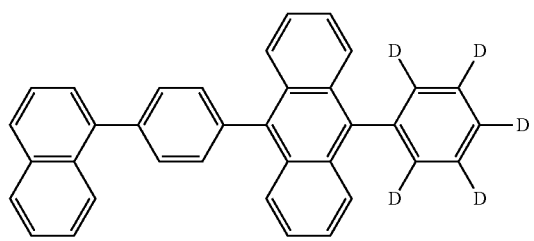
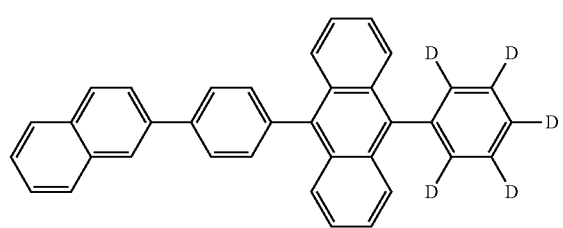
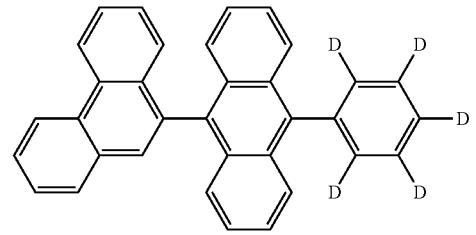
-continued
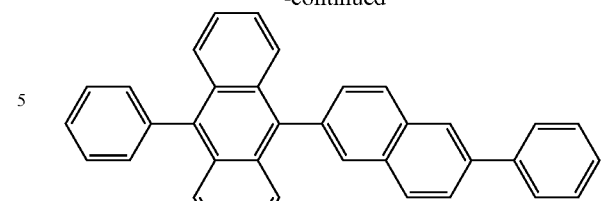
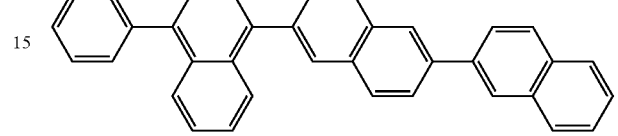
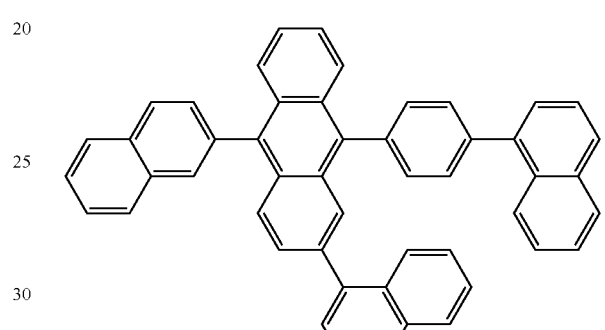
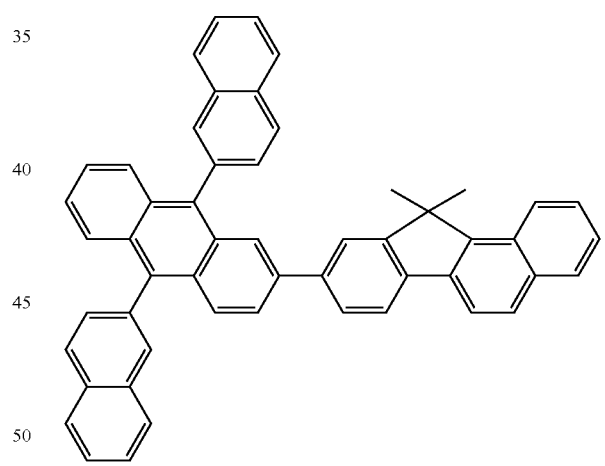
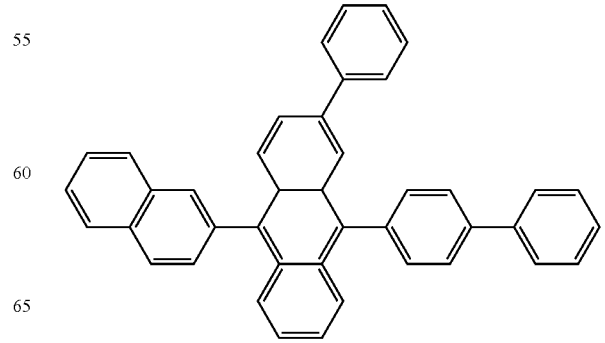

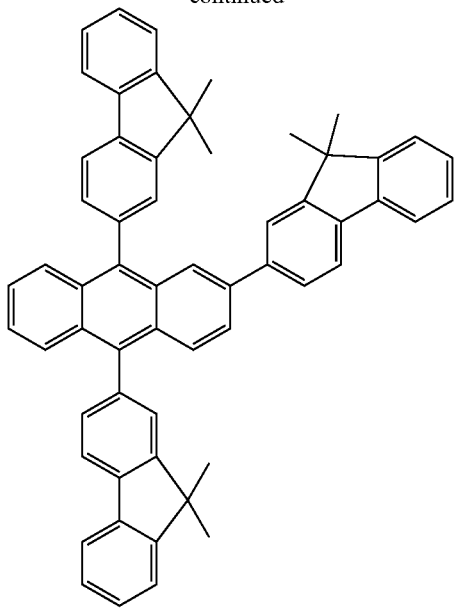

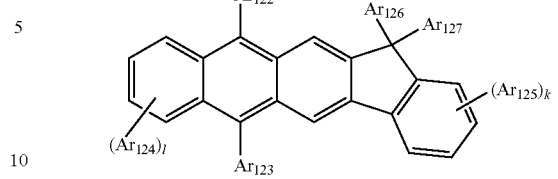

<Formula 401>

$Ar_{122}$ to $Ar_{125}$ in Formula 401 above may be defined as described above in conjunction with $Ar_{113}$ of Formula 400, and thus detailed descriptions thereof will not be provided here.

$Ar_{126}$ and $Ar_{127}$ in Formula 401 above may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

For example, the anthracene compound of Formula 401 above may be one of the compounds represented by the following formulae, but is not limited thereto:

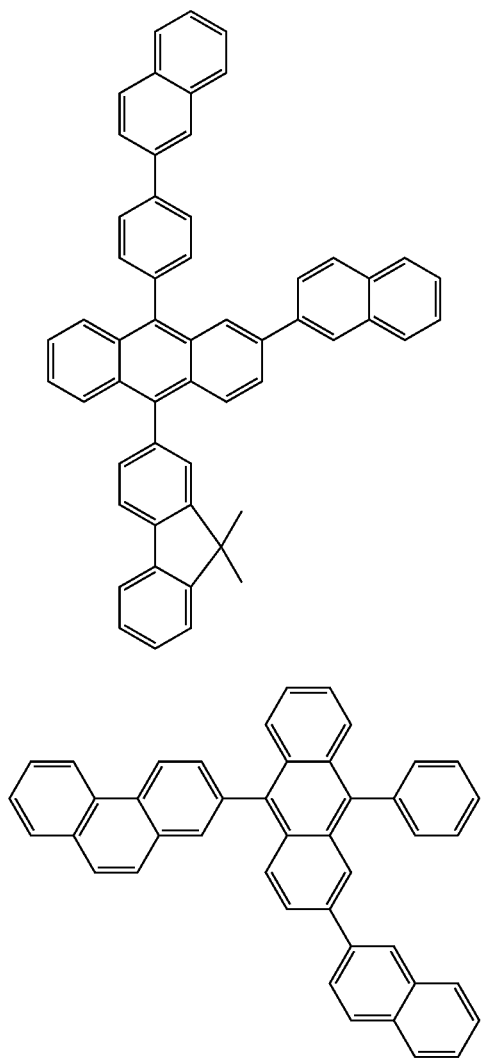

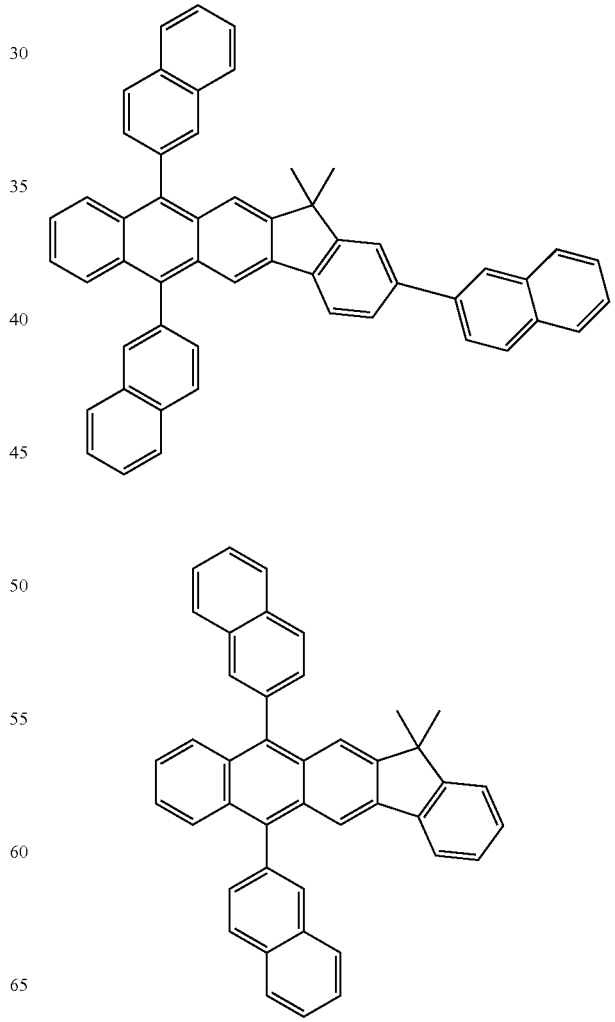

-continued

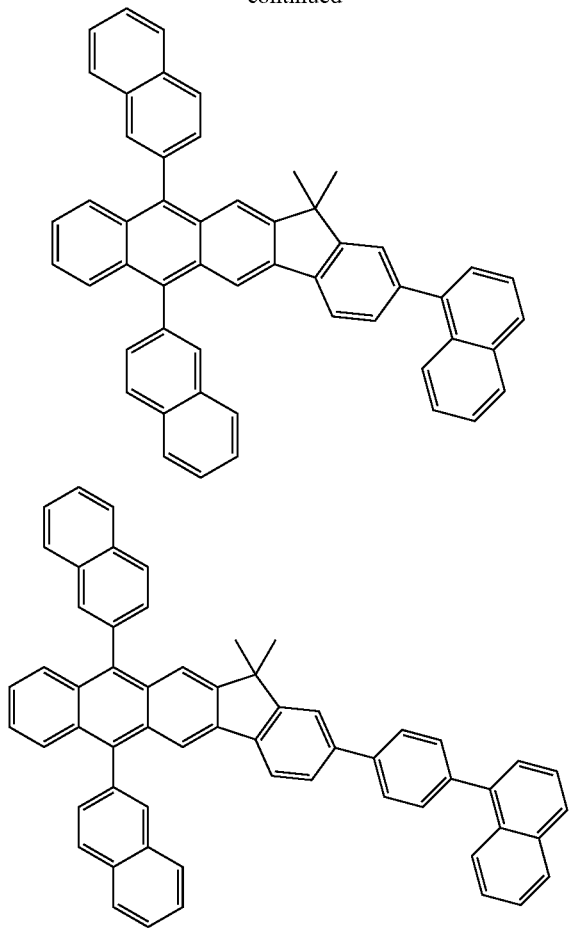

An organic light-emitting diode including the pyrene-based compound of Formula 1 above is able to emit blue light satisfying the sRGB standard, and thus may be applicable in a large-size full-color display (for example, an OLED TV).

Hereinafter, a structure of an organic light-emitting diode according to an embodiment of the present invention and a method of manufacturing the same will now be described with reference to FIG. 1. FIG. 1 is a schematic sectional view of an organic light-emitting diode 10 according to an embodiment of the present invention. A substrate 11 may be any substrate that is used in existing organic light-emitting diodes. In some embodiments the substrate 11 may be a glass substrate or a transparent plastic substrate with strong mechanical strength, thermal stability, transparency, surface smoothness, ease of handling, and water resistance.

A first electrode 13 may be formed by depositing or sputtering a first electrode-forming material on the substrate 11. When the first electrode 13 is an anode, a material having a high work function may be used as the first electrode-forming material to facilitate hole injection. The first electrode 13 may be a reflective electrode, a semi-transmissive electrode, or a transmissive electrode. For example, when the organic light-emitting diode 10 is used in a large display, the first electrode 13 may be a semi-transmissive electrode or a transmissive electrode. Transparent and conductive materials such as ITO, IZO, $SnO_2$, and ZnO may be used to form the first electrode 13. The first electrode 13 may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode 13 may have a single-layer structure or a multi-layer structure including at least two layers. For example, the first electrode 13 may have a three-layered structure of ITO/Ag/ITO, but is not limited thereto.

An organic layer 15 may be disposed on the first electrode 13.

The organic layer 15 may include a hole injection layer (HIL), a hole transport layer (HTL), a buffer layer, an emission layer (EML), an electron transport layer (ETL), and an electron injection layer (EIL).

The HIL may be formed on the first electrode 13 by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range of about 2000 rpm to about 5000 rpm, and a temperature at which heat treatment is performed to remove a solvent after coating may be in the range of about 80° C. to about 200° C. However, the coating conditions are not limited thereto.

A material for forming the HIL may be a known hole injecting material. Non-limiting examples of the hole injecting material are N,N'-diphenyl-N,N'-bis-[4-(phenyl-m-tolyl-amino)-phenyl]-biphenyl-4,4'-diamine, (DNTPD), a phthalocyanine compound such as copper phthalocyanine, 4,4',4''-tris(3-methylphenylphenylamino)triphenylamine (m-MTDATA), TDATA, 2-TNATA, polyaniline/dodecylbenzenesulfonic acid (Pani/DBSA), poly(3,4-ethylenedioxythiophene)/poly(4-styrenesulfonate) (PEDOT/PSS), polyaniline/camphor sulfonic acid (Pani/CSA), and polyaniline)/poly(4-styrenesulfonate (PANI/PSS).

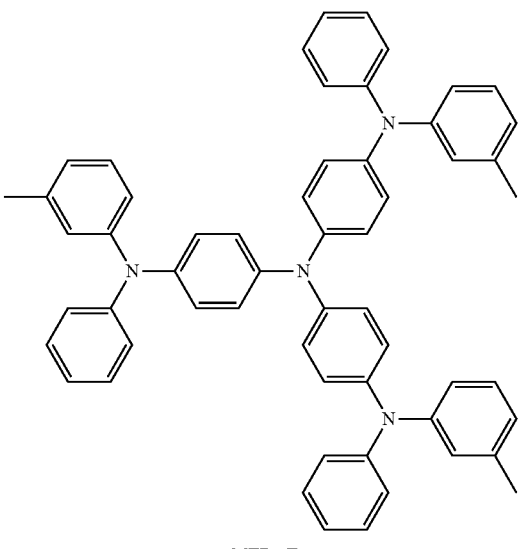

m-MTDATA

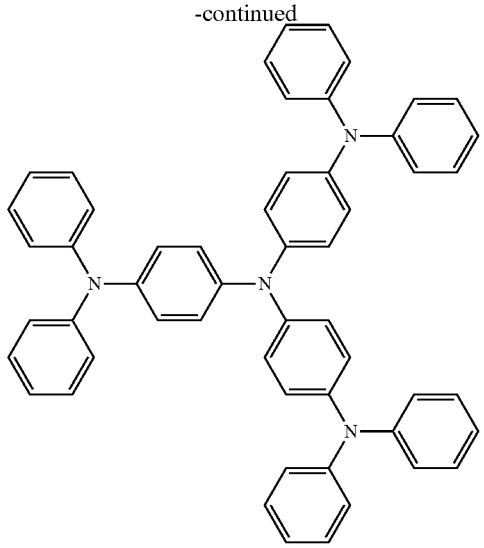

TDATA

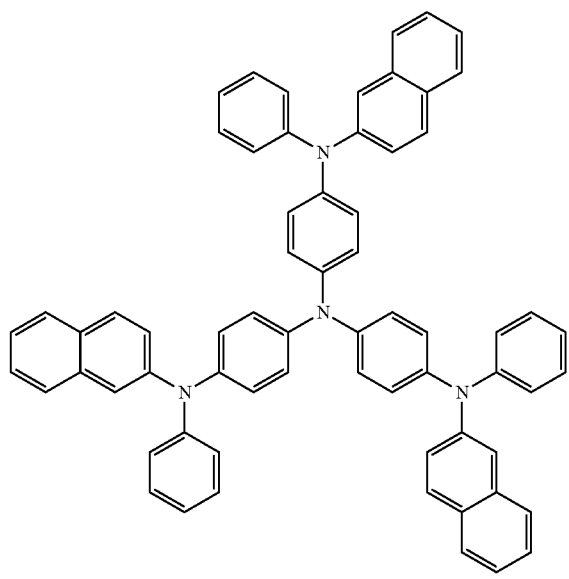

2-TNATA

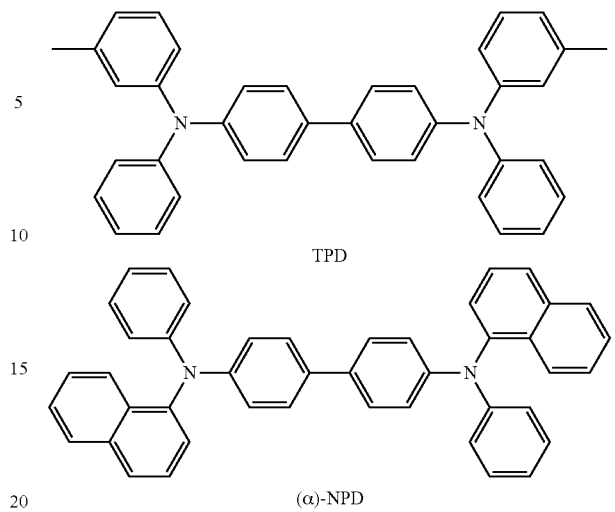

TPD (α)-NPD

The thickness of the HTL may be from about 50 Å to about 2000 Å, and in some embodiments, may be from about 100 Å to about 1500 Å. When the thickness of the HTL is within these ranges, the HTL may have good hole transporting ability without a substantial increase in driving voltage.

The H-functional layer (having both hole injection and hole transport capabilities) may contain at least one material from each group of the hole injection layer materials and hole transport layer materials. The thickness of the H-functional layer may be from about 100 Å to about 10,000 Å, and in some embodiments, may be from about 100 Å to about 1,000 Å. When the thickness of the H-functional layer is within these ranges, the H-functional layer may have good hole injection and transport capabilities without a substantial increase in driving voltage.

In some embodiments, at least one of the HIL, HTL, and H-functional layer may include at least one of a compound of Formula 300 below and a compound of Formula 350 below:

<Formula 300>

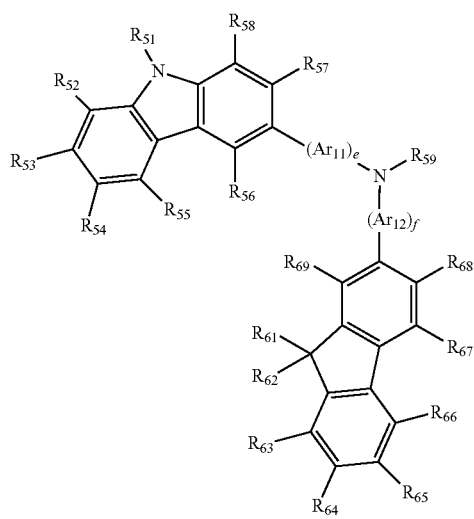

The thickness of the HIL may be about 100 Å to about 10000 Å, and in some embodiments, may be from about 100 Å to about 1000 Å. When the thickness of the HIL is within these ranges, the HIL may have good hole injecting ability without a substantial increase in driving voltage.

Then, a HTL may be formed on the HIL by using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

Non-limiting examples of suitable known hole transport materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4''-tris(N-carbazolyl)triphenylamine (TCTA), and α-NPD.

<Formula 350>

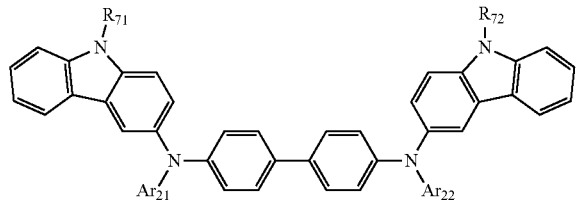

In Formulae 300 and 350, $Ar_{11}$, $Ar_{12}$, $Ar_2$, and $Ar_{22}$ may be each independently a substituted or unsubstituted $C_6$-$C_{60}$ arylene group. When $Ar_{11}$, $Ar_{12}$, $Ar_{21}$ or $Ar_{22}$ is a substituted $C_6$-$C_{60}$arylene group, at least one substituent of the substituted $C_6$-$C_{60}$arylene group may be selected from, a deuterium atom, a halogen atom, a hydroxy group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group and a $C_1$-$C_{10}$alkoxy group;

a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group; and a phenyl group, a naphthyl group, a fluorenyl group, a phenanthrenyl group, an anthryl group, a triphenylenyl group, a pyrenyl group, a chrysenyl group, an imidazolyl group, an imidazolinyl group, an imidazopyridinyl group, an imidazopyrimidinyl group, a pyridinyl group, a pyrazinyl group, a pyrimidinyl group, and an indolyl group, substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, $C_1$-$C_{10}$alkyl group, and a $C_1$-$C_{10}$alkoxy group.

In some embodiments, $Ar_{11}$, $A_{12}$, $Ar_{21}$, and $Ar_{22}$ may be each independently selected from a substituted or unsubstituted phenylene group, a substituted or unsubstituted pentalenylene group, a substituted or unsubstituted indenylene group, a substituted or unsubstituted naphthylene group, a substituted or unsubstituted azulenylene group, a substituted or unsubstituted heptalenylene group, a substituted or unsubstituted indacenylene group, a substituted or unsubstituted acenaphthylene group, a substituted or unsubstituted fluorenylene group, a substituted or unsubstituted phenalenylene group, a substituted or unsubstituted phenanthrenylene group, a substituted or unsubstituted anthrylene group, a substituted or unsubstituted fluoranthenylene group, a substituted or unsubstituted triphenylenylene group, a substituted or unsubstituted pyrenylene group, a substituted or unsubstituted chrysenylen group, a substituted or unsubstituted naphthacenylene group, a substituted or unsubstituted picenylene group, a substituted or unsubstituted perylenylene group, a substituted or unsubstituted pentacenylene group, and a substituted or unsubstituted hexacenylene group.

For example, $Ar_{11}$, $Ar_{12}$, $Ar_{21}$, and $Ar_{22}$ may be each independently a substituted or unsubstituted phenylene group, a substituted or unsubstituted naphthylene group, a substituted or unsubstituted fluorenylene group, or a substituted or unsubstituted phenanthrenylene group.

In Formula 300, e and f may be each independently an integer from 0 to 5, for example, may be 0, 1, or 2. For example, e may be 1, and f may be 0, but not limited thereto.

In Formulae 300 and 350 above, $R_{51}$ to $R_{58}$, $R_{61}$ to $R_{69}$, and $R_{71}$ and $R_{72}$ may be each independently selected from, a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$alkynyl group, a substituted or unsubstituted $C_1$-$C_{60}$ alkoxy group, a substituted or unsubstituted $C_3$-$C_{60}$ cycloalkyl group, a substituted or unsubstituted $C_6$-$C_{60}$ aryl group, a substituted or unsubstituted $C_6$-$C_{60}$ aryloxy group, and a substituted or unsubstituted $C_6$-$C_{60}$ arylthio group. In some embodiments, $R_{51}$ to $R_{58}$, $R_{61}$ to $R_{69}$, $R_{71}$, and $R_{72}$ may be each independently one of a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be one of a phenyl group, a naphthyl group, an anthryl group, a biphenyl group, a pyridinyl group; and a phenyl group, a naphthyl group, an anthryl group, a biphenyl group, and a pyridinyl group that are substituted with at least one of a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment the compound of Formula 300 may be a compound represented by Formula 300A below:

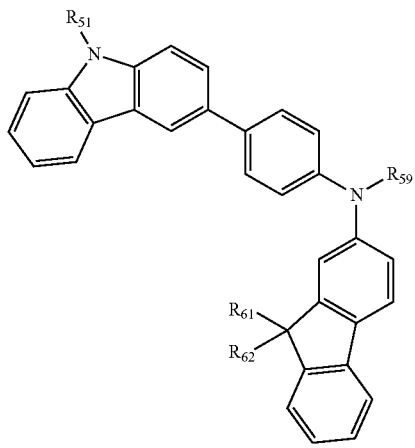
<Formula 300A>
In Formula 300A, $R_{51}$, $R_{60}$, $R_{61}$, and $R_{59}$ may be as defined above.
In some non-limiting embodiments, at least one of the HIL, HTL, and H-functional layer may include at least one of compounds represented by Formulae 301 to 320 below:
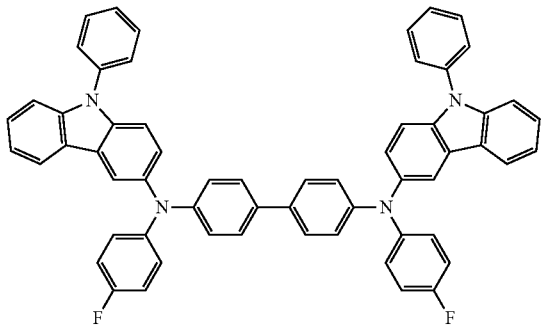
303
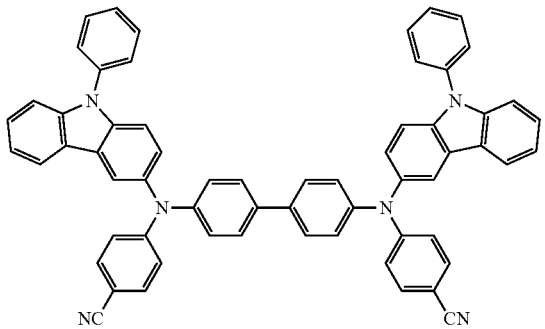
304
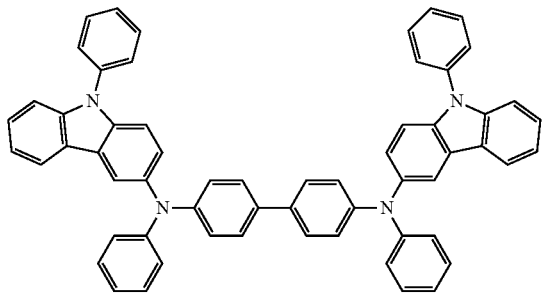
301
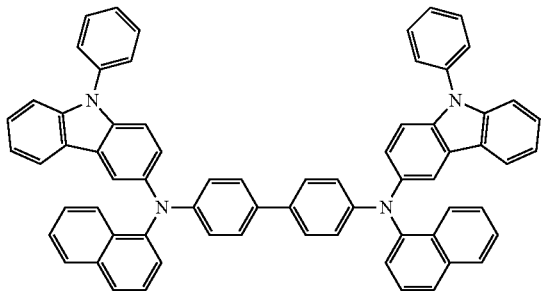
305
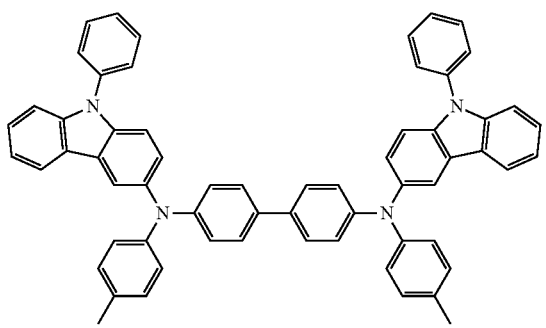
302
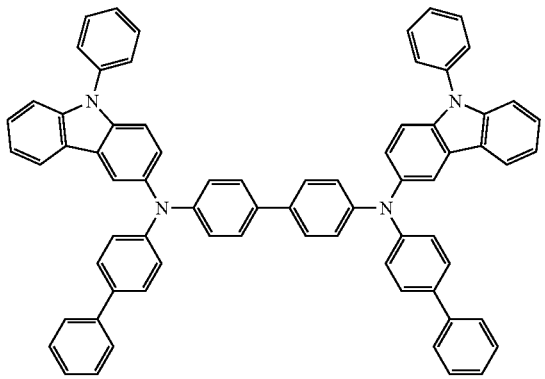
306

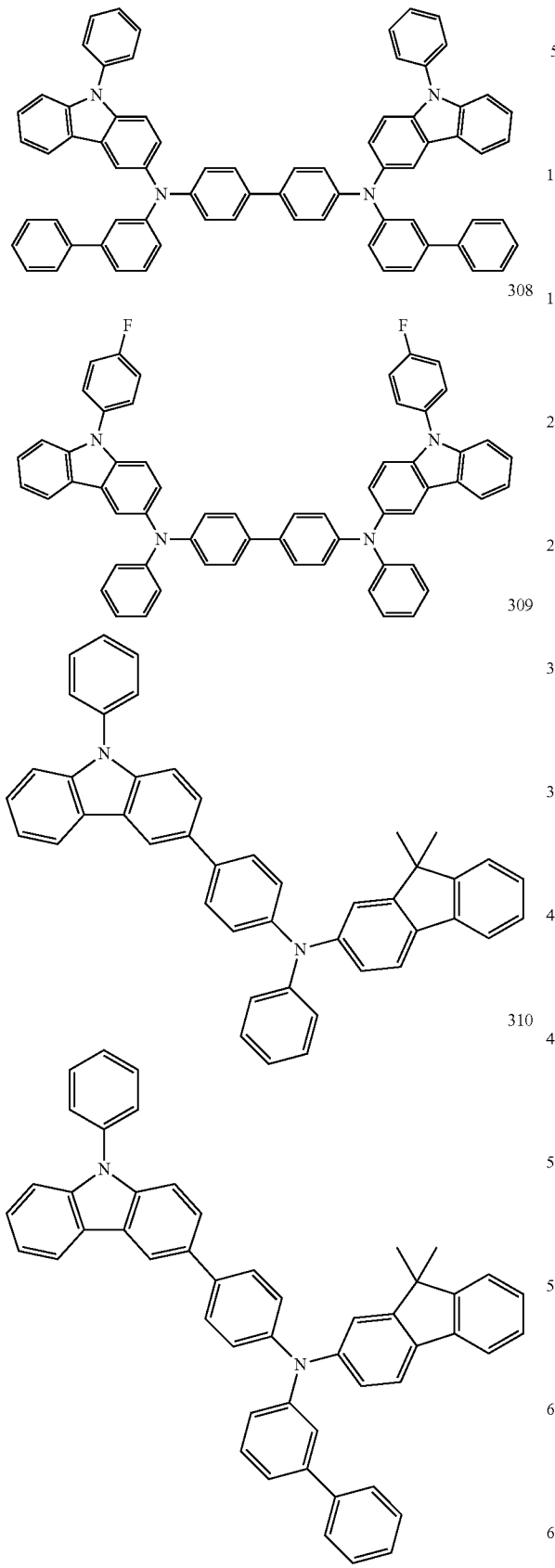
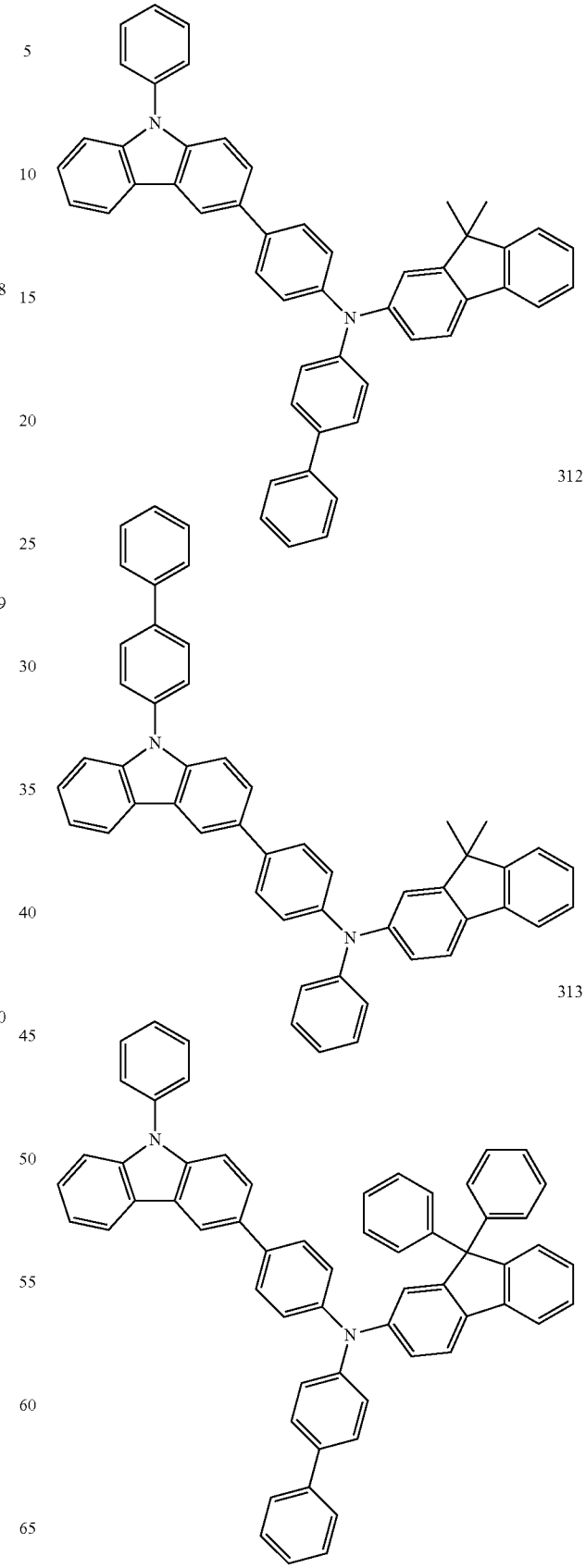

314
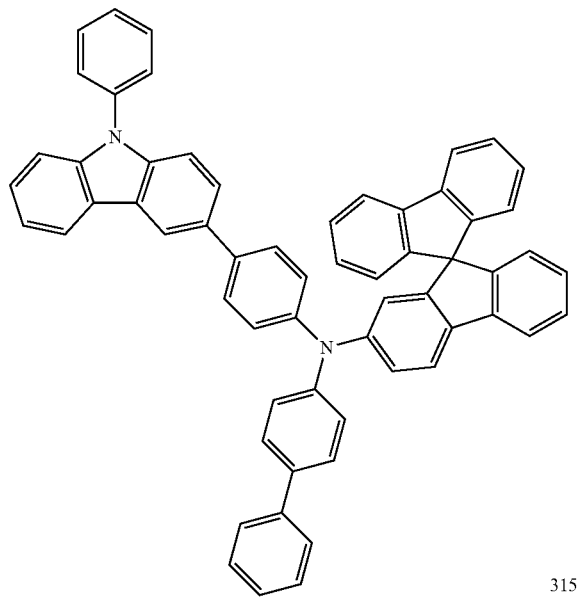
315
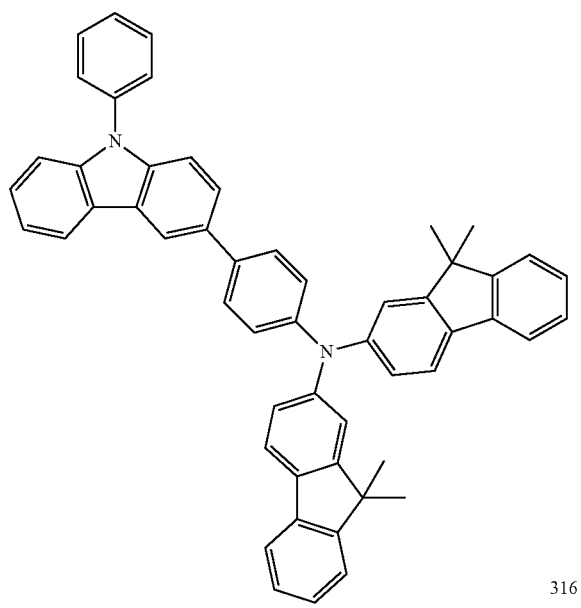
316
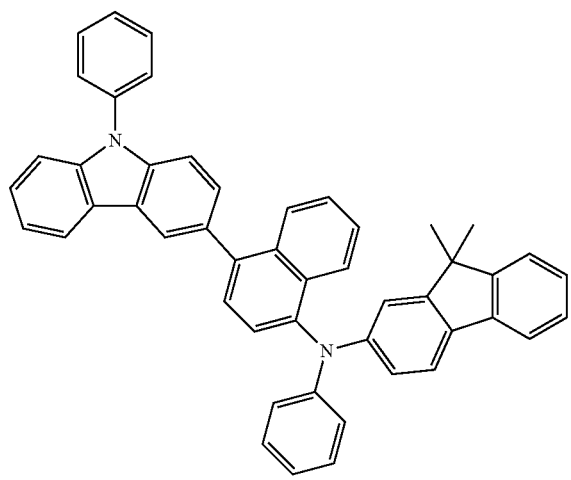
317
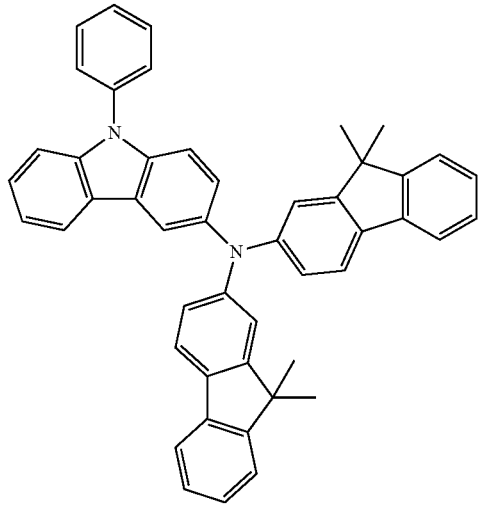
318
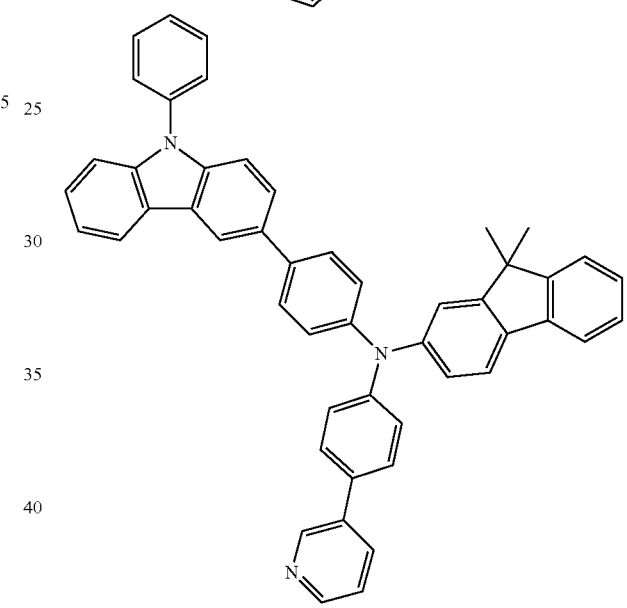
319
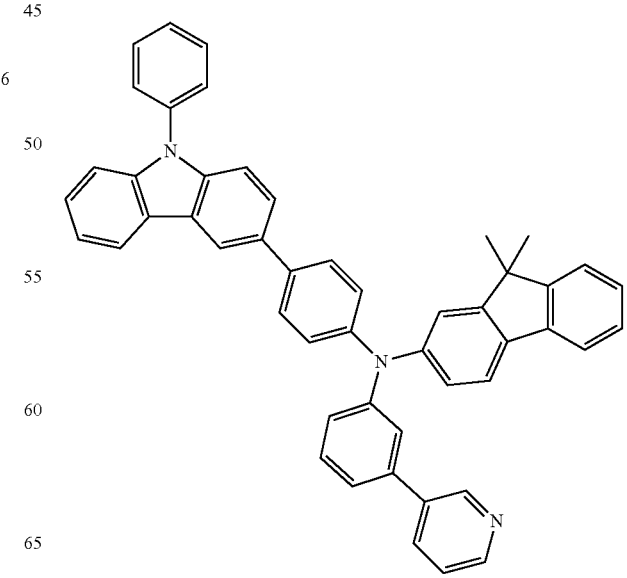

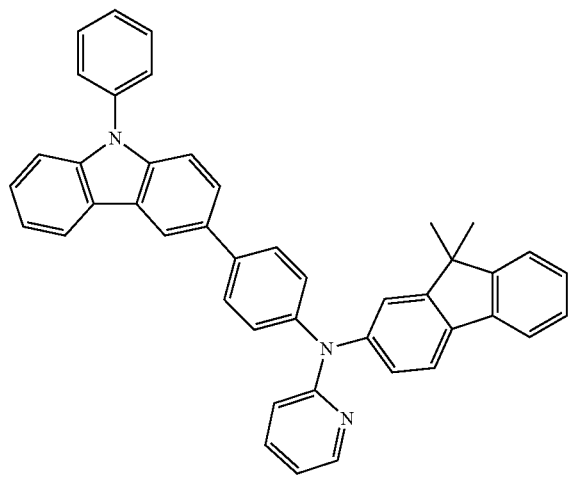

At least one of the HIL, HTL, and H-functional layer may further include a charge-generating material for improved layer conductivity, in addition to a known hole injecting material, hole transport material, and/or material having both hole injection and hole transport capabilities as described above.

The charge-generating material may be, for example, a p-dopant. The p-dopant may be one of quinine derivatives, metal oxides, and compounds with a cyano group, but are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

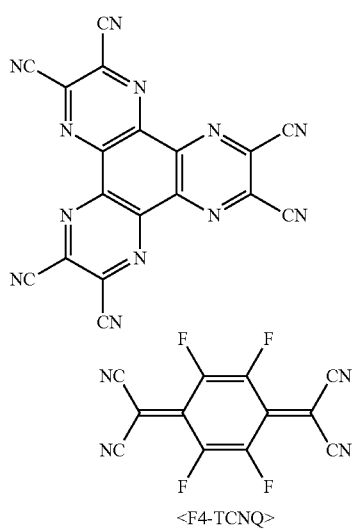

When the hole injection layer, hole transport layer, or H-functional layer further includes a charge-generating material, the charge-generating material may be homogeneously dispersed or inhomogeneously distributed in the layer.

A buffer layer may be disposed between at least one of the HIL, HTL, and H-functional layer, and the EML. The buffer layer may compensate for an optical resonance distance of light according to a wavelength of the light emitted from the EML, and thus may increase efficiency. The butter layer may include any hole injecting material or hole transporting material that are widely known. In some other embodiments, the buffer layer may include the same material as one of the materials included in the HIL, HTL, and H-functional layer that underlie the buffer layer.

Then, an EML may be formed on the HTL, H-functional layer, or buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may include at least one of the pyrene-based compounds of Formula 1.

The pyrene-based compound in the EML may serve as a dopant, for example, as a blue fluorescent dopant. In this regard, the EML may further include a host, in addition to the pyrene-based compound.

Non-limiting example of the host are $Alq_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (see a formula below), and Compounds 501 to 509 below.

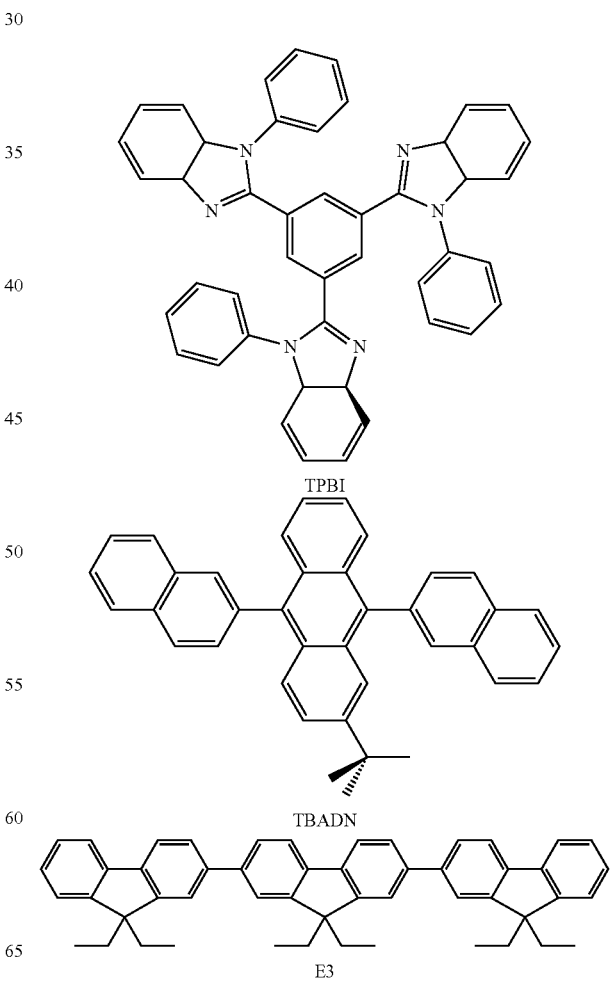

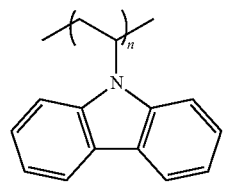
PVK
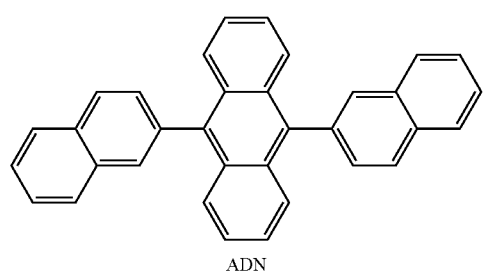
ADN
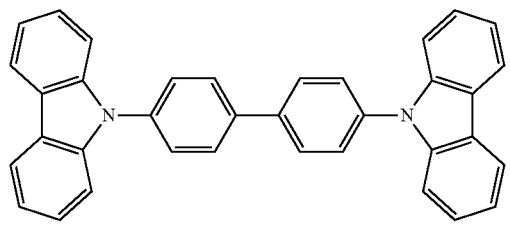
CBP
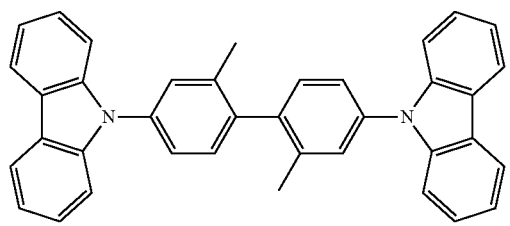
dmCBP
501
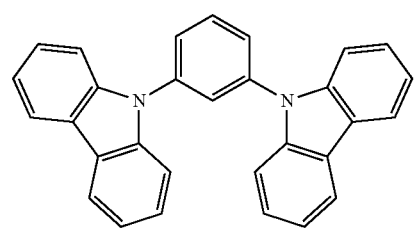
502
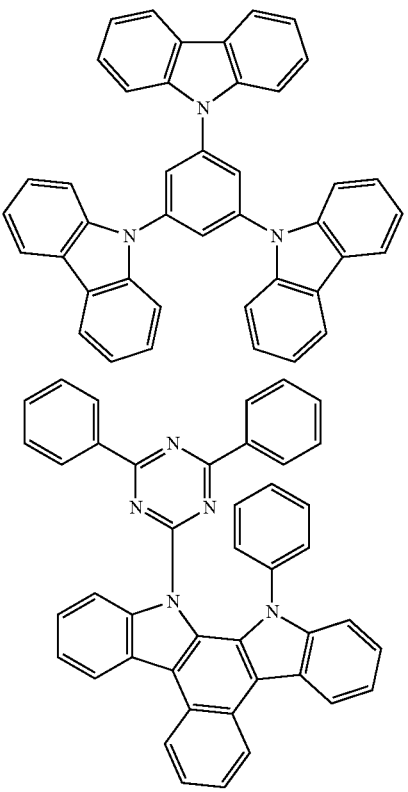
503
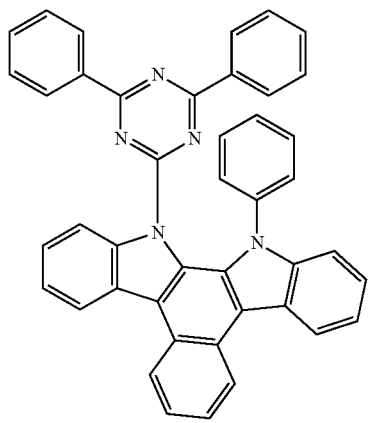
504
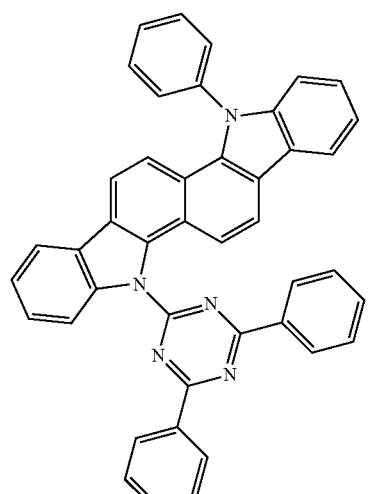
505
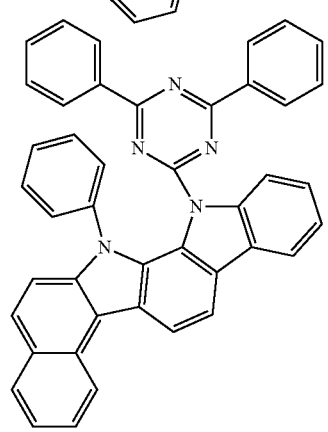

91
-continued

506

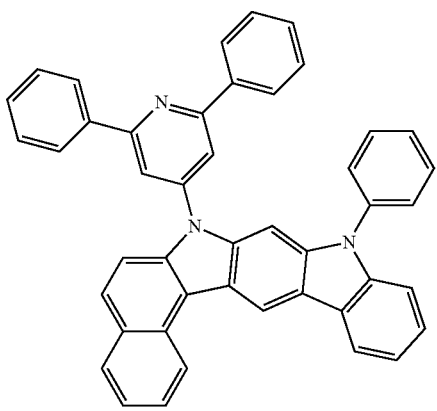

507

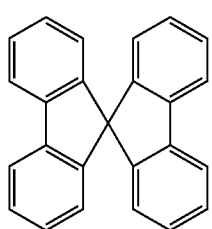

508

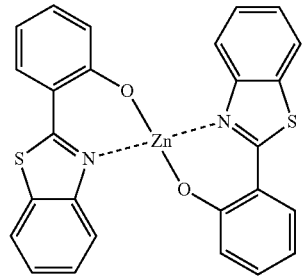

92
-continued

509

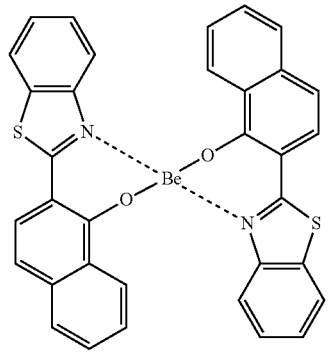

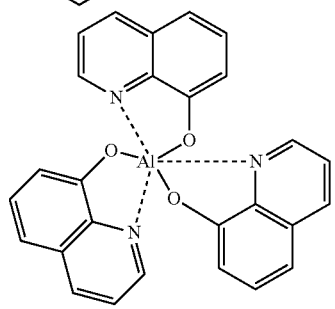

Alq₃

In some embodiments, the host for the EML may include at least one of an anthracene-based compound of Formula 400 above and an anthracene-based compound of Formula 401 above:

The organic light-emitting diode may include a blue subpixel emitting blue light, a green subpixel emitting green light, and a red subpixel emitting red light. The blue subpixel may include a blue EML emitting blue light, wherein the blue EML may include the pyrene-based compound represented by Formula 1 above. In some embodiments, the organic light-emitting diode may include a red emission layer, a green emission layer, and/or a blue emission layer that are stacked upon one another to emit white light. The organic light-emitting diode may have any of a variety of structures not limited thereto.

The blue EML may further include at least one of compounds represented by the following formulae as a blue dopant, but not limited thereto.

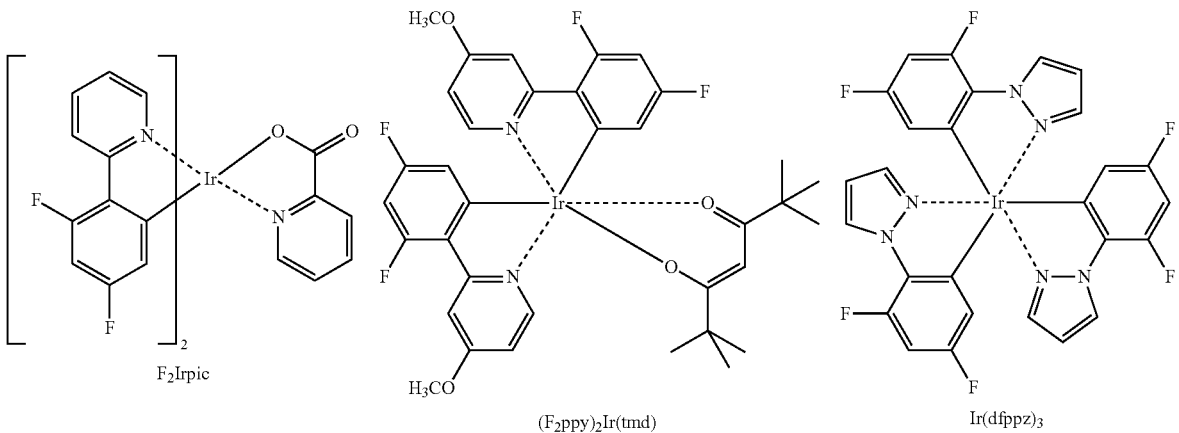

F₂Irpic         (F₂ppy)₂Ir(tmd)         Ir(dfppz)₃

-continued
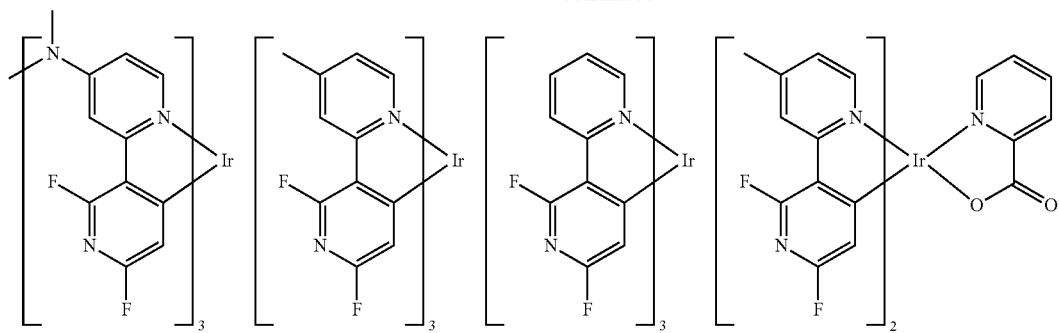
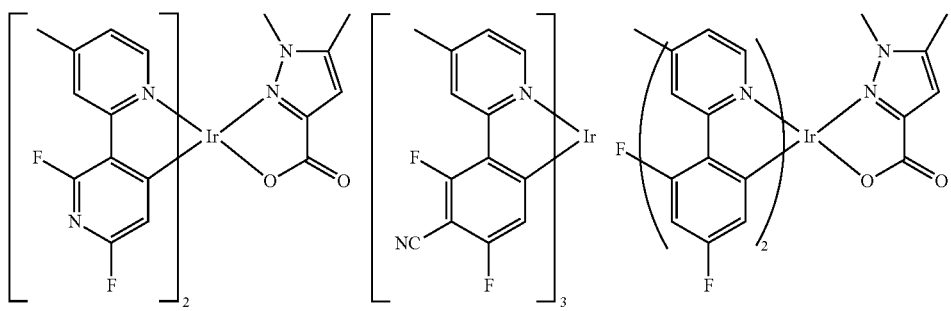
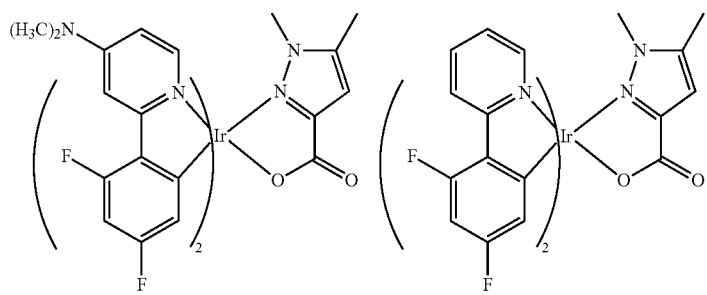
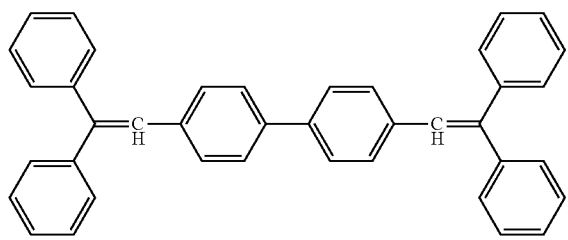
DPVBi
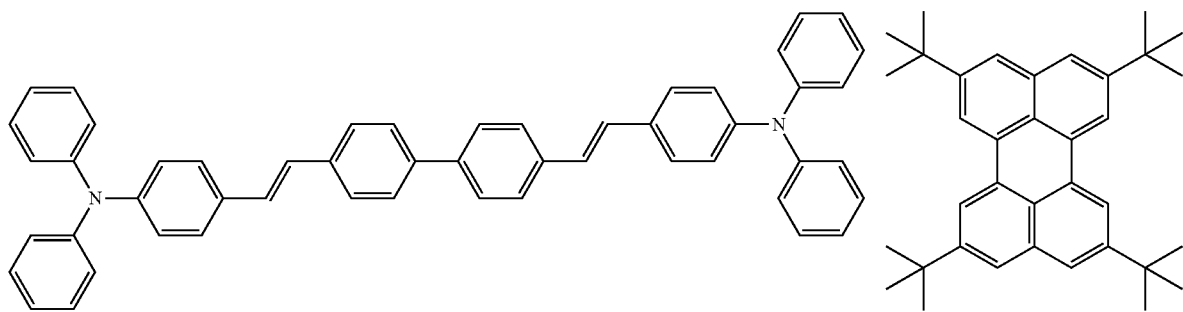
DPAVBi
TBPe In some embodiments, the red EML of the red subpixel may include at least one of compounds represented by the following formulae as a red dopant, but not limited thereto. For example, the red dopant may be DCM or DCJTB, which will be described later.
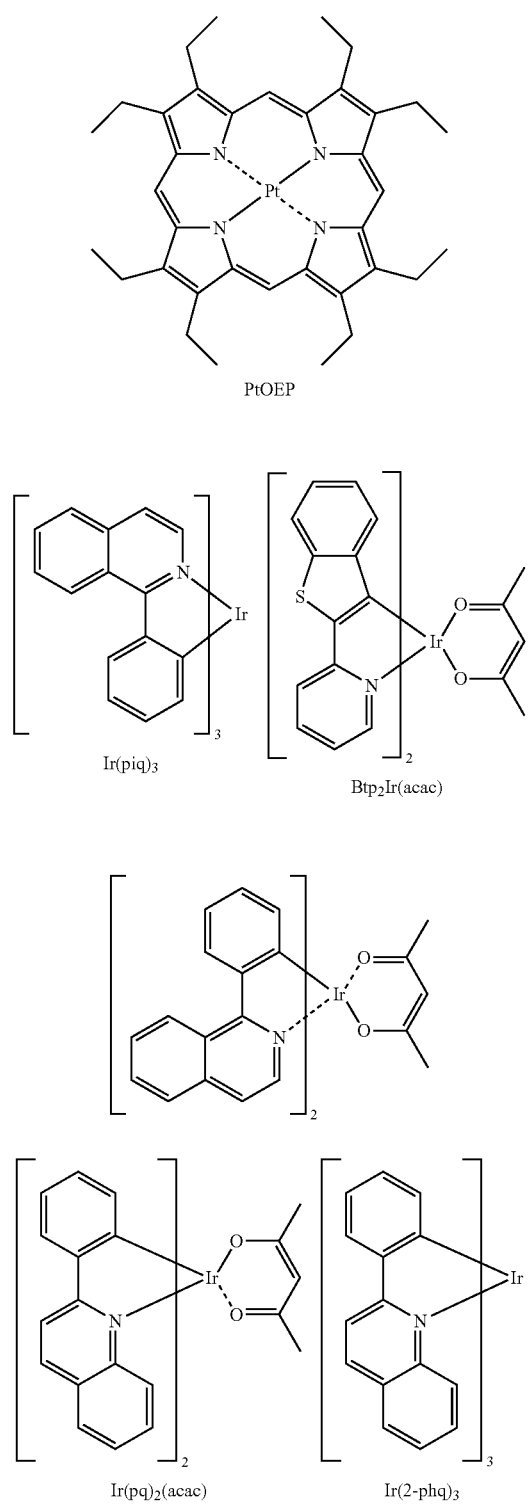
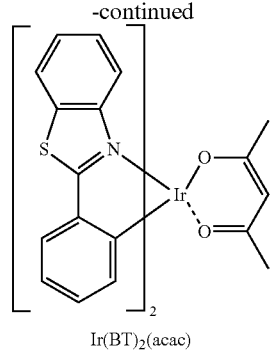
Ir(BT)₂(acac)
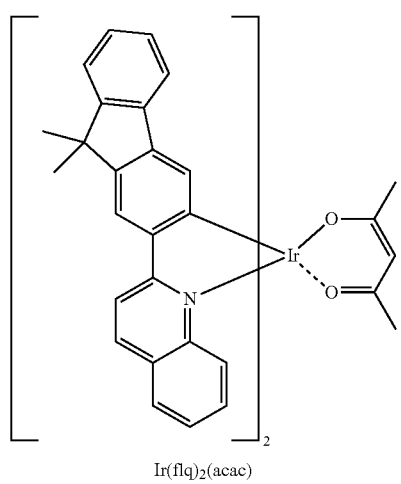
Ir(flq)₂(acac)
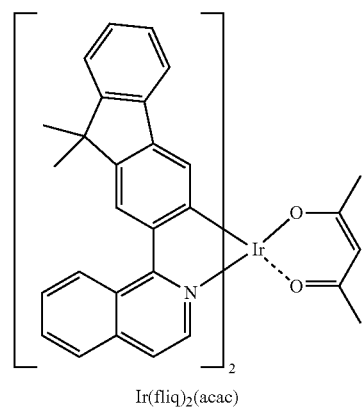
Ir(fliq)₂(acac)
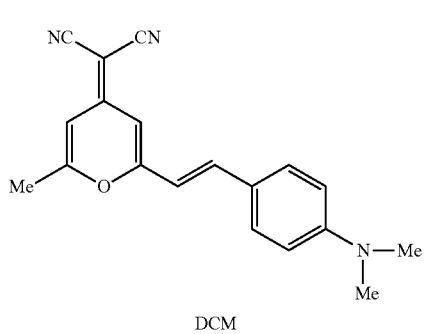
DCM -continued

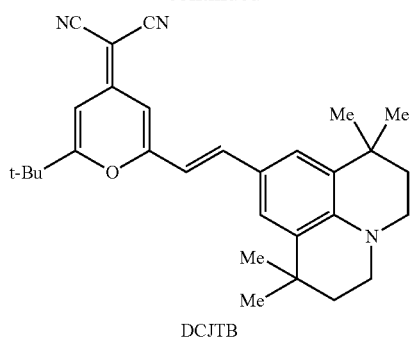 [SMILES: CC(C)(C)C1=CC(=C(C#N)C#N)C=C(/C=C/c2cc3c4c(c2)C(C)(C)CCN4CCC3(C)C)O1]
DCJTB

In some embodiments, the green EML of the green subpixel may include at least one of compounds represented by the following formulae as a green dopant, but not limited thereto. For example, the green dopant may be C545T represented below.

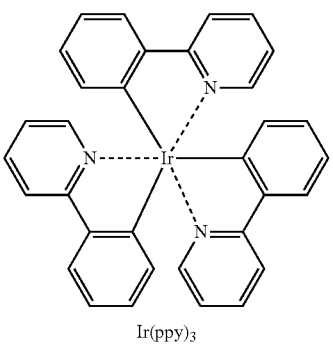
Ir(ppy)₃

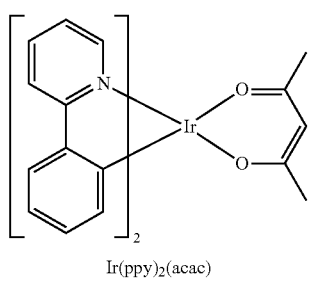
Ir(ppy)₂(acac)

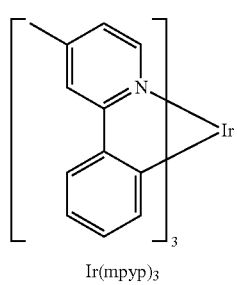
Ir(mpyp)₃

-continued

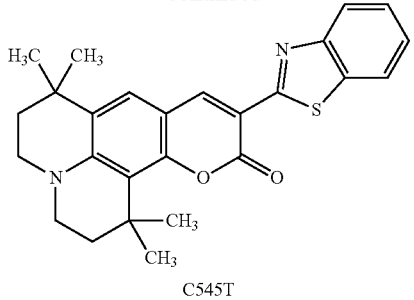
C545T

Non-limiting examples of the dopant that may be used in the EML are complexes represented by the following formulae.

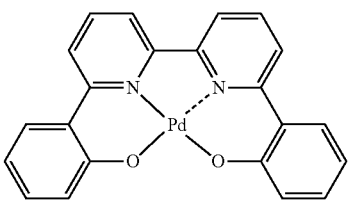
D1

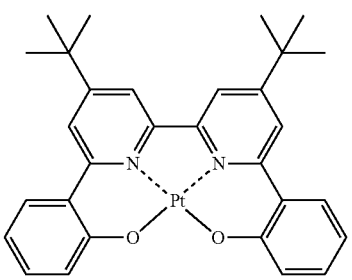
D2

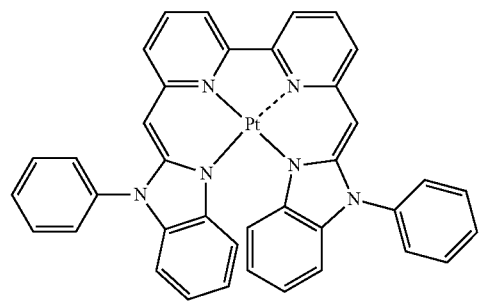
D3

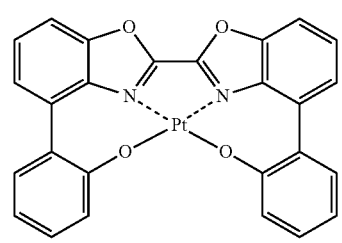
D4

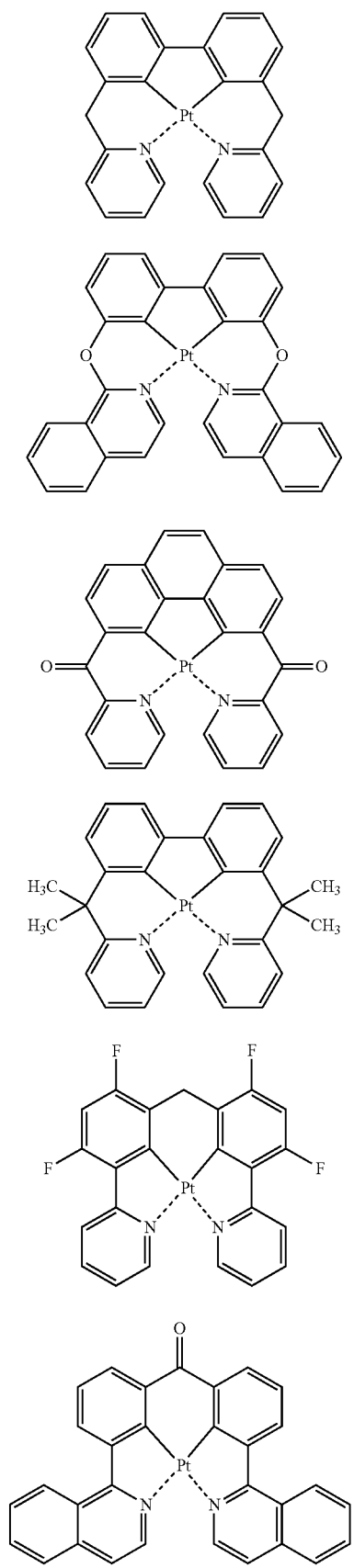

D16 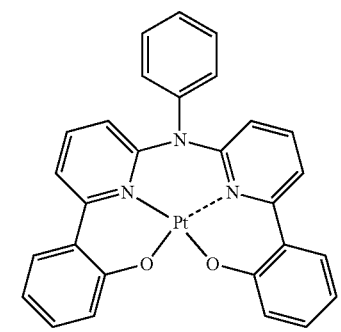
D17 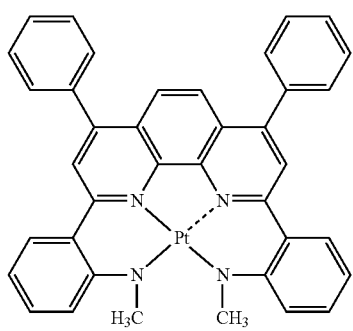
D18 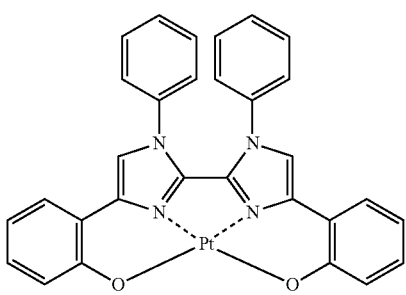
D19 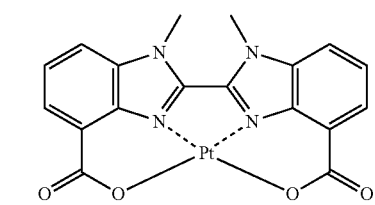
D20 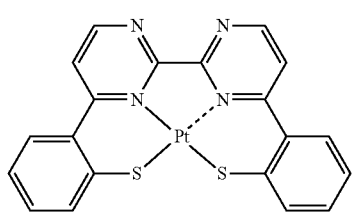
D21 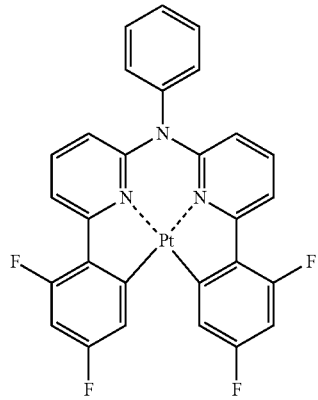
D22 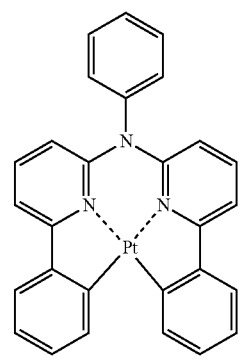
D23 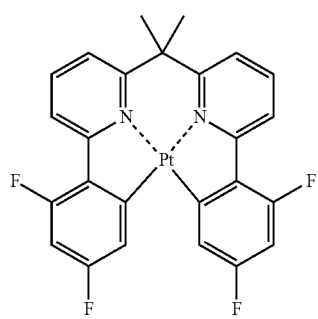
D24 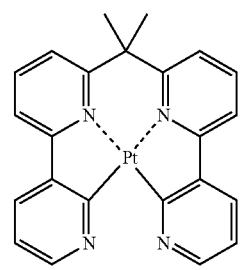
D25 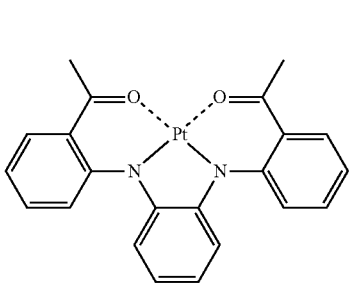

-continued
D26
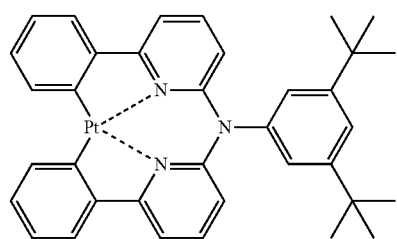
D27
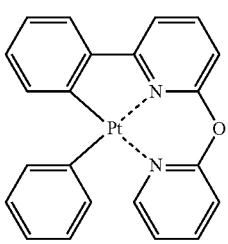
D28
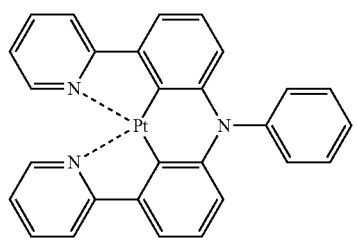
D29
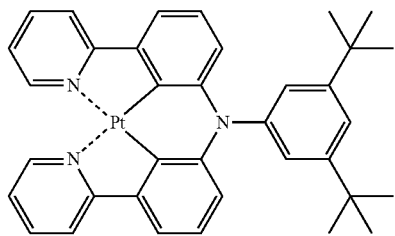
D30
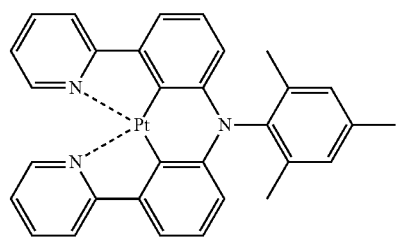
D31
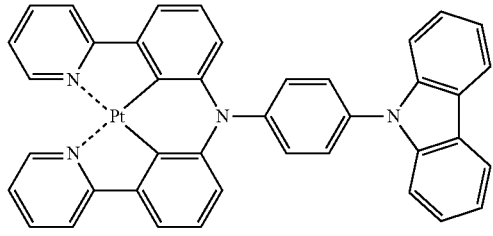
-continued
D32
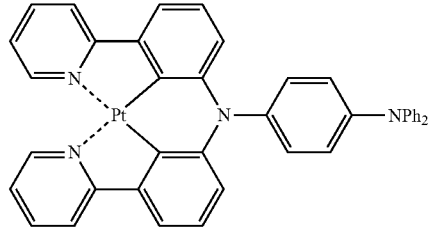
D33
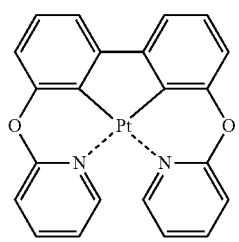
D34
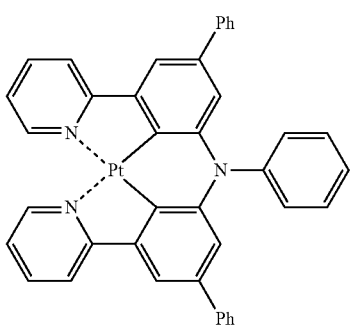
D35
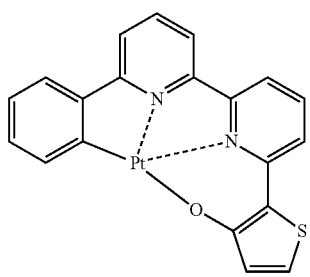
D36
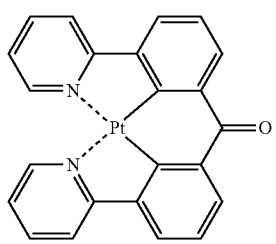

D37
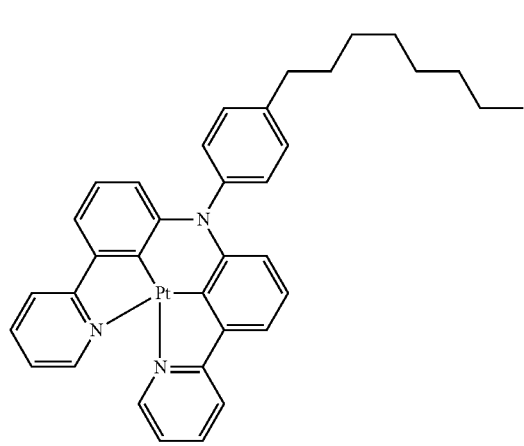
D38
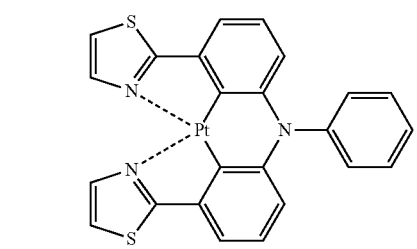
D39
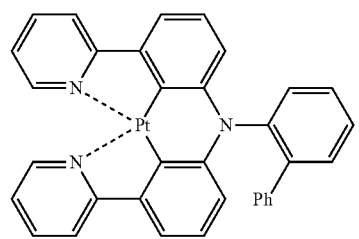
D40
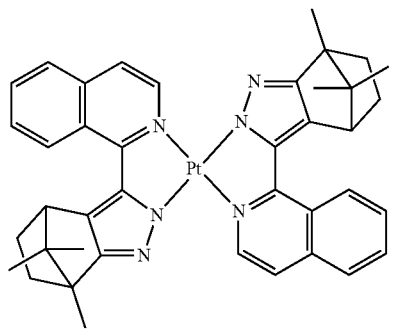
D41
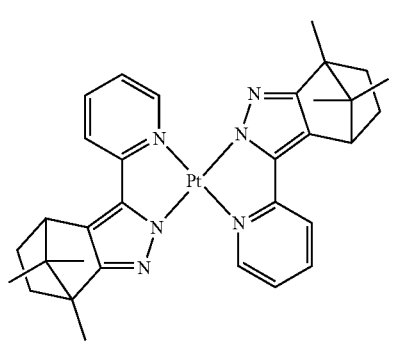
D42
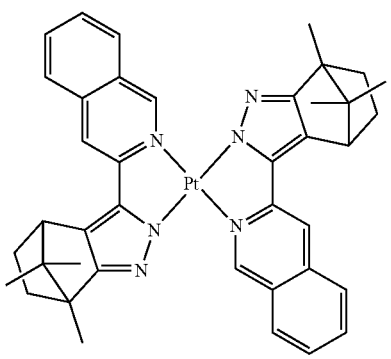
D43
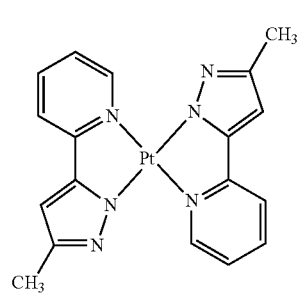
D44
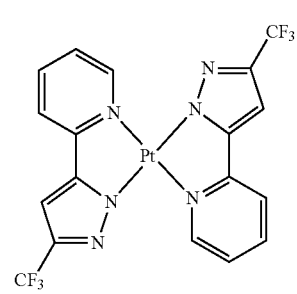
D45
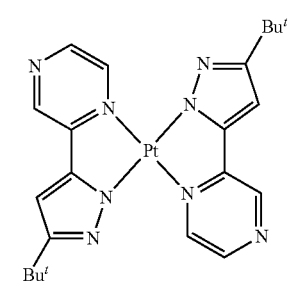
D46
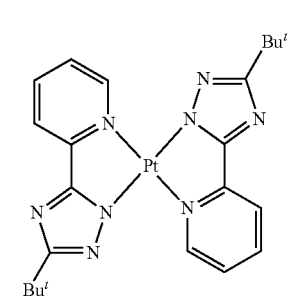

-continued

D47
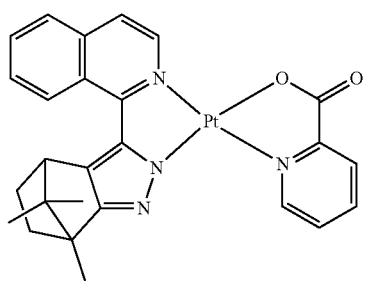

D48
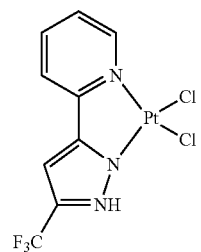

D49
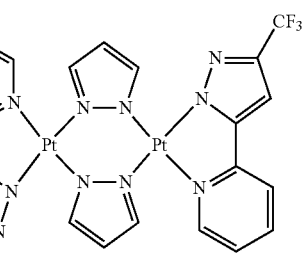

D50
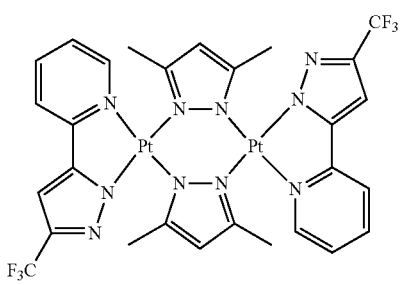

Non-limiting examples of the dopant that may be used in the EML are Os complexes represented by the following formulae.

Os(fppz)$_2$(CO)$_2$

-continued

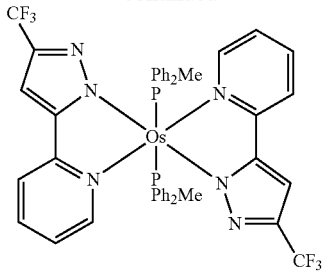
Os(fppz)$_2$(PPh$_2$Me)$_2$

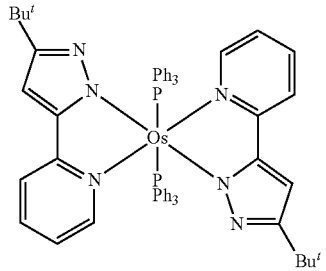
Os(bppz)$_2$(PPh$_3$)$_2$

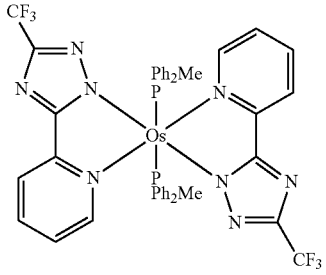
Os(fptz)$_2$(PPh$_2$Me)$_2$

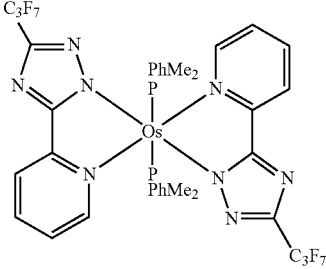
Os(hptz)$_2$(PPh$_2$Me$_2$)$_2$

When the EML includes both a host and a dopant, the amount of the dopant may be from about 0.01 to about 15 parts by weight based on 100 parts by weight of the host. However, the amount of the dopant is not limited to this range.

The thickness of the EML may be about 100 Å to about 1000 Å, and in some embodiments, may be from about 200 Å to about 600 Å. When the thickness of the EML is within these ranges, the EML may have good light emitting ability without a substantial increase in driving voltage.

le;.3qThen, an ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL. A material for forming the ETL may be any known material that can stably transport electrons injected from an electron injecting electrode (cathode). Non-limiting examples of materials for forming the ETL are a quinoline derivative, such as tris(8-quinolinorate)aluminum (Alq$_3$), TAZ, BAlq, beryllium bis(benzoquinolin-10-olate (Bebq$_2$), 9,10-di(naphthalene-2-yl)anthracene (ADN), Compound 201, and Compound 202, but are not limited thereto.

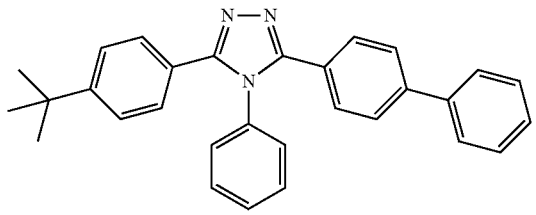

TAZ

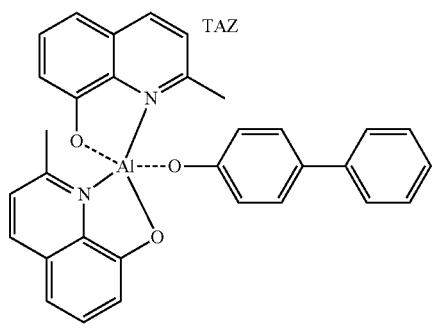

BAlq

<Compound 201>

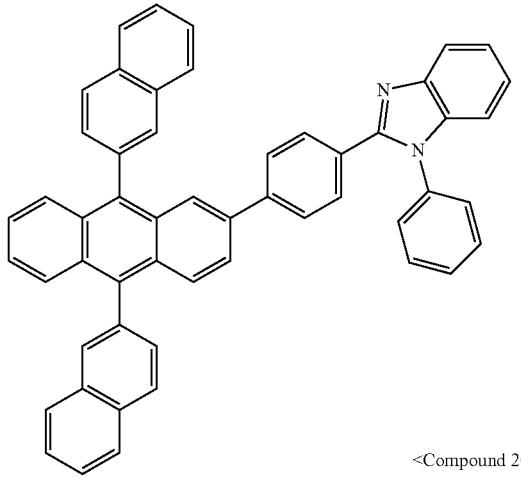

<Compound 202>

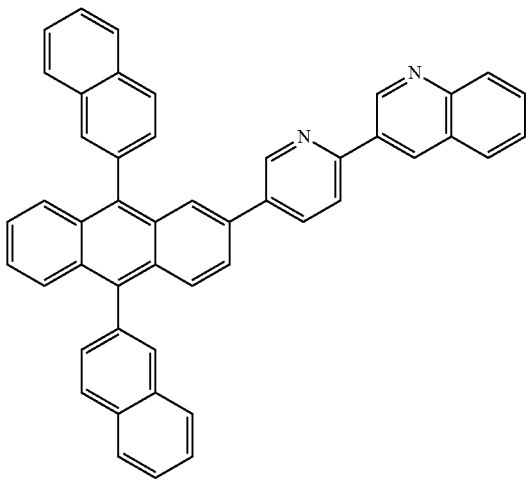

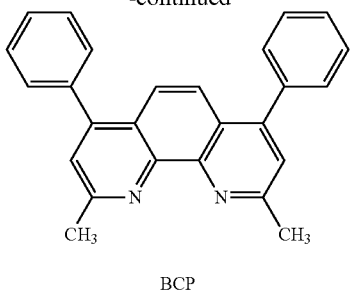

BCP

The thickness of the ETL may be from about 100 Å to about 1,000 Å, and in some embodiments, may be from about 150 Å to about 500 Å. When the thickness of the ETL is within these ranges, the ETL may have satisfactory electron transporting ability without a substantial increase in driving voltage.

In some embodiments the ETL may further include a metal-containing material, in addition to any known electron-transporting organic compound.

The metal-containing material may include a lithium (Li) complex. Non-limiting examples of the Li complex are lithium quinolate (Liq) and Compound 203 below:

<Compound 203>

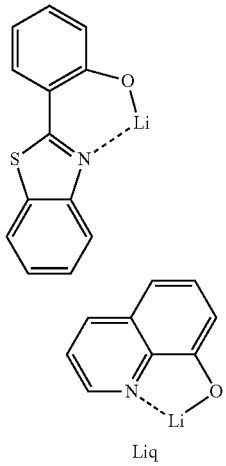

Liq

Then, an EIL, which facilitates injection of electrons from the cathode, may be formed on the ETL. Any suitable electron-injecting material may be used to form the EIL.

Non-limiting examples of materials for forming the EIL are LiF, NaCl, CsF, Li$_2$O, and BaO, which are known in the art. The deposition and coating conditions for forming the EIL 18 may be similar to those for the formation of the HIL, though the deposition and coating conditions may vary according to the material that is used to form the EIL 18.

The thickness of the EIL may be from about 1 Å to about 100 Å, and in some embodiments, may be from about 3 Å to about 90 Å. When the thickness of the EIL is within these ranges, the EIL may have satisfactory electron injection ability without a substantial increase in driving voltage.

A second electrode 17 is disposed on the organic layer 15. The second electrode 17 may be a cathode that is an electron injection electrode. A material for forming the second electrode 17 may be a metal, an alloy, an electro-conductive compound, which have a low work function, or a mixture thereof. In this regard, the second electrode 9 may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type reflective, semi-transmissive, or transmissive electrode. In some embodiments, to manufacture a top-emission light-emitting diode, the transmission electrode may be formed of indium tin oxide (ITO) or indium zinc oxide (IZO). When the organic light-emitting diode is used in a large-size full color display, the second electrode (cathode) of the organic light-emitting diode may be a reflective electrode, but is not limited thereto.

Although the organic light-emitting diode of FIG. 1 is described above, the present invention is not limited thereto.

When a phosphorescent dopant is used in the EML, a HBL may be formed between the HTL and the EML or between the H-functional layer and the EML by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any known hole-blocking material may be used. Non-limiting examples of hole-blocking materials are oxadiazole derivatives, triazole derivatives, and phenanthroline derivatives. For example, bathocuproine (BCP) represented by the following formula may be used as a material for forming the HBL.

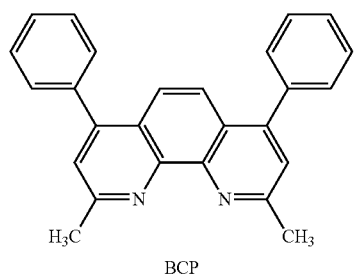

BCP

The thickness of the HBL may be from about 20 Å to about 1000 Å, and in some embodiments, may be from about 30 Å to about 300 Å. When the thickness of the HBL is within these ranges, the HBL may have improved hole blocking ability without a substantial increase in driving voltage.

The organic light-emitting diode may be used in a full color display, a lamp, or the like. For example, the organic light-emitting diode may be a full color display.

According to an embodiment of the present invention, an organic light-emitting diode may include: a substrate including a first subpixel, second subpixel, and a third subpixel; a plurality electrodes disposed in the first subpixel, the second subpixel, and the third subpixel, respectively; a second electrode disposed opposite to the first electrodes as a common electrode of the first subpixel, the second subpixel, and the third subpixel; a first emission layer disposed between the first electrode the second electrode of the first subpixel to emit first-color light; a second emission layer disposed between the first electrode and the second electrode of the second subpixel to emit second-color light; and a third emission layer disposed between the first electrode and the second electrode of the third subpixel to emit third-color light, wherein the first emission layer includes at least one of the pyrene-based compounds of Formula 1 above. The first electrode may be a transmissive electrode or a semi-transmissive electrode, and the second electrode may be a reflective electrode. In some other embodiments, the first electrode may be a reflective electrode, and the second electrode may be a transmissive electrode or a semi-transmissive electrode.

In the organic light-emitting diode described above, a mixed light of the first-color light, the second-color light, and the third-color light is white light. Accordingly, the organic light-emitting diode may serve as a full color display. The first-color light may be blue light. The second-color light may be green light, and the third-color light may be red light.

Since including at least one the pyrene-based compound of Formula 1 above, the first emission layer of the organic light-emitting diode may emit first-color light (blue light) having high color purity (for example, with a y coordinate of 1.0 or less that is near to the NTSC or sRGB specification. Thus, the organic light-emitting diode may be used as a high-definition large-screen TV.

The organic light-emitting diode may be a bottom-emission organic light-emitting diode with a transmissive or semi-transmissive electrode as the first electrode and a reflective electrode as the second electrode.

In some other embodiments, the organic light-emitting diode may be a top-emission organic light-emitting diode with a reflective electrode as the first electrode and a transmissive or semi-transmissive electrode as the second electrode.

Using the pyrene-based compound of Formula 1 above, the organic light-emitting diode may emit blue light having high color purity (for example, with a y coordinate of 1.0 or less) that is near to the sRGB specification, and thus may not need a complicated resonance structure for color purity compensation, which lowers manufacturing cost.

The full color display may be applicable in a TV, a PC monitor, a mobile communication terminal, an MP3 player, a car navigation system, and the like.

As used herein, the unsubstituted $C_1$-$C_{60}$ alkyl group (or a $C_1$-$C_{60}$ alkyl group) may be a linear or branched C1-C60 alkyl group, including a methyl group, an ethyl group, a propyl group, an isobutyl group, a sec-butyl group, a pentyl group, an iso-amyl group, and a hexyl group. The substituted $C_1$-$C_{60}$ alkyl group may be a $C_1$-$C_{60}$ alkyl group of which at least one hydrogen atom is substituted with at least one selected from, a deuterium atom; —F; —Cl; —Br; —I; —CN; a hydroxy group; —$NO_2$; an amino group; an amidino group; a hydrazine; a hydrazone; a carboxyl group or a salt thereof; a sulfonic acid group or a salt thereof; a phosphoric acid group or a salt thereof; a tri($C_6$-$C_{60}$ aryl)silyl group; $C_1$-$C_{60}$alkyl group, a $C_1$-$C_{60}$alkoxy group, a $C_2$-$C_{60}$alkenyl group, and a $C_2$-$C_{60}$alkynyl group;

a $C_1$-$C_{60}$alkyl group, a $C_1$-$C_{60}$alkoxy group, a $C_2$-$C_{60}$alkenyl group, and a $C_2$-$C_{60}$alkynyl group, substituted with at least one of a deuterium atom, —F, —Cl, —Br, —I, —CN, a hydroxyl group, —$NO_2$, an amino group, an amidino group, a hydrazine, a hydrazone, a carboxyl group or a salt thereof, a sulfonic acid group or a salt thereof, and a phosphoric acid group or a salt thereof;

a $C_3$-$C_{60}$cycloalkyl group, a $C_3$-$C_{60}$cycloalkenyl group, a $C_6$-$C_{60}$aryl group, a $C_2$-$C_{60}$heteroaryl group, a $C_6$-$C_{60}$aralkyl group, $C_6$-$C_{60}$aryloxy group, and $C_6$-$C_{60}$ arylthio group; and a $C_3$-$C_{60}$cycloalkyl group, a $C_3$-$C_{60}$cycloalkenyl group, a $C_6$-$C_{60}$aryl group, a $C_2$-$C_{60}$heteroaryl group, a $C_6$-$C_{60}$aralkyl group, a $C_6$-$C_{60}$aryloxy group, and a $C_6$-$C_{60}$arylthio group, substituted with at least one of a deuterium atom, —F, —Cl, —Br, —I, —CN, a hydroxyl group, —NO$_2$, an amino group, an amidino group, a hydrazine, a hydrazone, a carboxyl group or a salt thereof, a sulfonic acid group or a salt thereof, a phosphoric acid group or a salt thereof, $C_1$-$C_{60}$ an alkyl group, a $C_1$-$C_{60}$alkyl group substituted with at least one —F, a $C_1$-$C_{60}$alkoxy group, a $C_2$-$C_{60}$ an alkenyl group, a $C_2$-$C_{60}$ an alkynyl group, a $C_6$-$C_{60}$aryl group, and a $C_2$-$C_{60}$heteroaryl group.

The unsubstituted $C_1$-$C_{60}$ alkoxy group ($C_1$-$C_{60}$ alkoxy group) may be a group represented by —OA, wherein A is an unsubstituted $C_1$-$C_{60}$ alkyl group described above. Examples of the unsubstituted $C_1$-$C_{60}$ alkoxy group are a methoxy group, an ethoxy group, and an isopropyloxy group. At least one of the hydrogen atoms in the alkoxy group may be substituted with the substituents described above in conjunction with the substituted $C_1$-$C_{60}$ alkyl group.

The unsubstituted $C_2$-$C_{60}$ alkenyl group ($C_2$-$C_{60}$ alkenyl group) is a $C_2$-$C_{60}$ alkyl group having at least one carbon-carbon triple bond in the center or at a terminal thereof. Examples of the alkenyl group are an ethenyl group, a propenyl group, a butenyl group, and the like. At least one hydrogen atom in the unsubstituted $C_2$-$C_{60}$ alkenyl group may be substituted with those substituents described above in conjunction with the substituted $C_1$-$C_{60}$ alkyl group.

The unsubstituted $C_2$-$C_{60}$ alkynyl group ($C_2$-$C_{60}$ alkynyl group) is a $C_2$-$C_{60}$ alkyl group having at least one carbon-carbon triple bond in the center or at a terminal thereof. Examples of the unsubstituted $C_2$-$C_{60}$ alkynyl group ($C_2$-$C_{60}$ alkynyl group) are an ethenyl group, a propynyl group, and the like. At least one hydrogen atom in the alkynyl group may be substituted with those substituents described above in conjunction with the substituted $C_1$-$C_{60}$ alkyl group.

As used herein, the unsubstituted $C_3$-$C_{60}$ cycloalkyl group indicates a cyclic, monovalent $C_3$-$C_{60}$ saturated hydrocarbon chain. Non-limiting examples of the unsubstituted $C_3$-$C_{60}$ cycloalkyl group are cyclopropyl, cyclobutyl, cyclopentyl, cyclohexyl, and cyclooctyl. At least one hydrogen atom in the cycloalkyl group may be substituted with those substituents described above in conjunction with the substituted $C_1$-$C_{60}$ alkyl group.

As used herein, the unsubstituted $C_3$-$C_{60}$ cycloalkenyl group indicates a nonaromatic, cyclic unsaturated hydrocarbon chain with at least one carbon-carbon double bond. Examples of the unsubstituted $C_3$-$C_{60}$ cycloalkenyl group include cyclopropenyl, cyclobutenyl, cyclopentenyl, cyclohexcenyl, cycloheptenyl, 1,3-cyclohexadienyl, 1,4-cyclohexadienyl, 2,4-cycloheptadienyl, and 1,5-cyclooctadienyl. At least one hydrogen atom in the cycloalkenyl group may be substituted with those substituents described above in conjunction with the substituted $C_1$-$C_{60}$ alkyl group.

The unsubstituted $C_6$-$C_{60}$ aryl group is a monovalent group having a carbocyclic aromatic system having 6 to 60 carbon atoms including at least one aromatic ring. The unsubstituted $C_6$-$C_{60}$ arylene group is a divalent group having a carbocyclic aromatic system having 6 to 60 carbon atoms including at least one aromatic ring. When the aryl group and the arylene group have at least two rings, they may be fused to each other via a single bond. At least one hydrogen atom in the aryl group and the arylene group may be substituted with those substituents described above in conjunction with the $C_1$-$C_{60}$ alkyl group.

Examples of the substituted or unsubstituted $C_6$-$C_{60}$ aryl group are a phenyl group, a $C_1$-$C_{10}$ alkylphenyl group (e.g., an ethylphenyl group), a $C_1$-$C_{10}$ alkylbiphenyl group (e.g., an ethylbiphenyl group), a halophenyl group (e.g., an o-, m- or p-fluorophenyl group and a dichlorophenyl group), a dicyanophenyl group, a trifluoromethoxyphenyl group, an o-, m- or p-tolyl group, an o-, m- or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a halonaphthyl group (e.g., a fluoronaphthyl group), a $C_1$-$C_{10}$ alkylnaphthyl group (e.g., a methylnaphthyl group), a $C_1$-$C_{10}$ alkoxynaphthyl group (e.g., a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylenyl group, a pyrenyl group, a chrysenyl group, an ethyl-chrysenyl group, a picenyl group, a perylenyl group, a chloroperylenyl group, a pentaphenyl group, a pentacenyl group, a tetraphenylenyl group, a hexaphenyl group, hexacenyl group, a rubicenyl group, a coronenyl group, a trinaphthylenyl group, a heptaphenyl group, a heptacenyl group, a pyranthrenyl group, and an ovalenyl group. Examples of the substituted $C_6$-$C_{60}$ aryl group may be inferred based on those of the unsubstituted $C_6$-$C_{60}$ aryl group and the substituted $C_1$-$C_{30}$ alkyl group described above. Examples of the substituted or unsubstituted $C_6$-$C_{60}$ arylene group may be inferred based on those examples of the substituted or unsubstituted $C_6$-$C_{60}$ aryl group described above.

The unsubstituted $C_2$-$C_{60}$ heteroaryl group is a monovalent carbocyclic aromatic system having at least one aromatic ring and at least one of the heteroatoms selected from the group consisting of N, O, P, and S as a ring-forming atom. The unsubstituted $C_2$-$C_{60}$ heteroarylene group is a divalent carbocyclic aromatic system having at least one aromatic ring and at least one aromatic ring and at least one of the heteroatoms selected from the group consisting of N, O, P, and S. In this regard, when the heteroaryl group and the heteroarylene group have at least two rings, they may be fused to each other via a single bond. At least one hydrogen atom in the heteroaryl group and the heteroarylene group may be substituted with those substituents described with reference to the $C_1$-$C_{60}$ alkyl group.

Examples of the unsubstituted $C_2$-$C_{60}$ heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazolyl group, an indolyl group, a quinolinyl group, an isoquinolinyl group, a benzoimidazolyl group, an imidazopyridinyl group and an imidazopyrimidinyl group. Examples of the substituted or unsubstituted $C_2$-$C_{60}$ heteroarylene group may be inferred based on those examples of the substituted or unsubstituted $C_2$-$C_{60}$ arylene group described above.

The substituted or unsubstituted $C_6$-$C_{60}$ aryloxy group indicates —OA$_2$ (where A$_2$ is a substituted or unsubstituted $C_6$-$C_{60}$ aryl group described above). The substituted or unsubstituted $C_6$-$C_{60}$ arylthiol group indicates —SA$_3$ (where A$_3$ is a substituted or unsubstituted $C_6$-$C_{60}$ aryl group described above).

Hereinafter, the present invention will be described in detail with reference to the following synthesis examples and other examples. However, these examples are for illustrative purposes only and are not intended to limit the scope of the present invention.

EXAMPLE

Synthesis Example 1: Synthesis of Compound 3

Synthesis of Intermediate A

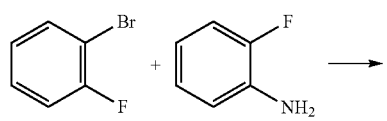

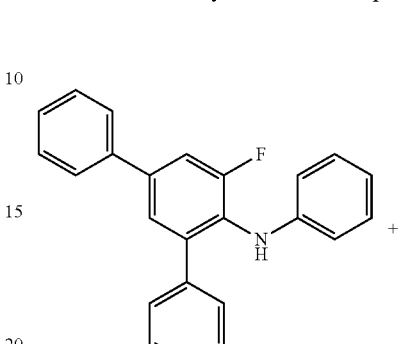

Intermediate A 12.5 g (72 mmole) of 1-bromo-2-fluorobenzene, 8 g (72 mmole) of 2-fluoroaniline, 2 g (3.6 mol) of bis(dibenzylideneacetone)palladium (Pd(dba)$_2$), 5.8 g (10.8 mmol) of bis[(2-diphenylphosphino)phenyl]ether (DPEPhos), and 20 g (220 mmol) of sodium t-butoxide were added with 2000 mL of toluene, and then refluxed in a nitrogen atmosphere for about 12 hours. After completion of the reaction, the solvent was removed by evaporation. The resultant was washed with 5000 ml of methylene chloride and 5000 ml of water. Then, an organic layer was collected and dried using anhydrous magnesium sulfate, followed by recrystallization and silica gel chromatography to obtain 5.6 g of Intermediate A (Yield: 38%).

Synthesis of Intermediate PY1

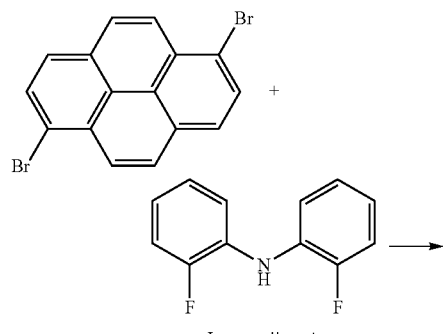

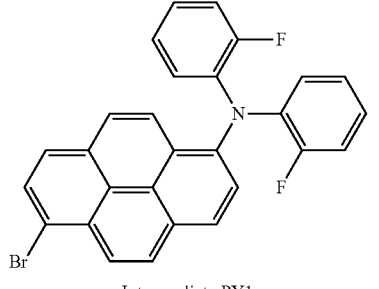

Intermediate PY1

Intermediate PY1 was synthesized in the same manner as in the synthesis of Intermediate A, except that 1,6-dibromopyrene, Intermediate A, and P(t-Bu)$_3$, respectively, instead of 1-bromo-2-fluorobenzene, 2-fluoroaniline, and bis[(2-diphenylphosphino)phenyl]ether (DPEPhos), were used. (Yield; 25%)

Synthesis of Compound 3

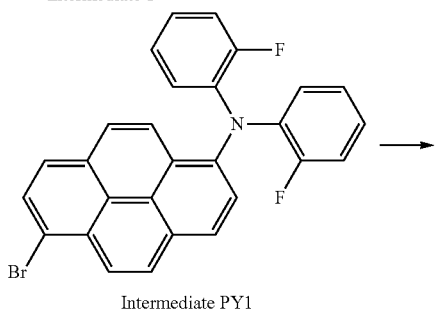

Intermediate 1

Compound 3

Compound 3 was synthesized in the same manner as in the synthesis of Intermediate A, except that Intermediate 1, Intermediate PY1, and P(t-Bu)$_3$, respectively, instead of 1-bromo-2-fluorobenzene, 2-fluoroaniline, and bis[(2-diphenylphosphino)phenyl]ether (DPEPhos), were used. (Yield: 21%)

MS (MALDI-TOF) m/z: 742 [M]+.

Synthesis Example 2: Synthesis of Compound 6

Synthesis of Intermediate B

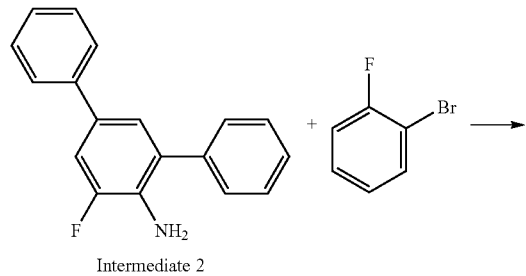

Intermediate 2

Intermediate B

Intermediate B was synthesized in the same manner as in the synthesis of Intermediate A, except that Intermediate 2, instead of 2-fluoroaniline, was used. (Yield; 34%)

Synthesis of Intermediate PY2

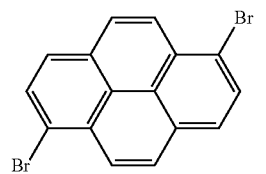

Intermediate 1

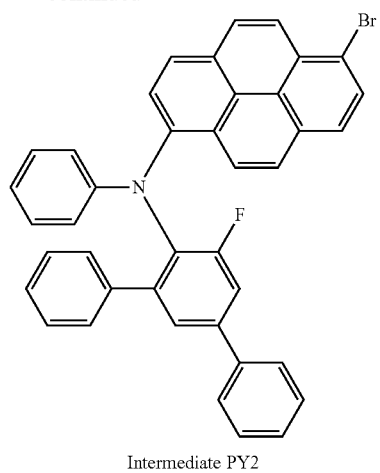

Intermediate PY2

Intermediate PY2 was synthesized in the same manner as in the synthesis of Intermediate A, except that 1,6-dibromopyrene, Intermediate 1, and P(t-Bu)$_3$, respectively, instead of 1-bromo-2-fluorobenzene, 2-fluoroaniline, and bis[(2-diphenylphosphino)phenyl]ether (DPEPhos), were used. (Yield: 23%)

Synthesis of Compound 6

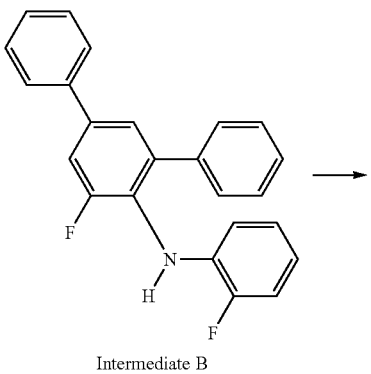

Intermediate PY2

Intermediate B

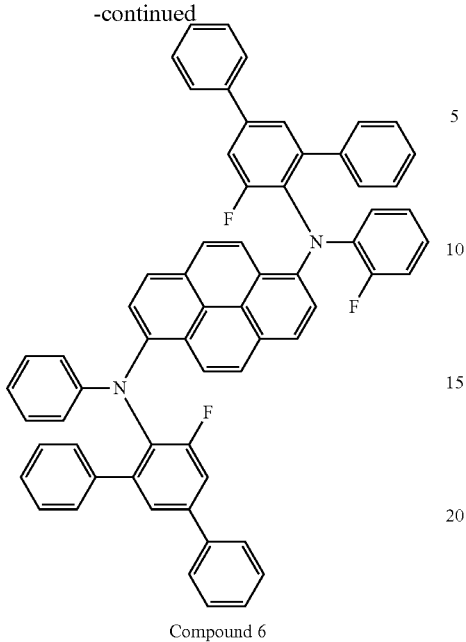

Compound 6

Compound 6 was synthesized in the same manner as in the synthesis of Intermediate A, except that Intermediate PY2, Intermediate B, and P(t-Bu)₃, respectively, instead of 1-bromo-2-fluorobenzene, 2-fluoroaniline, and bis[(2-diphenylphosphino)phenyl]ether (DPEPhos), were used. (Yield: 20%)

MS (MALDI-TOF) m/z: 894 [M]+.

Synthesis Example 3: Synthesis of Compound 7

Synthesis of Intermediate C-9

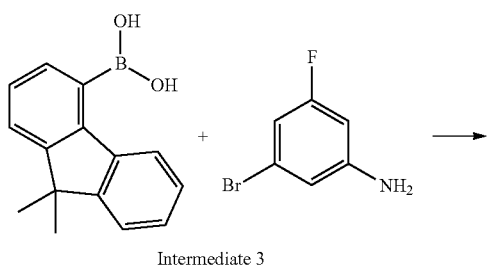

Intermediate 3

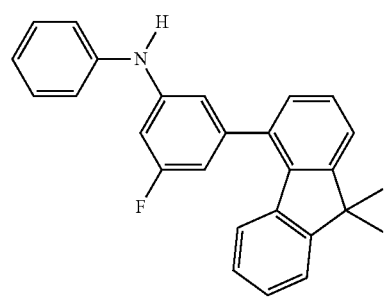

Intermediate C-2

14.3 g (60 mmol) of Intermediate 3, 11.3 g (60 mmol) of 2-bromo-4-fluoroaniline), 1 g (0.9 mmol) of tetrakis triphenylphosphine palladium (Pd(PPh₃)₄), and 126 mL (252 mmol) of a 2M potassium carbonate (K₂CO₃) aqueous solution were dissolved in 200 ml of toluene, mixed together, and then refluxed for about 24 hours. After completion of the reaction, the solvent was removed by evaporation. The resultant was washed with 1000 ml of ethylacetate and 1000 ml of water. Then an organic layer was collected and dried using anhydrous magnesium sulfate, followed by silica gel chromatography to obtain 11.4 g of Intermediate C-2 (Yield: 63%).

Synthesis of Intermediate C-1

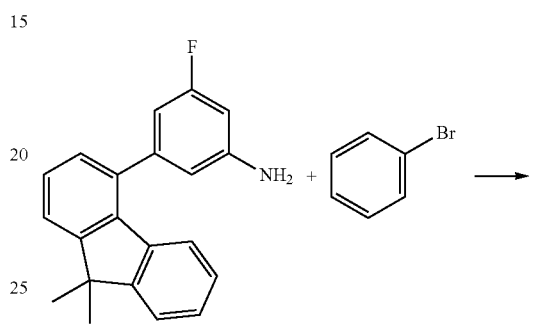

Intermediate C-2

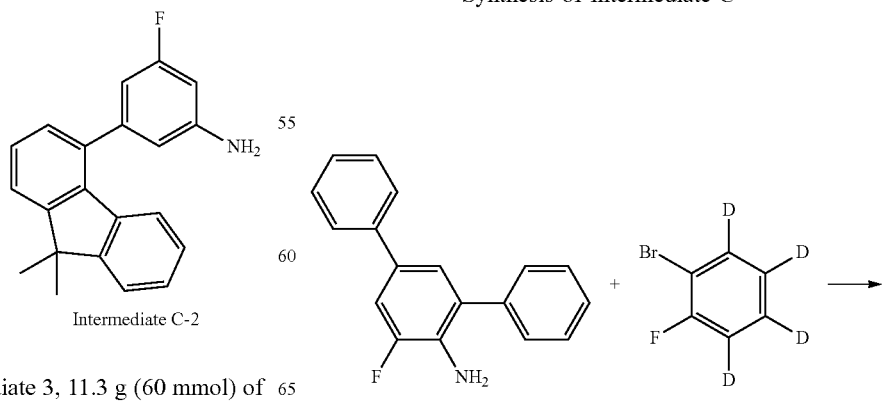

Intermediate C-1

Intermediate C-1 was synthesized in the same manner as in the synthesis of Intermediate A, except that Intermediate C-2, bromobenzene, and P(t-Bu)₃, respectively, instead of 1-bromo-2-fluorobenzene, 2-fluoroaniline, and bis[(2-diphenylphosphino)phenyl]ether (DPEPhos), were used. (Yield: 55%)

Synthesis of Intermediate C

Intermediate 2 + Intermediate 3

122

Synthesis of Compound 7

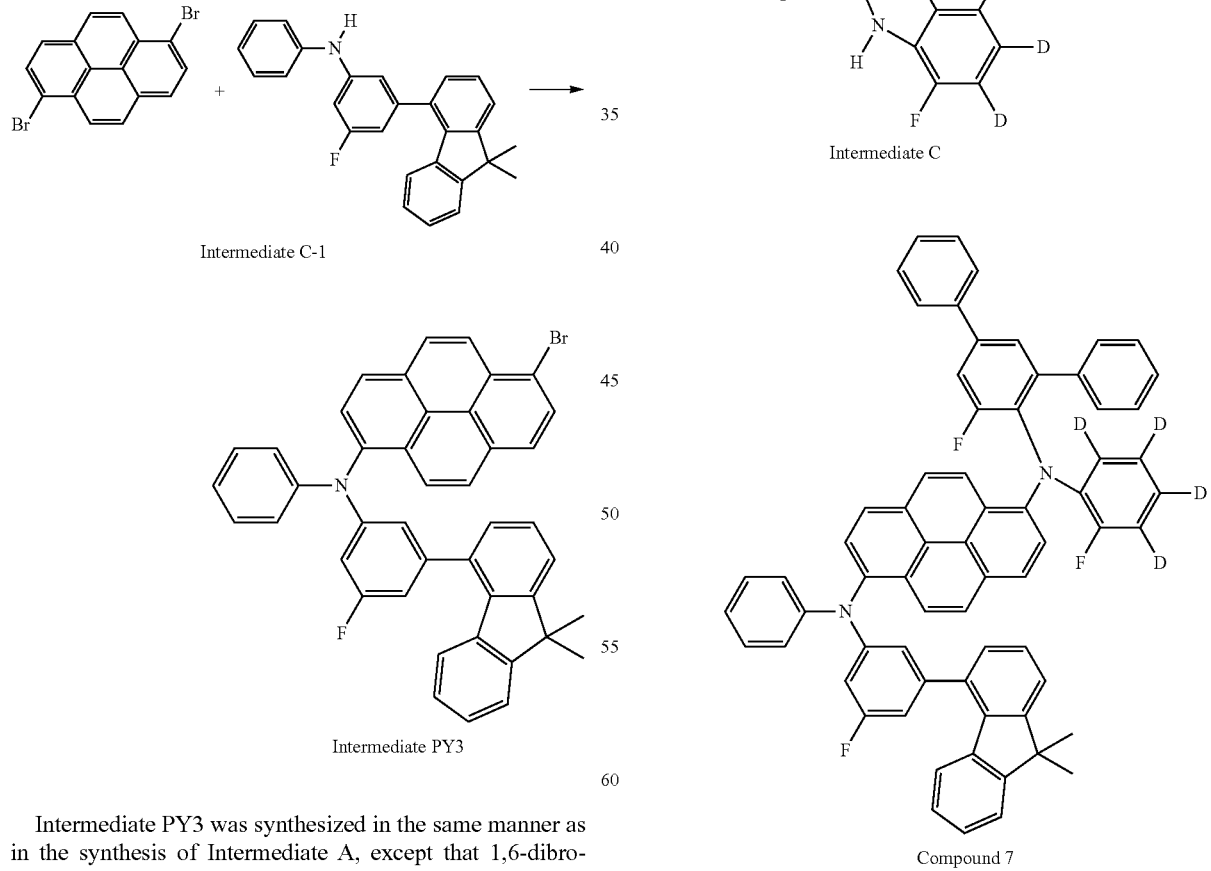

Compound 7

Compound 7 was synthesized in the same manner as in the synthesis of Intermediate A, except that Intermediate

---

-continued

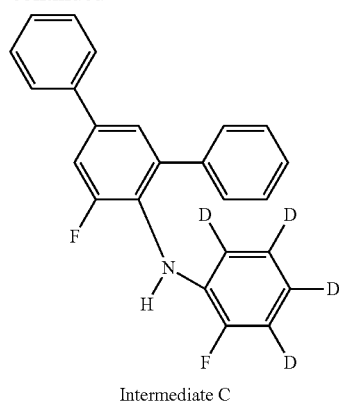

Intermediate C

Intermediate C was synthesized in the same manner as in the synthesis of Intermediate A, except that Intermediate 2 and intermediate 3, respectively, instead of 1-bromo-2-fluorobenzene and 2-fluoroaniline, were used. (Yield: 20%)

Synthesis of Intermediate PY3

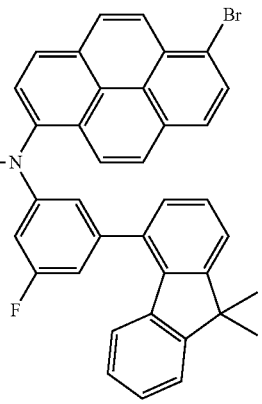

Intermediate C-1

Intermediate PY3

Intermediate PY3 was synthesized in the same manner as in the synthesis of Intermediate A, except that 1,6-dibromopyrene, Intermediate C-1, and P(t-Bu)₃, respectively, instead of 1-bromo-2-fluorobenzene, 2-fluoroaniline, and bis[(2-diphenylphosphino)phenyl]ether (DPEPhos), were used. (Yield: 25%)

PY3, Intermediate C, and P(t-Bu)$_3$, respectively, instead of 1-bromo-2-fluorobenzene, 2-fluoroaniline, and bis[(2-diphenylphosphino)phenyl]ether (DPEPhos), were used. (Yield: 24%)

MS (MALDI-TOF) m/z: 938 [M]+.

Example 1

A corning 15 Ω/cm$^2$ (1200 Å) ITO glass substrate was cut to a size of 50 mm×50 mm×0.5 mm and then sonicated in isopropyl alcohol and pure water each for 15 minutes, and then cleaned by irradiation of ultraviolet rays for 30 minutes and exposure to ozone. The resulting glass substrate was loaded into a vacuum deposition diode.

2-TNATA was vacuum-deposited on the ITO layer as an anode on the glass substrate to form an HIL having a thickness of about 600 Å, and then α-NPD was vacuum-deposited on the HIL at a deposition rate of about 1 Å/sec to form a HTL having a thickness of about 300 Å.

Compound 3 (dopant) and 9,10-di-naphthalene-2-yl-anthracene (AND) (host) were co-deposited on the HTL at a deposition rate of about 0.05 Å/sec and about 1 Å/sec, respectively, to form an EML having a thickness of about 200 Å.

Then, Alq$_3$ was deposited on the EML to form an ETL having a thickness of about 300 Å, and then LiF was deposited on the ETL to form an EIL having a thickness of about 10 Å. Then, Al was deposited on the EIL to form a second electrode (cathode) having a thickness of about 2000 Å, thereby forming a cathode having a thickness of about 2000 Å and completing the manufacture of an organic light-emitting diode.

Example 2

An organic light-emitting diode was manufactured in the same manner as in Example 1, except that Compound 6, instead of Compound 3, was used as a dopant in forming the EML.

Example 3

An organic light-emitting diode was manufactured in the same manner as in Example 1, except that Compound 7, instead of Compound 3, was used as a dopant in forming the EML.

Comparative Example 1

An organic light-emitting diode was manufactured in the same manner as in Example 1, except that Compound A, instead of Compound 1, was used as a dopant in forming the EML.

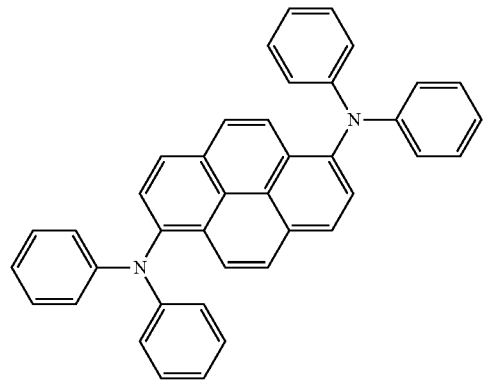

<Compound A>

Comparative Example 2

An organic light-emitting diode was manufactured in the same manner as in Example 1, except that Compound B, instead of Compound 1, was used as a dopant in forming the EML.

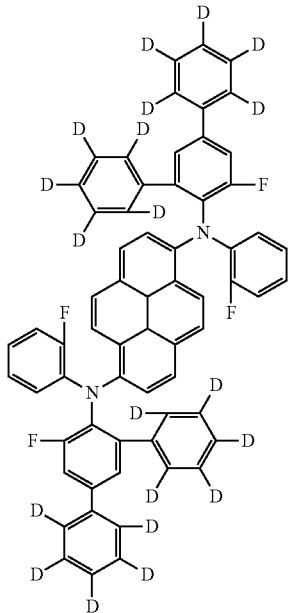

<Compound B>

Evaluation Example 1

Driving voltages, current densities, luminance, and color coordinates of the organic light-emitting diodes of Examples 1 to 3 and Comparative Examples 1 to 3 were measured using a PR650 (Spectroscan) Source Measurement Unit. (available from Photo Research, Inc.). The results are shown in Table 1 below. (IS90 lifetime indicates the time taken until a measured initial luminance (assumed as 100%) is reduced to 90%.)

TABLE 1

| | EML host | EML dopant | Luminance (cd/m²) | Current density (cd/A) | Driving voltage (V) | IS90 lifetime (hr @ 700 nit) | Color coordinates (CIE) |
|---|---|---|---|---|---|---|---|
| Example 1 | ADN | Compound 3 | 700 | 11 | 4.1 | 140 | (0.14, 0.091) |
| Example 2 | ADN | Compound 6 | 700 | 12 | 4.2 | 127 | (0.14, 0.095) |
| Example 3 | ADN | Compound 7 | 700 | 11 | 4.2 | 133 | (0.14, 0.099) |
| Comparative Example 1 | ADN | Compound A | 700 | 16 | 4.6 | 61 | (0.16, 0.20) |
| Comparative Example 2 | ADN | Compound B | 700 | 16 | 4.5 | 55 | (0.14, 0.14) |

Referring to Table 1, the organic light-emitting devices of Examples 1 to 3 were found to have lower driving voltages, higher current densities, and higher color purities, as compared to the organic light-emitting diodes of Comparative Examples 1 and 2.

As described above, according to the one or more embodiments of the present invention, an organic light-emitting diode including the pyrene-based compound of Formula 1 above, may have a low driving voltage, a high current density, a high color purity, and improved lifetime characteristics.

It should be understood that the exemplary embodiments described therein should be considered in a descriptive sense only and not for purposes of limitation. Descriptions of features or aspects within each embodiment should typically be considered as available for other similar features or aspects in other embodiments.

What is claimed is:

1. Pyrene-based compounds represented by Formula 1 below:

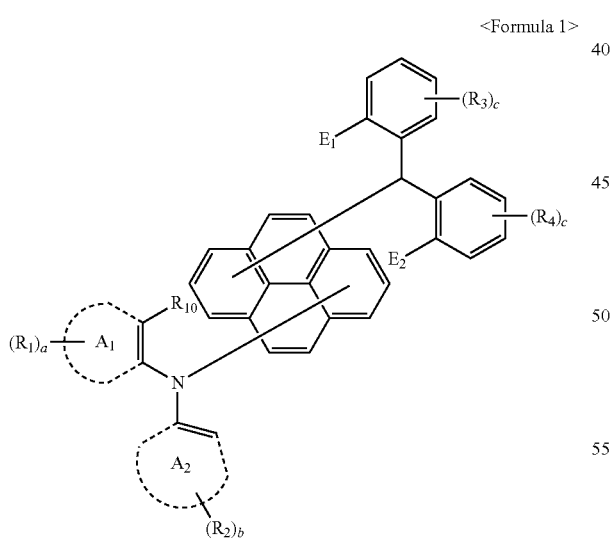

<Formula 1> wherein, $E_1$ and $E_2$ are each independently an electron withdrawing group selected from —F; —CN;

or a $C_1$-$C_{60}$ alkyl group substituted with at least one —F;

the $A_1$ ring and $A_2$ ring are each independently a $C_6$-$C_{30}$ aromatic ring;

$R_{10}$ is selected from a hydrogen atom, a deuterium atom, a hydroxyl group, a carboxyl group or a salt thereof, a sulfonic acid group or a salt thereof, a phosphoric acid group or a salt thereof, a $C_1$-$C_{60}$ alkyl group, a $C_1$-$C_{60}$ alkoxy group, or a $C_6$-$C_{60}$ aryl group;

$R_1$ to $R_4$ are each independently within each ring, and across rings, at least one selected from, a hydrogen atom, a deuterium atom, —F, —Cl, —Br, —I, —CN, a hydroxy group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkoxy group, a $C_2$-$C_{60}$ alkenyl group, and a $C_2$-$C_{60}$ alkynyl group, a $C_1$-$C_{60}$ alkyl group, a $C_1$-$C_{60}$ alkoxy group, a $C_2$-$C_{60}$ alkenyl group, or a $C_2$-$C_{60}$ alkynyl group, substituted with at last one of a deuterium atom, —F, —Cl, —Br, —I, —CN, a hydroxyl group, a nitro group, an amino group, an amidino group, a hydrazine, a hydrazone, a carboxyl group or a salt thereof, a sulfonic acid group or a salt thereof, or a phosphoric acid group or a salt thereof, a $C_3$-$C_{10}$ cycloalkyl group, a $C_3$-$C_{10}$ cycloalkenyl group, a $C_6$-$C_{60}$ aryl group, a $C_2$-$C_{60}$ heteroaryl group, a $C_6$-$C_{60}$ aralkyl group, a $C_6$-$C_{60}$ aryloxy group, or a $C_6$-$C_{60}$ arylthio group, a $C_3$-$C_{10}$ cycloalkyl group, a $C_3$-$C_{10}$ cycloalkenyl group $C_6$-$C_{60}$ aryl group, a $C_2$-$C_{60}$ heteroaryl group, a $C_6$-$C_{60}$ aralkyl group, a $C_6$-$C_{60}$ aryloxy group, and a $C_6$-$C_{60}$ arylthio group, substituted with at least one of a deuterium atom, —F, —Cl, —Br, —I, —CN, a hydroxyl group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{60}$ alkyl group, a $C_1$-$C_{60}$ alkyl group substituted with at least one —F, a $C_1$-$C_{60}$ alkoxy group, a $C_2$-$C_{60}$ alkenyl group, a $C_2$-$C_{60}$ alkynyl group, a $C_6$-$C_{60}$ aryl group, a $C_6$-$C_{60}$ aryl group substituted with at least one —F, or a $C_2$-$C_{60}$ heteroaryl group, and —N($Q_1$)($Q_2$) or —Si($Q_3$)($Q_4$)($Q_5$), where $Q_1$ to $Q_5$ are each independently selected from a $C_1$-$C_{60}$ alkyl group, a $C_1$-$C_{60}$ alkoxy group, a $C_2$-$C_{60}$ alkenyl group, a $C_2$-$C_{60}$ alkynyl group, a $C_3$-$C_{60}$ cycloalkyl group, a $C_3$-$C_{60}$ cycloalkenyl group, a $C_6$-$C_{60}$ aryl group, a $C_2$-$C_{60}$ heteroaryl group, a $C_6$-$C_{60}$aralkyl group, a $C_6$-$C_{60}$ aryloxy group, and a $C_6$-$C_{60}$ arylthio group, and a to d are each independently an integer from 1 to 4;

wherein the group represented by

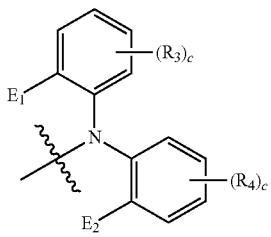

and the group represented by

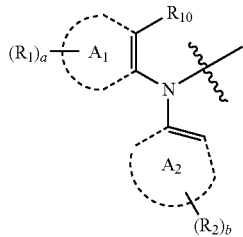

have different chemical structures.

2. The pyrene-based compounds of claim 1, wherein the pyrene-based compounds are represented by Formula 1(1) below:

<Formula 1(1)>

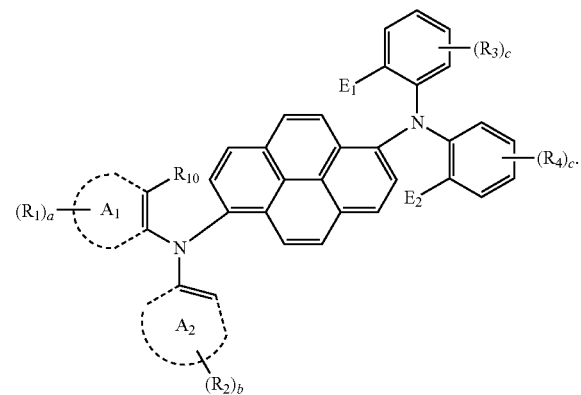

3. The pyrene-based compounds of claim 1, wherein $E_1$ and $E_2$ both are —F.

4. The pyrene-based compounds of claim 1, wherein the $A_1$ ring and the $A_2$ ring are each independently selected from a benzene ring, a naphthalene ring, an anthracene ring, a fluorene ring, a pyrene ring, a chrysene ring, and a phenanthrene ring.

5. The pyrene-based compounds of claim 1, wherein the $A_1$ ring and the $A_2$ ring are each independently a benzene ring or a naphthalene ring.

6. The pyrene-based compounds of claim 1, wherein $R_{10}$ is selected from a hydrogen atom, a deuterium atom, a hydroxyl group, a carboxyl group or a salt thereof, a sulfonic acid group or a salt thereof, a phosphoric acid group or a salt thereof, a $C_1$-$C_{10}$ alkyl group, a phenyl group, a naphthyl group, and an anthryl group.

7. The pyrene-based compounds of claim 1, wherein $R_{10}$ is a hydrogen atom.

8. The pyrene-based compounds of claim 1, wherein $R_1$ to $R_4$ are each independently within each ring, and across rings, one selected from, a hydrogen atom, a deuterium atom, —F, —Cl, —Br, —I, —CN, a hydroxy group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group;

a $C_1$-$C_{10}$ alkyl group, or a $C_1$-$C_{10}$ alkoxy group, substituted with at least one of a deuterium atom, —F, —Cl, —Br, —I, —CN, a hydroxyl group, a nitro group, an amino group, an amidino group, a hydrazine, a hydrazone, a carboxyl group or a salt thereof, a sulfonic acid group or a salt thereof, or a phosphoric acid group or a salt thereof;

a phenyl group, a naphthyl group, an anthryl group, a pyrenyl group, a phenanthrenyl group, a fluorenyl group, a spiro-fluorenyl group, a dibenzofuranyl group, or a dibenzothiophenyl group; and a phenyl group, a naphthyl group, an anthryl group, a pyrenyl group, a phenanthrenyl group, a fluorenyl group, a spiro-fluorenyl group, a dibenzofuranyl group, or a dibenzothiophenyl group, substituted with at least one of a deuterium atom, —F, —Cl, —Br, —I, —CN, a hydroxyl group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, a $C_1$-$C_{10}$ alkyl group substituted with at least one —F, a $C_1$-$C_{10}$ alkoxy group, a $C_1$-$C_{10}$ alkoxy group substituted with at least one —F, a phenyl group, a naphthyl group, or an anthryl group.

9. The pyrene-based compounds of claim 1, wherein, in Formula 1, the group represented by

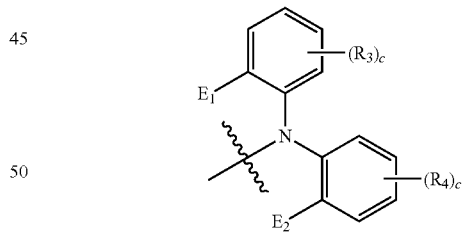

is selected from the groups represented by the following formulae:

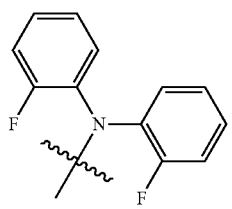

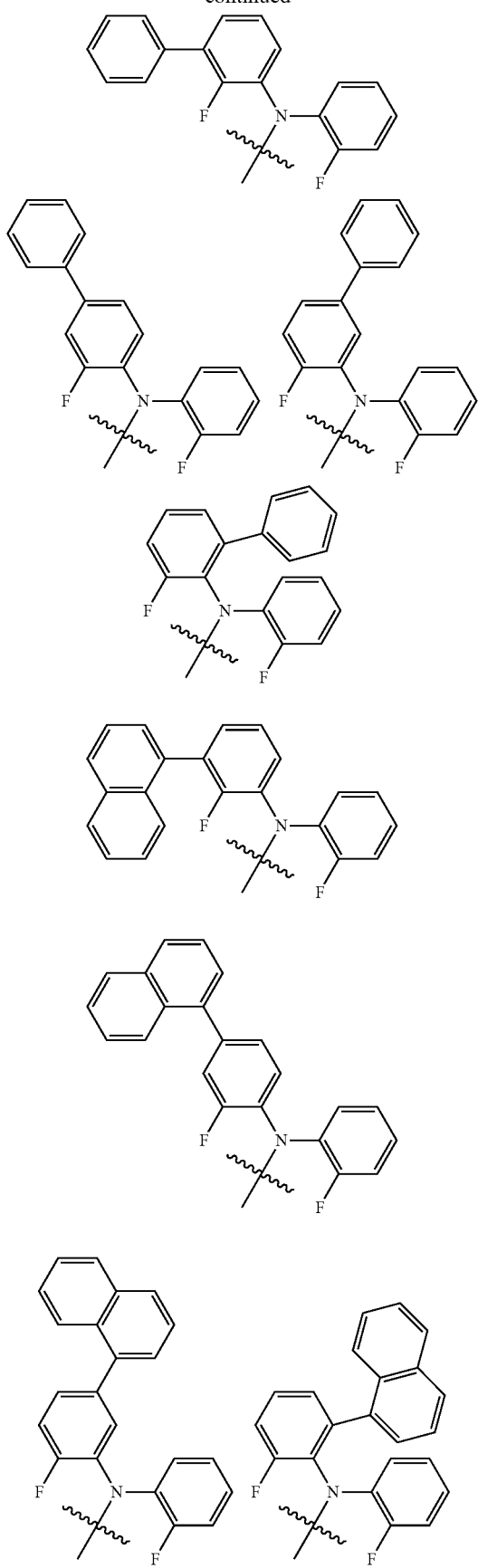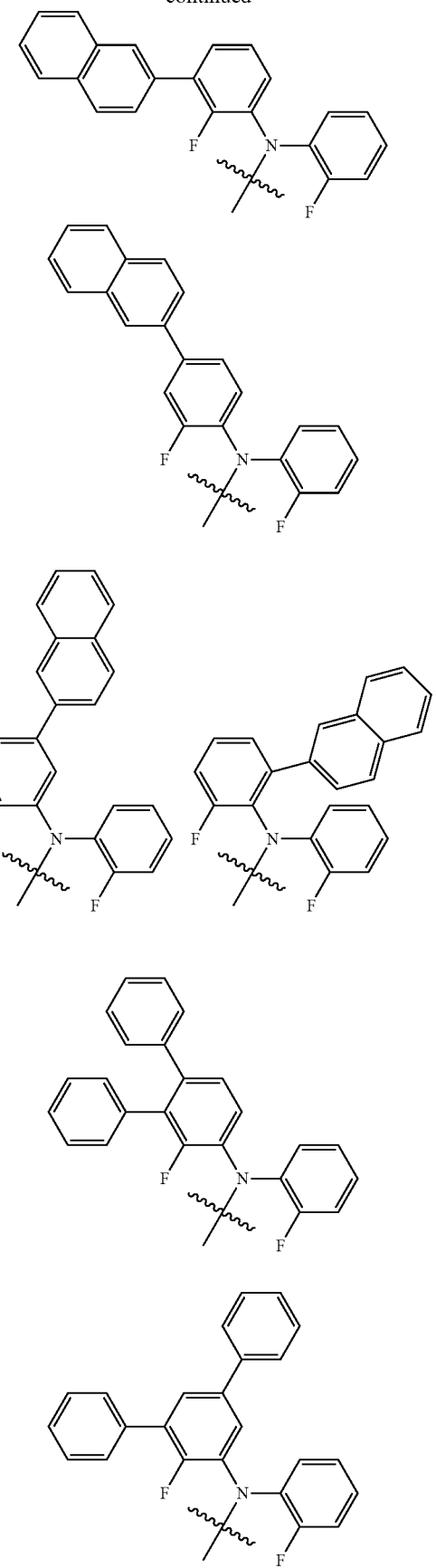

131
-continued
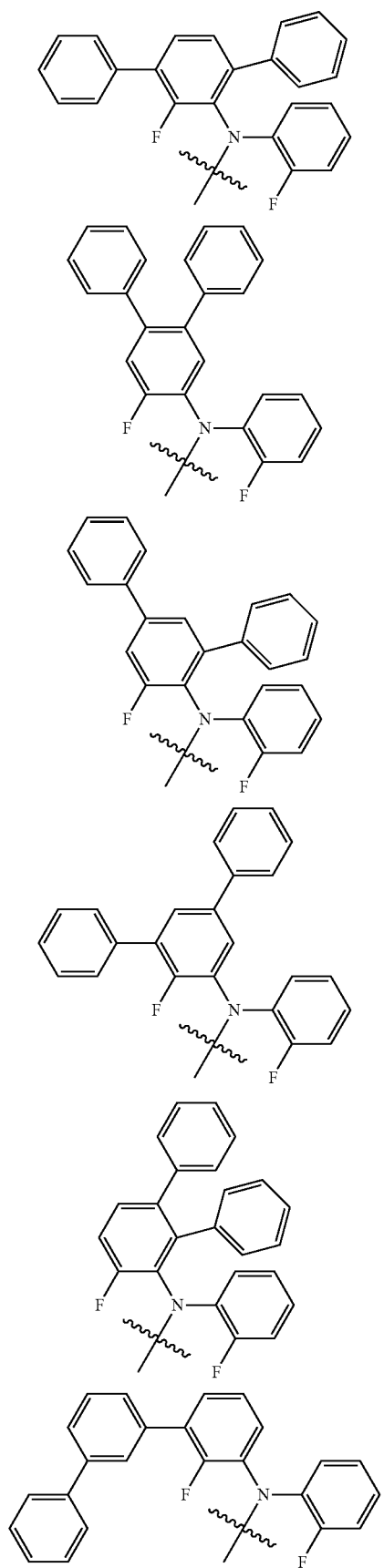
132
-continued
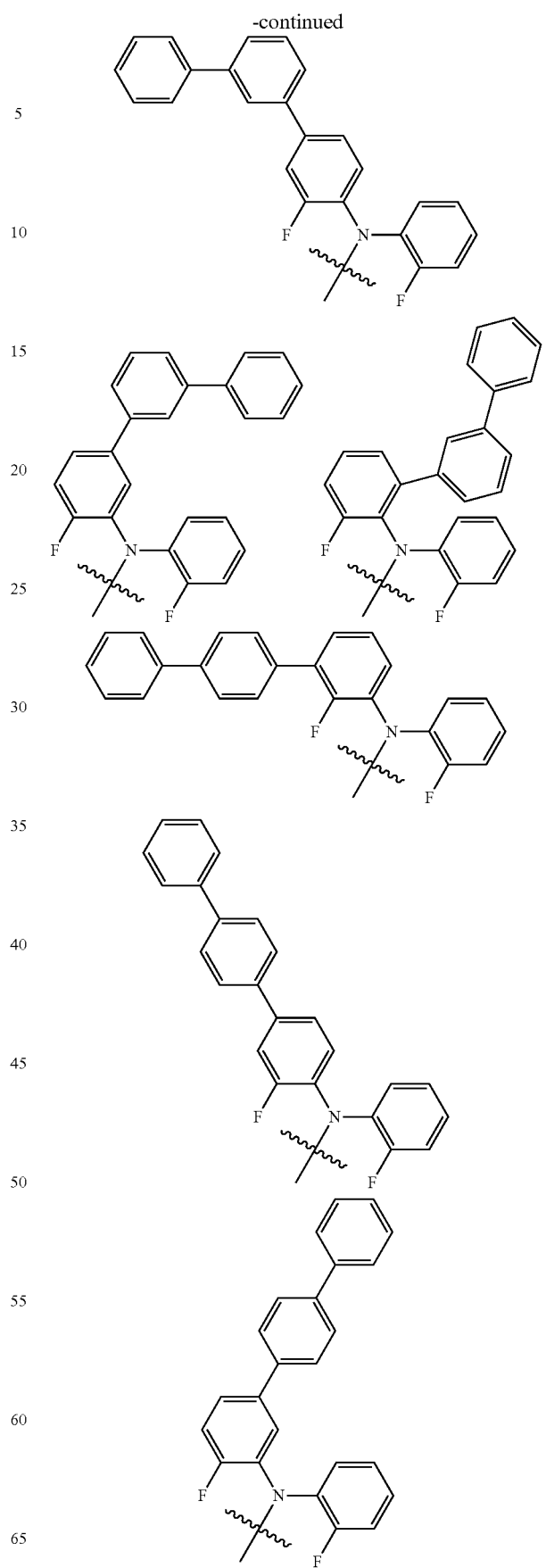

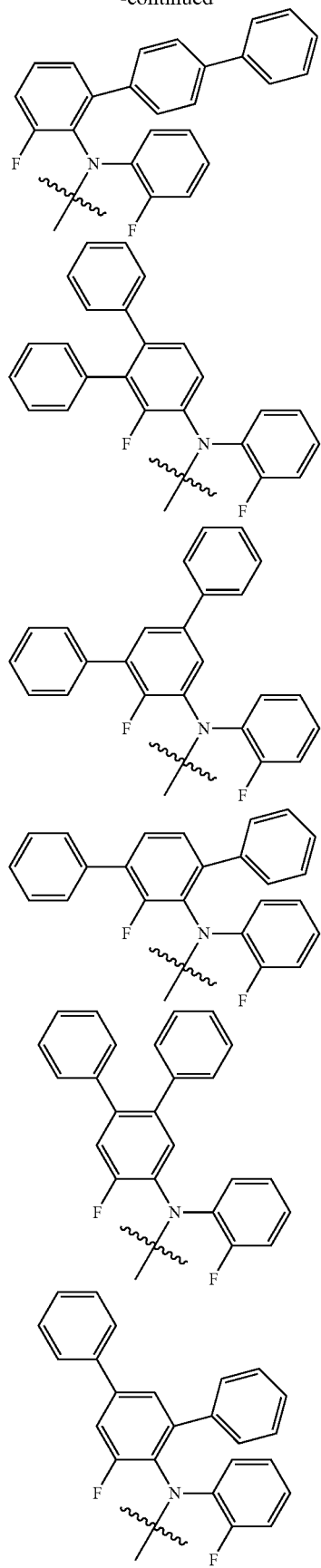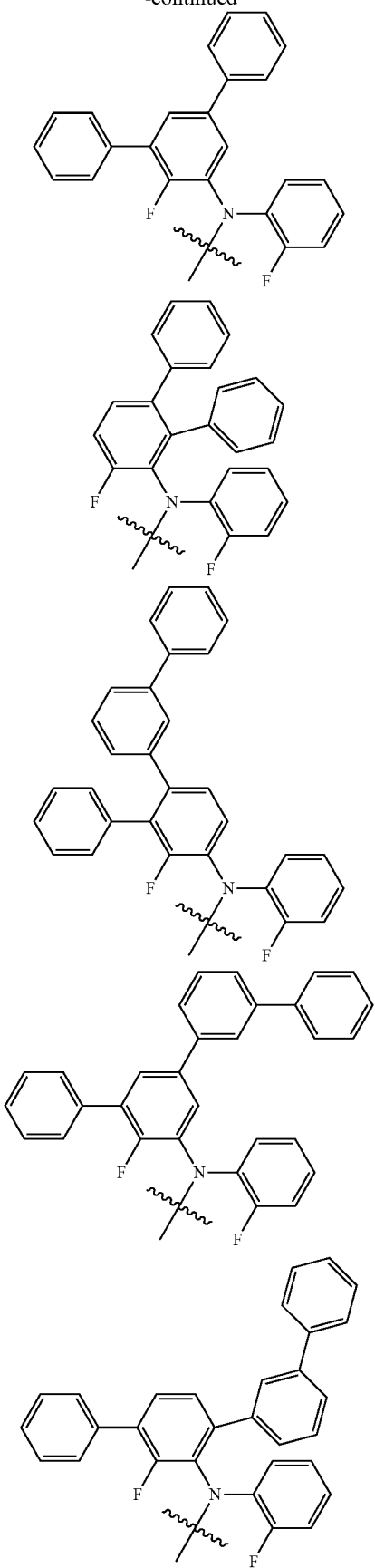

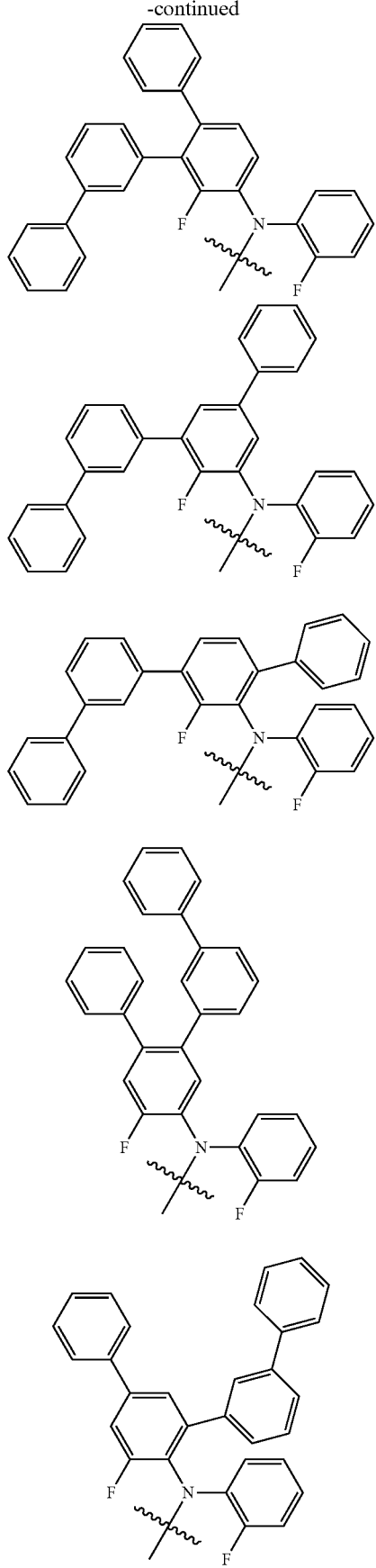
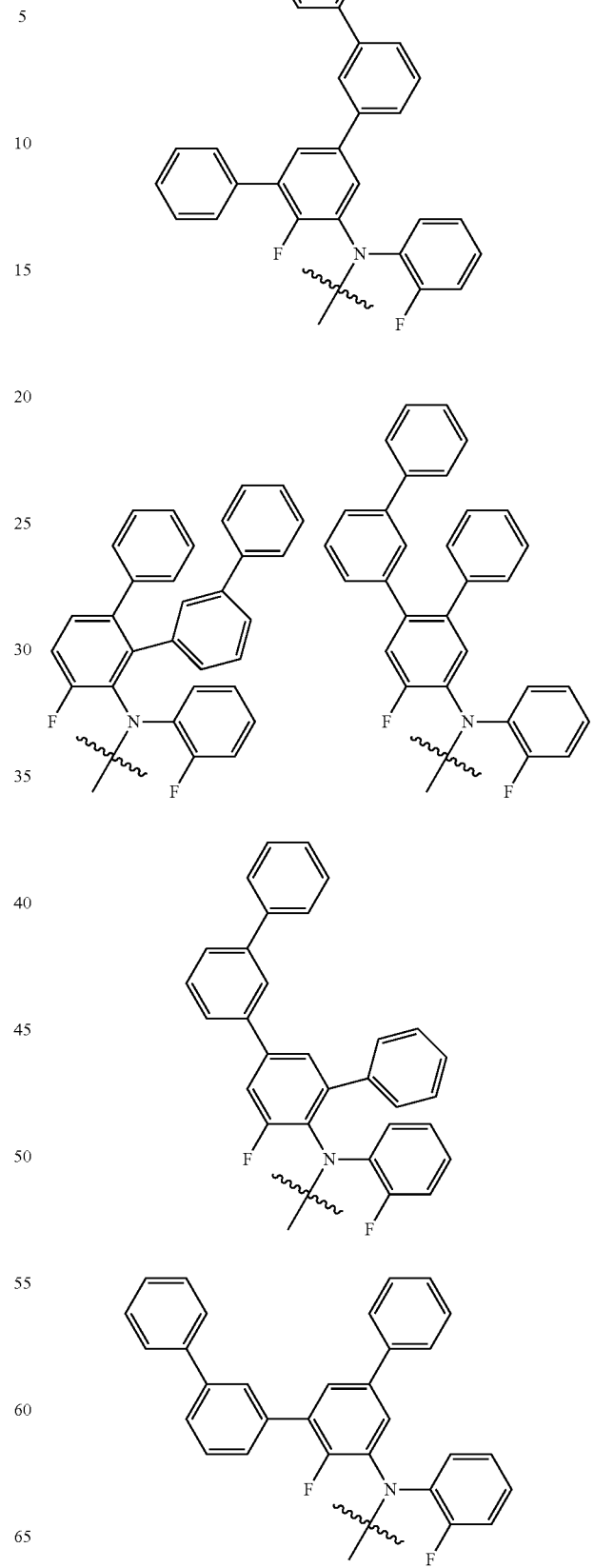

137
-continued
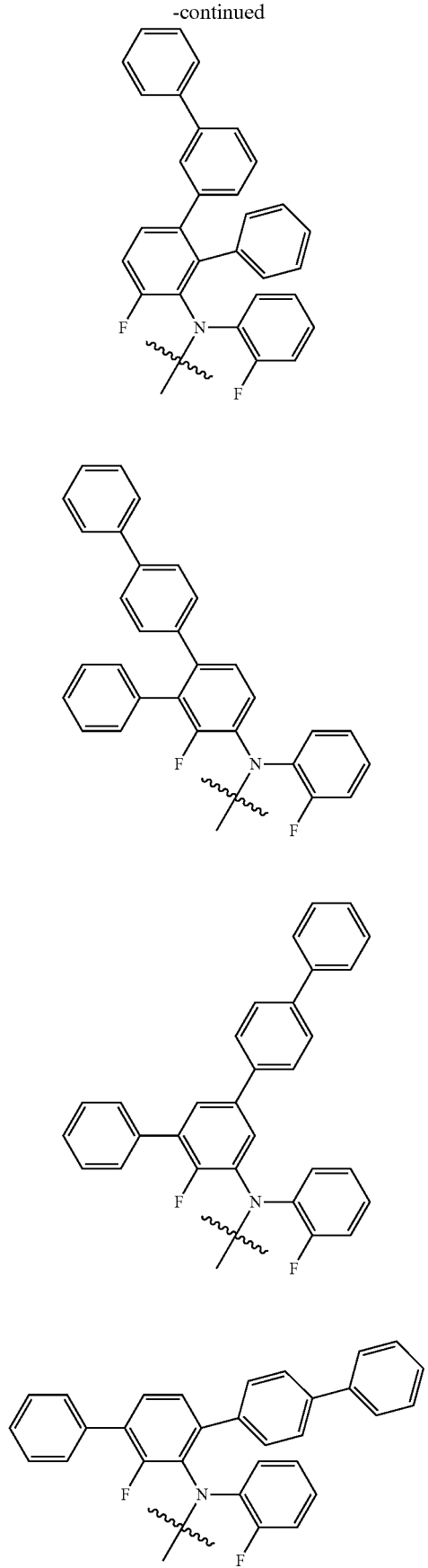
138
-continued
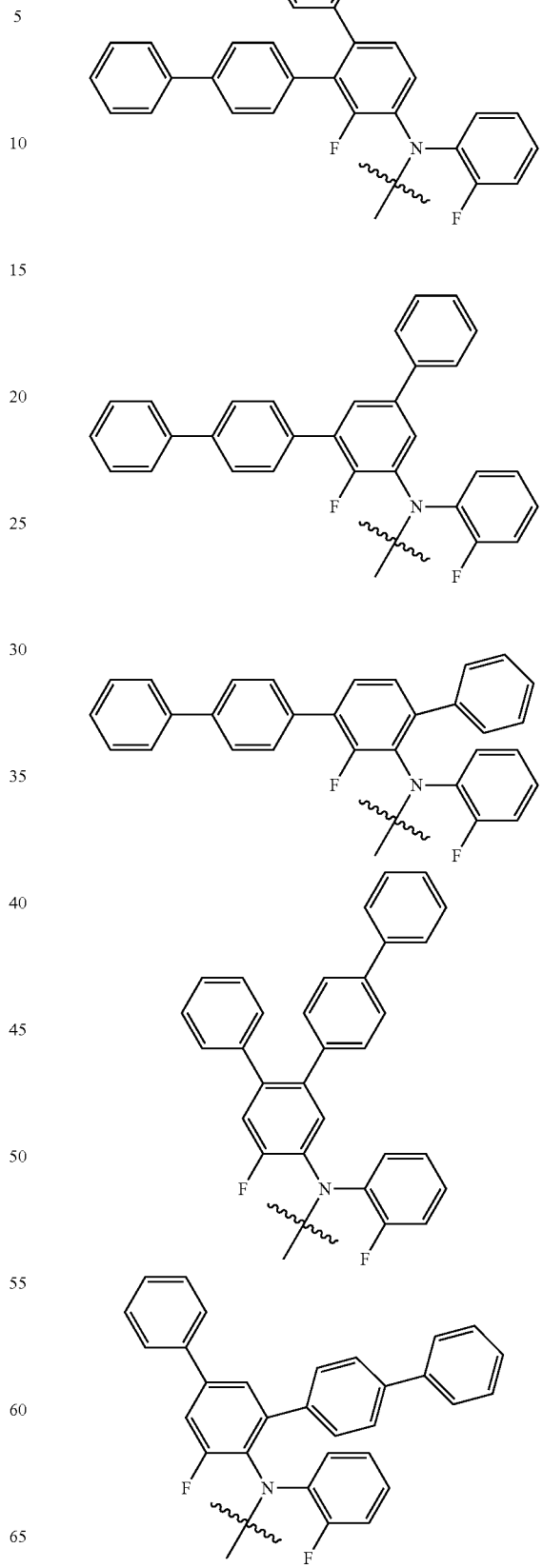

139
-continued
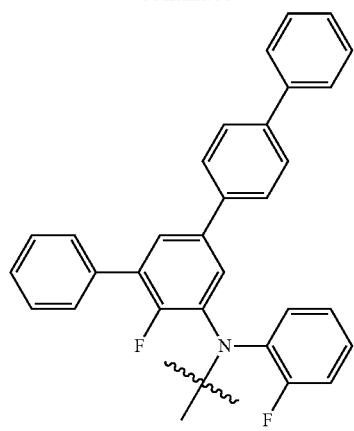
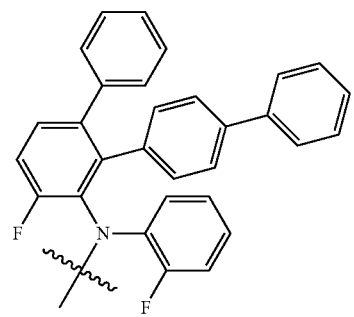
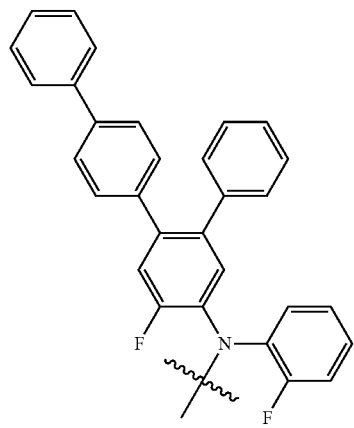
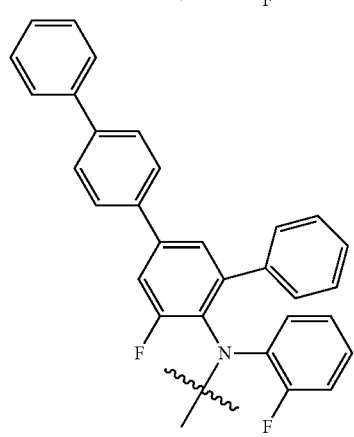
140
-continued
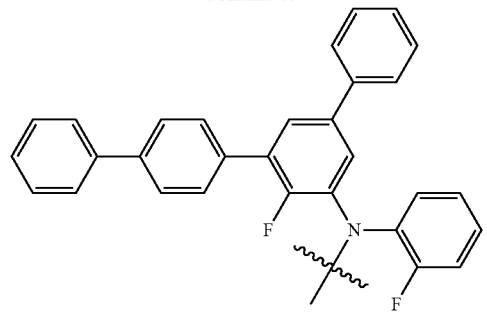
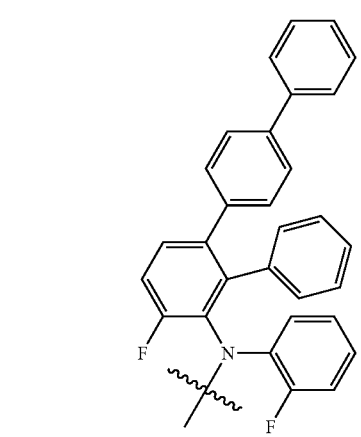
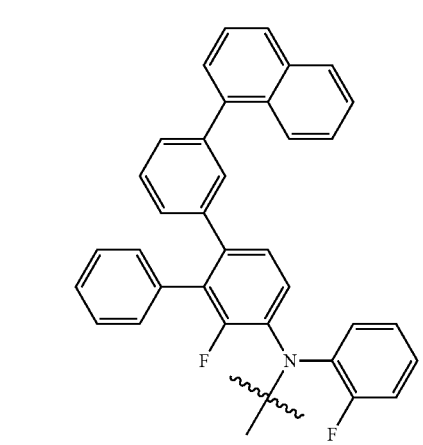
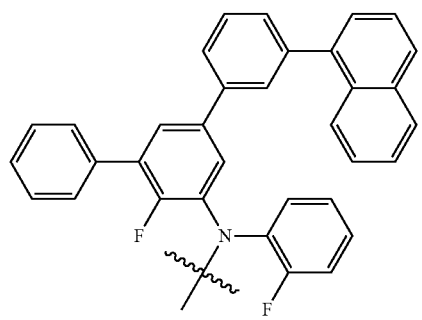

-continued
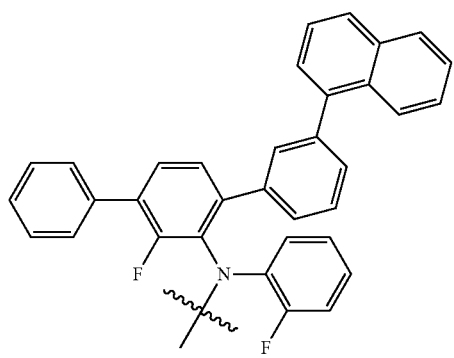
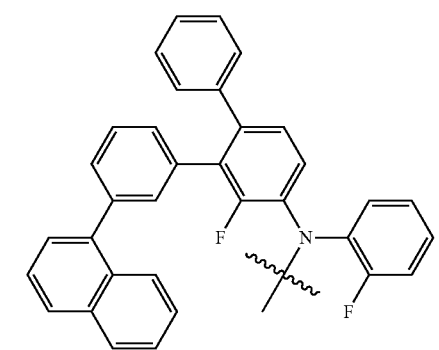
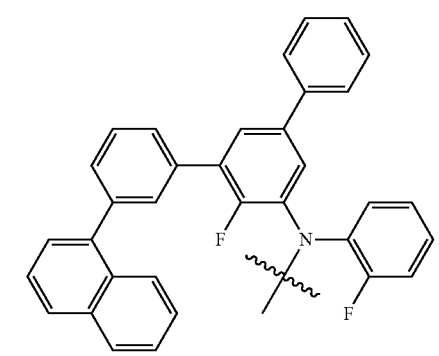
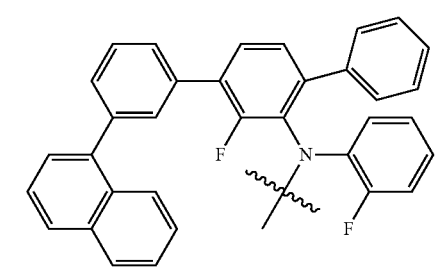
-continued
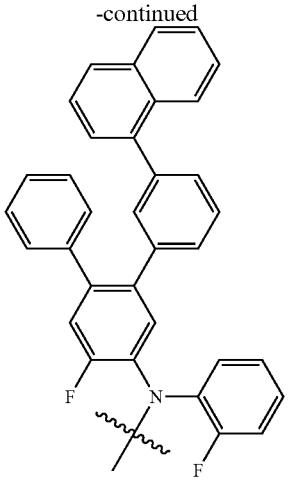
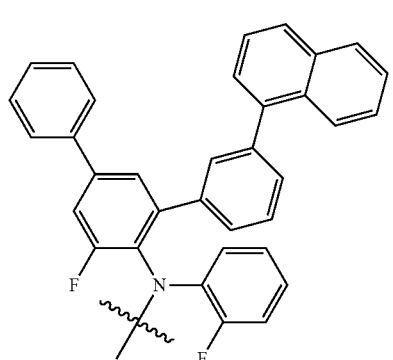
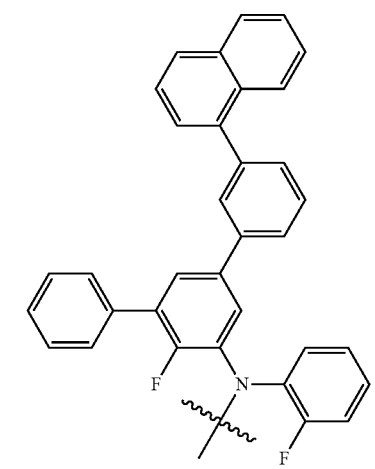
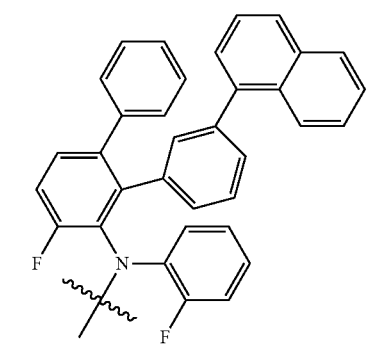

143
-continued
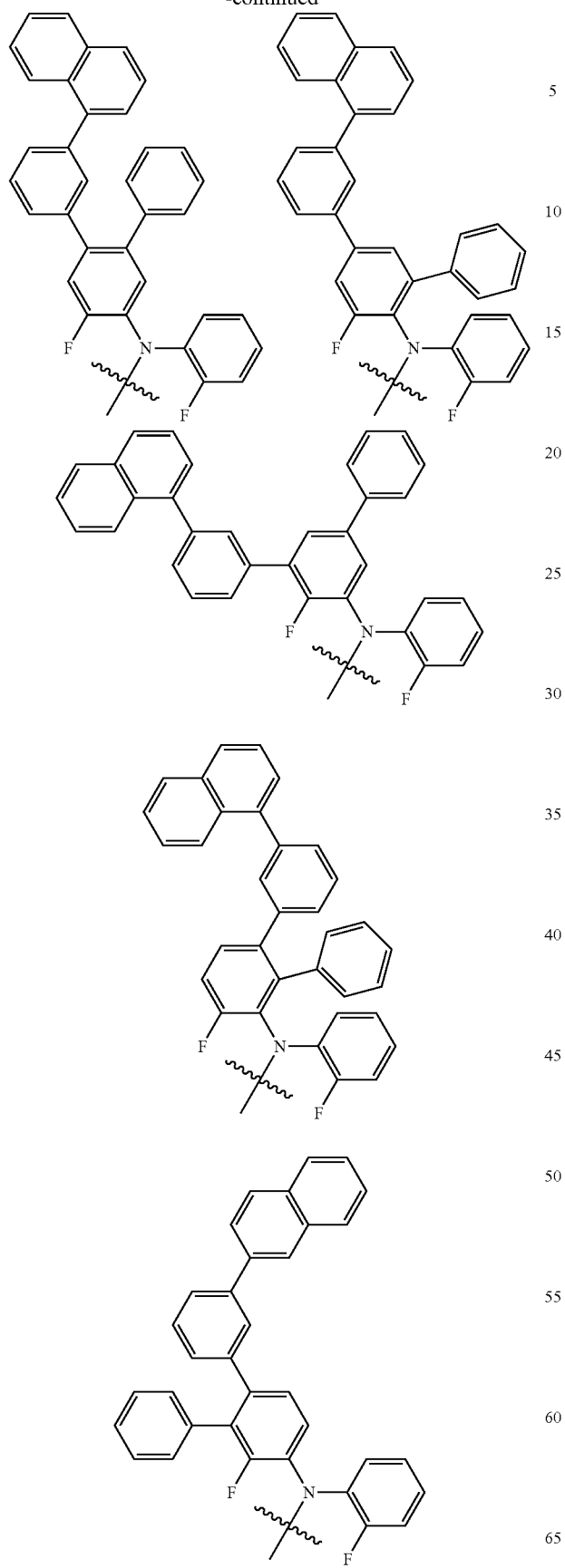
144
-continued
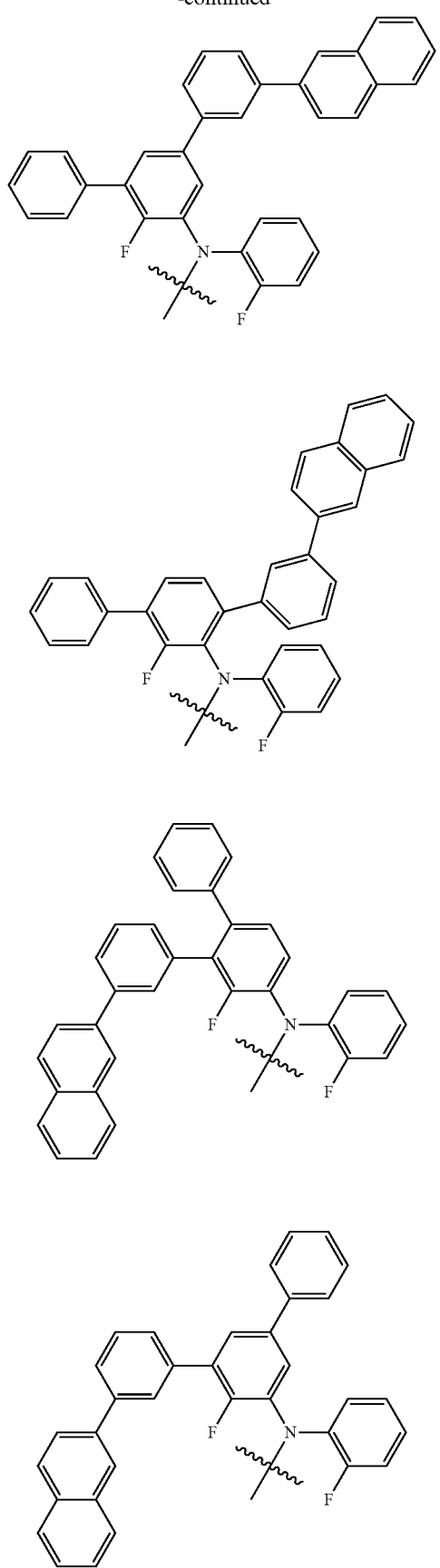

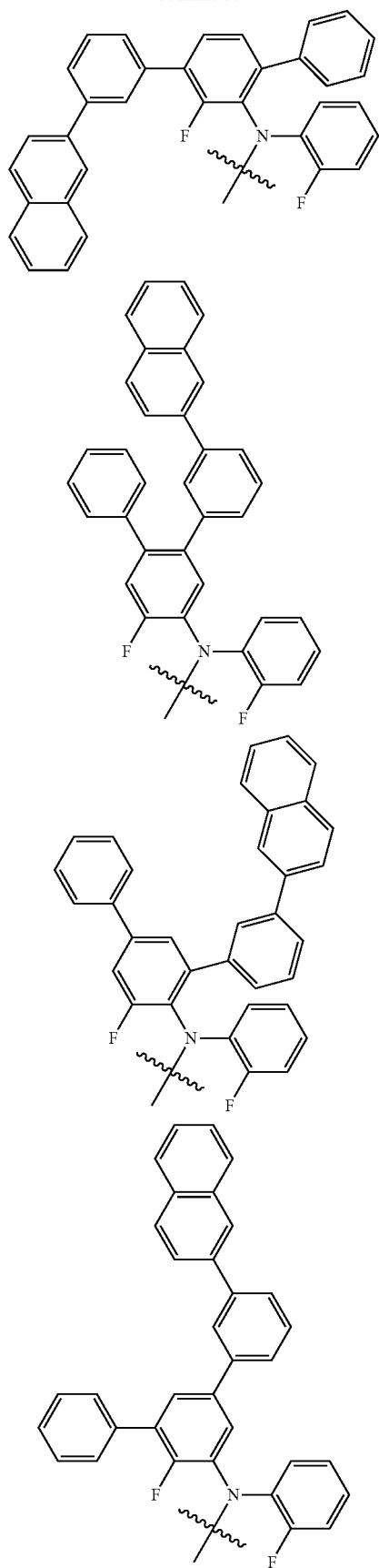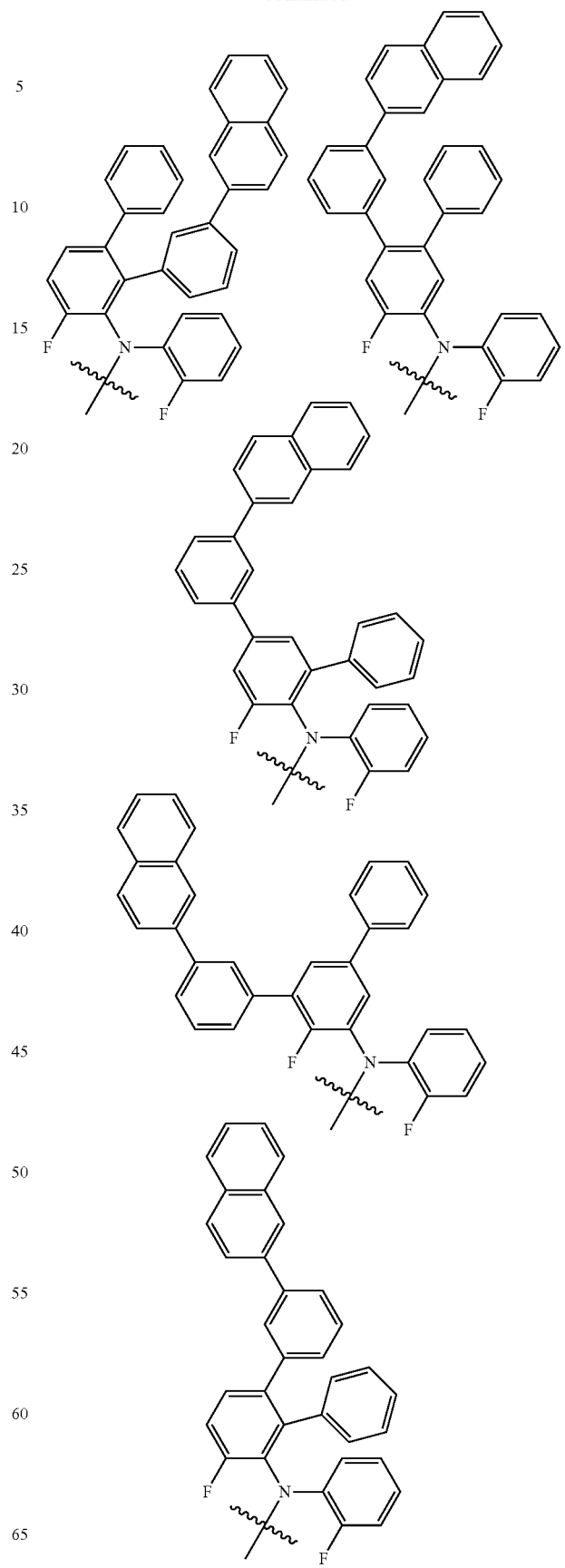

147
-continued
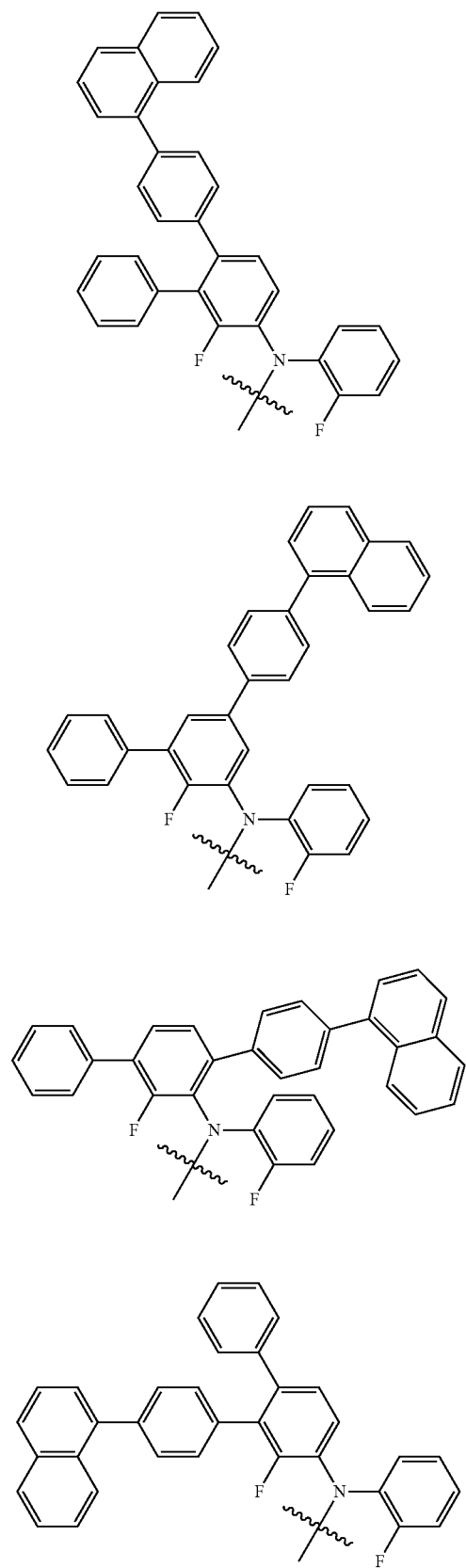
148
-continued
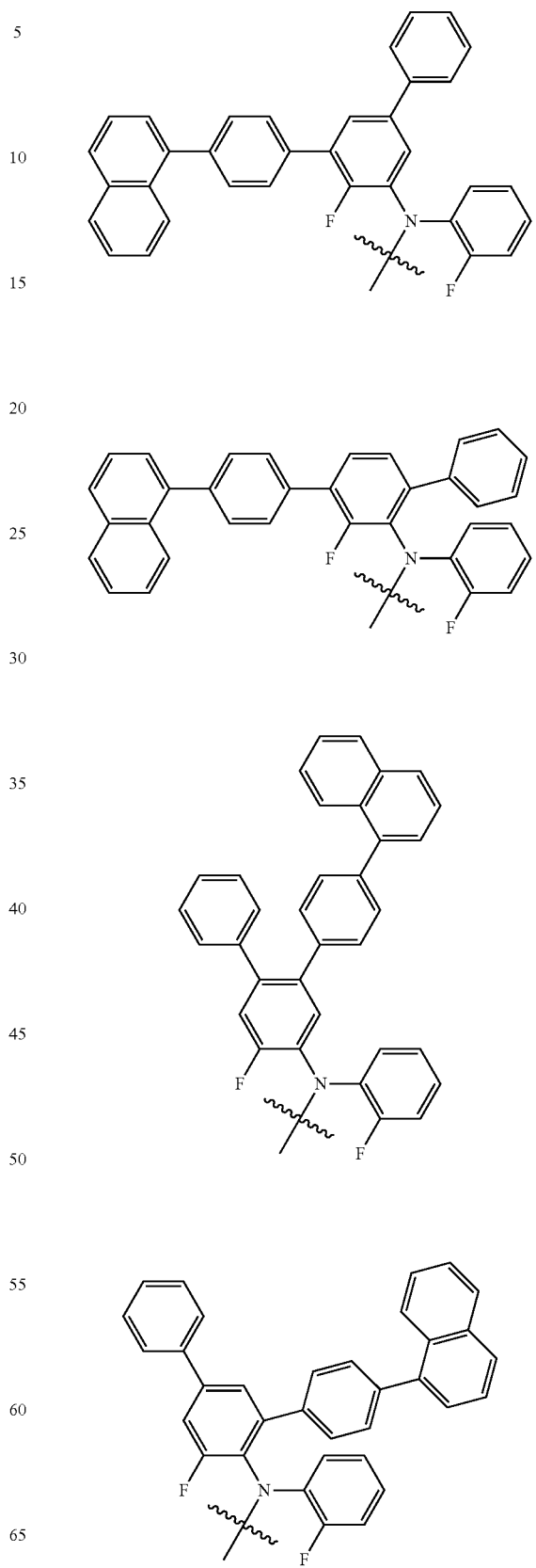

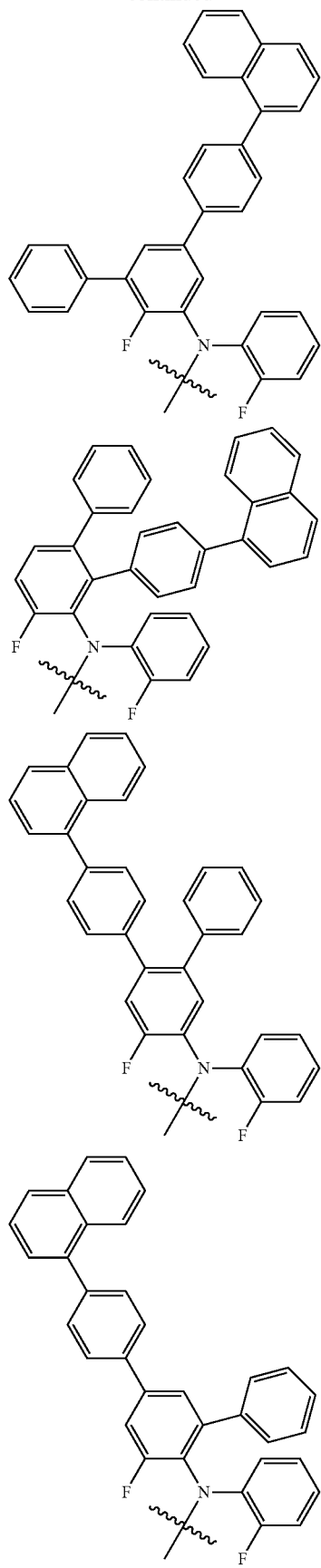
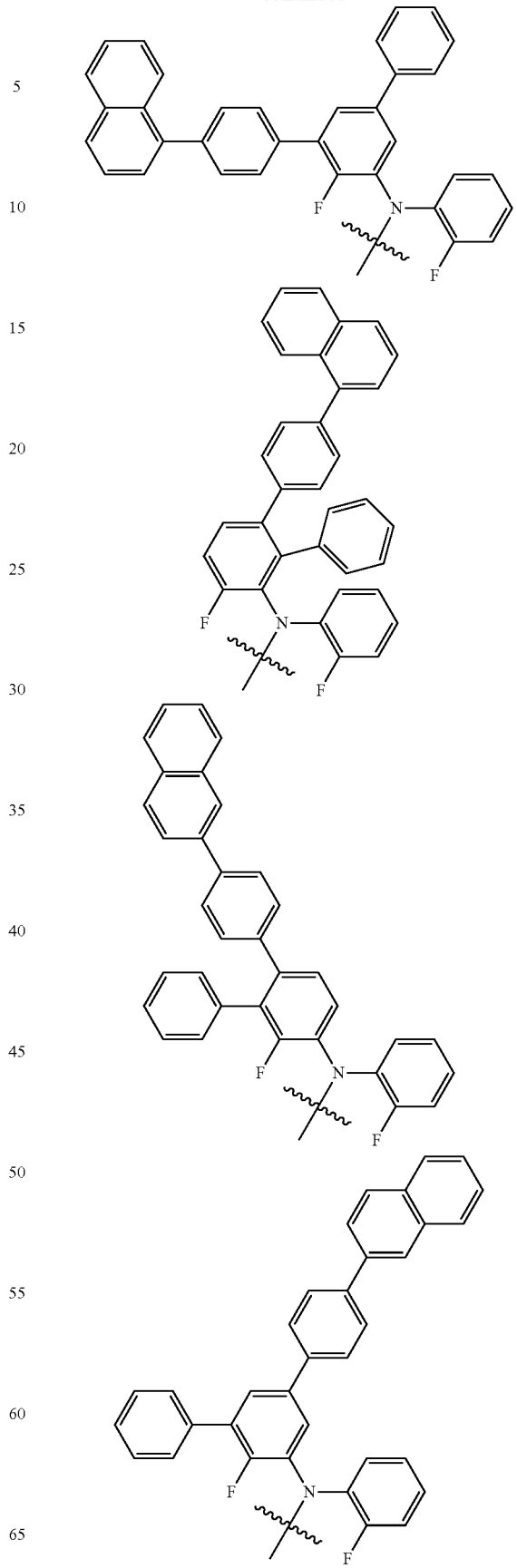

151
-continued
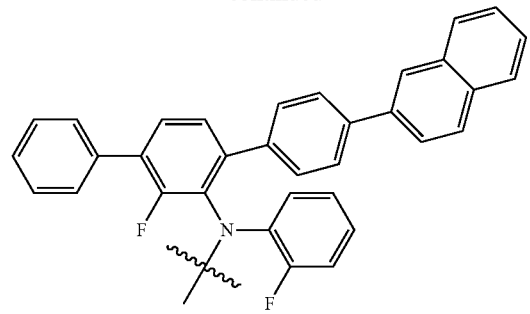
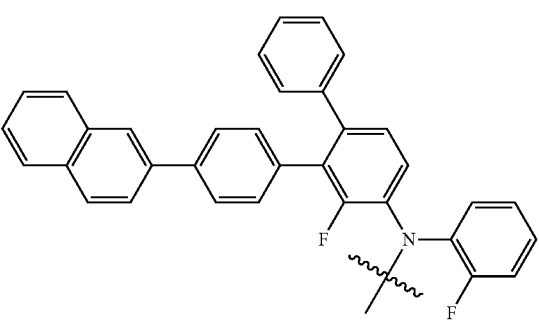
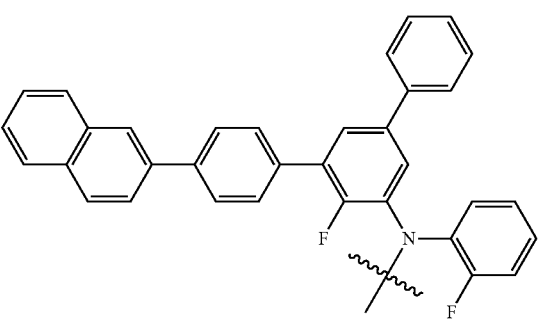
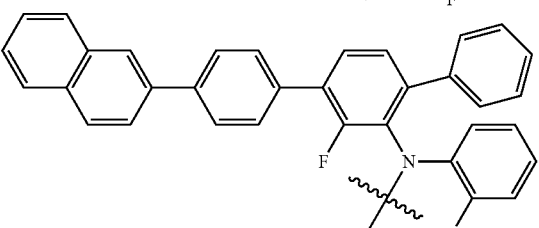
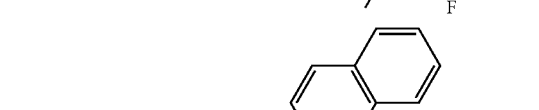
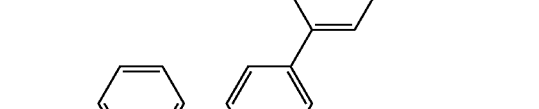
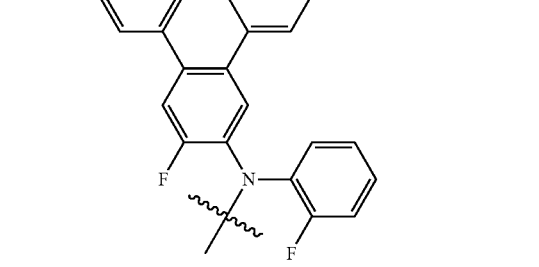
152
-continued
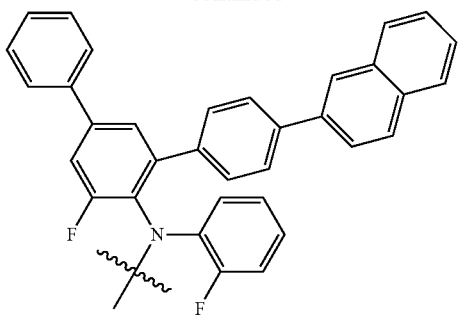
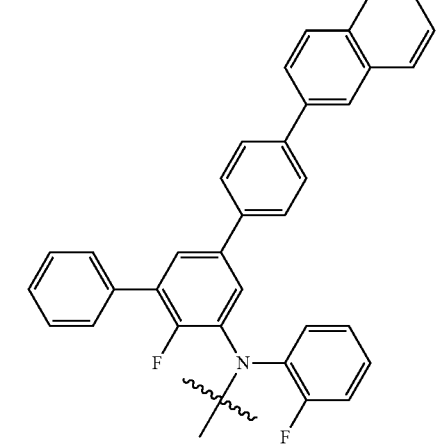
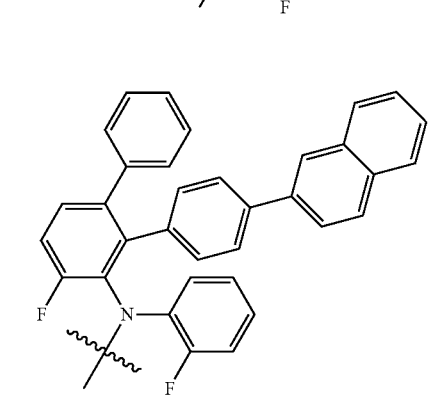
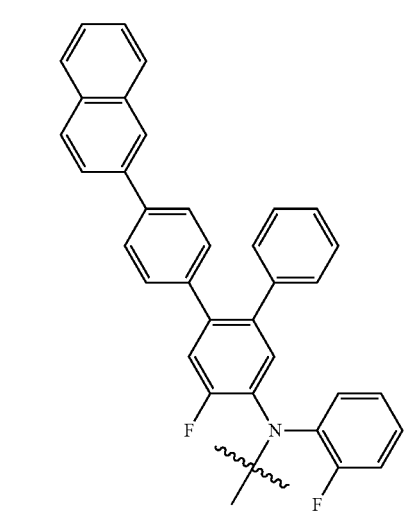

153
-continued
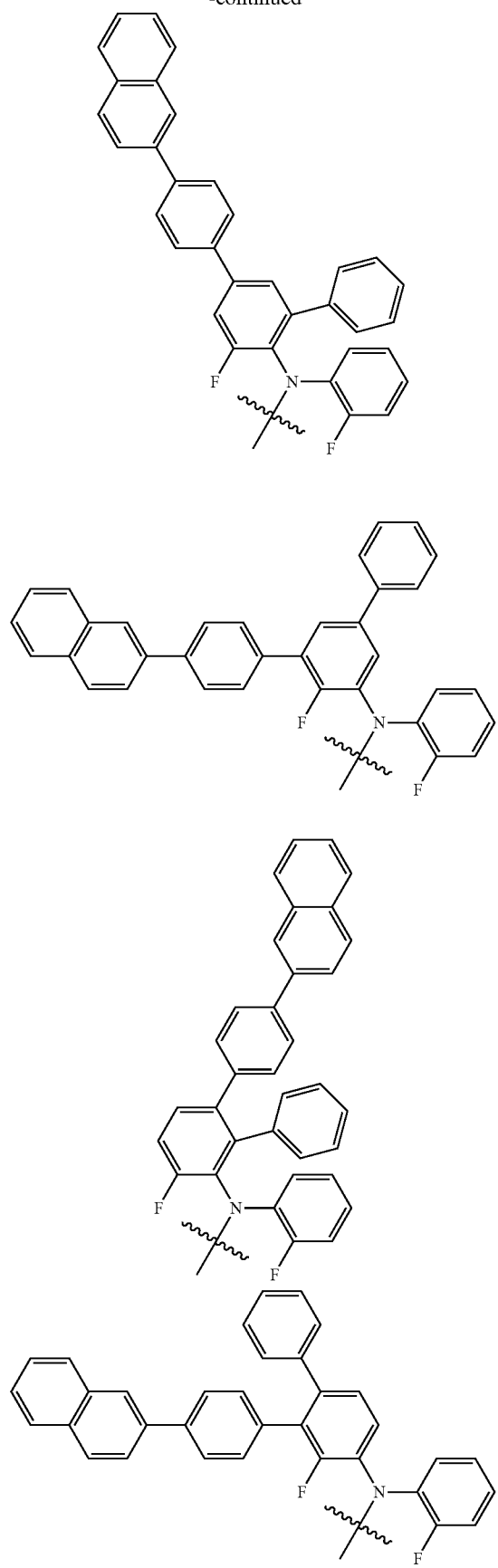
154
-continued
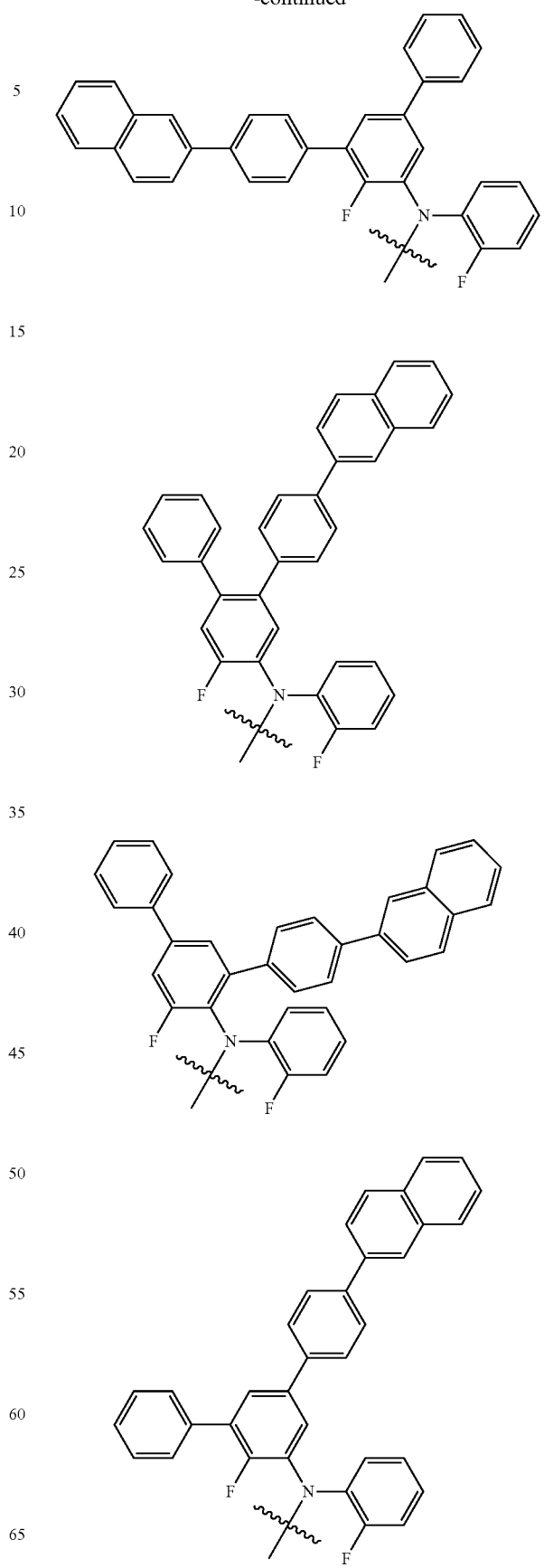

155
-continued
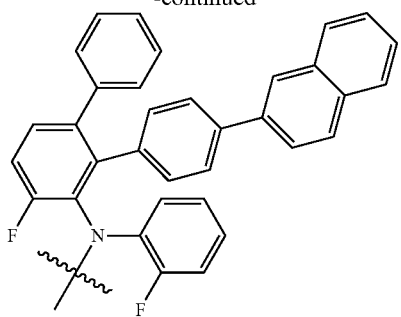
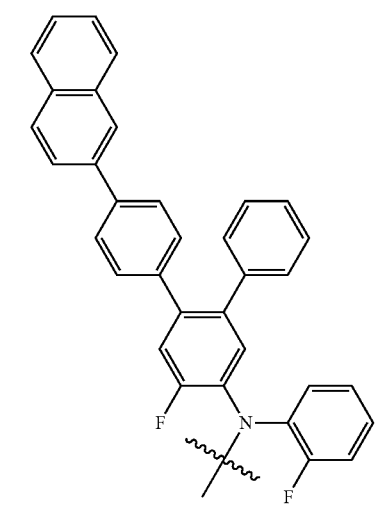
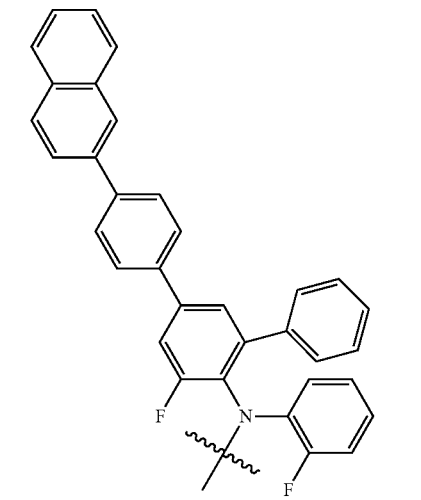
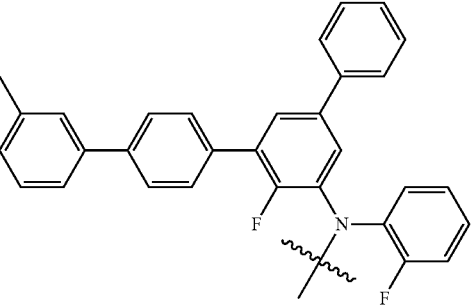
156
-continued
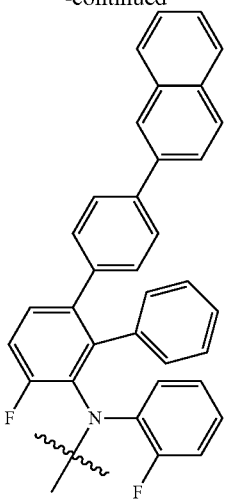
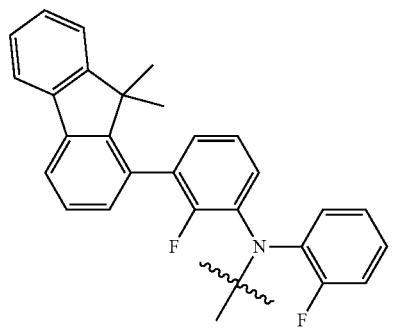
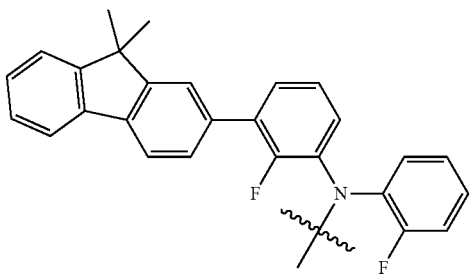
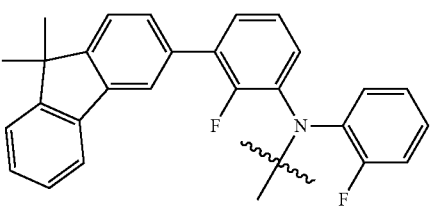
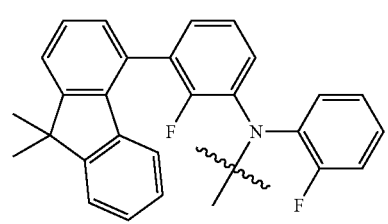

157
-continued
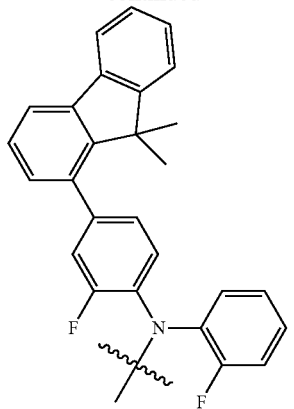
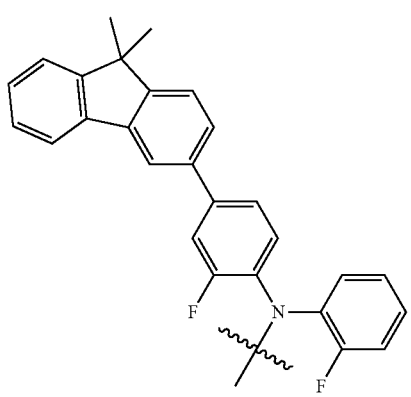
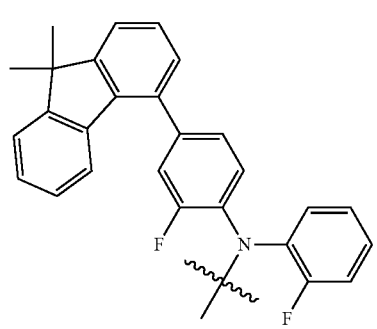
158
-continued
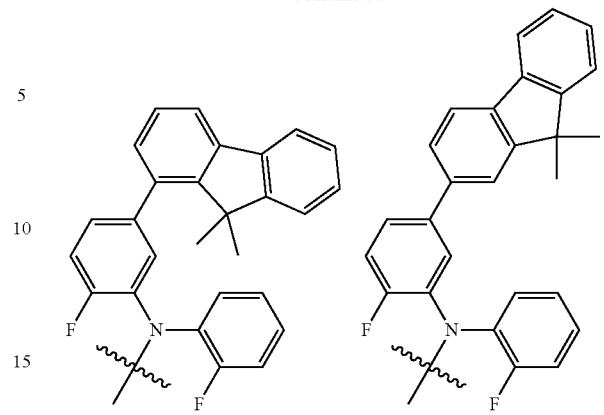
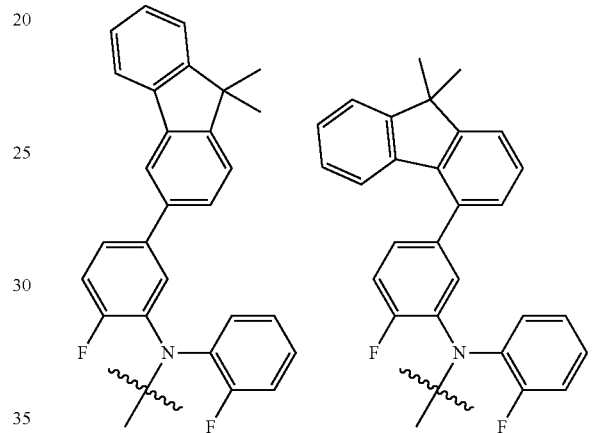
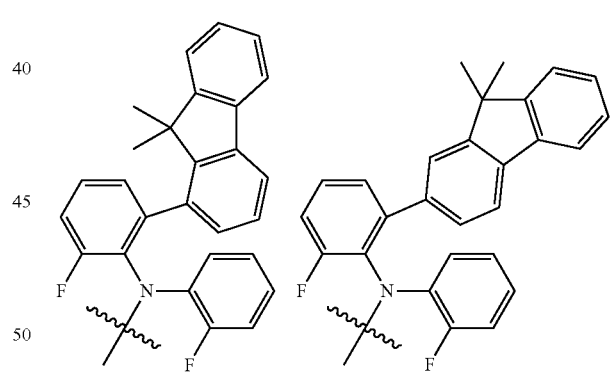
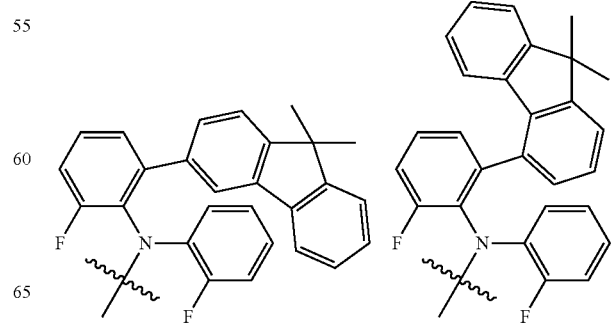

159
-continued
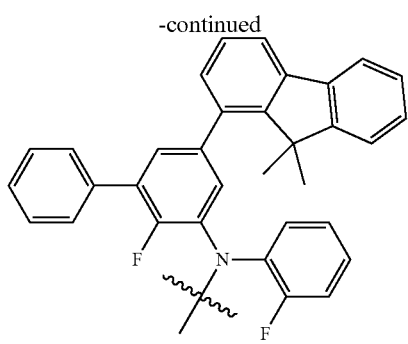
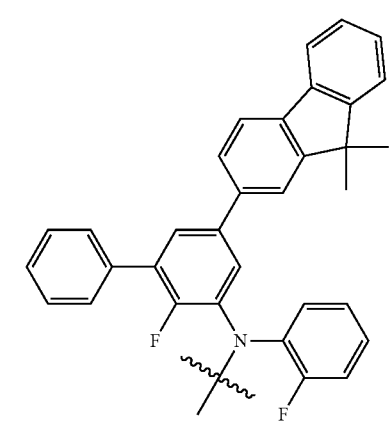
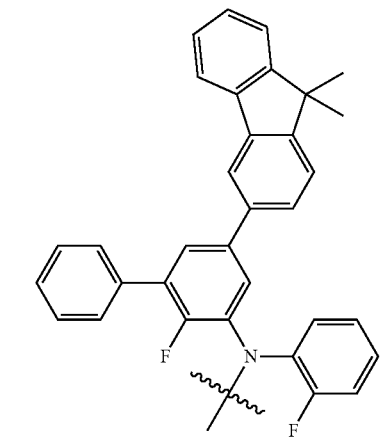
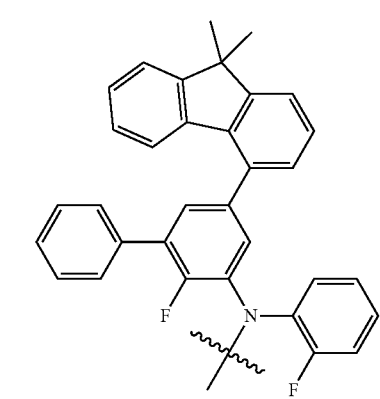
160
-continued
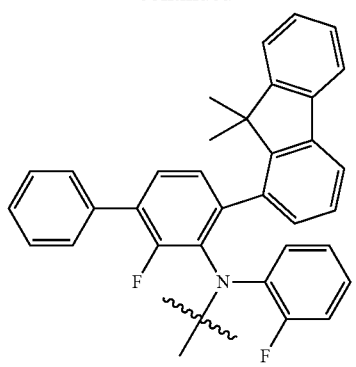
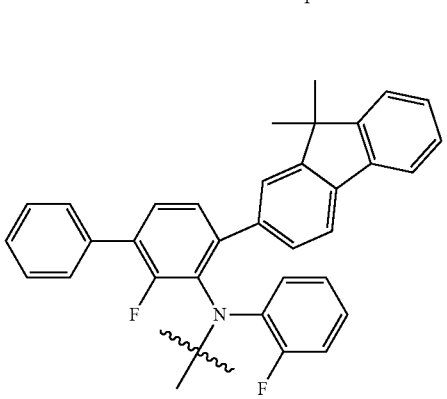
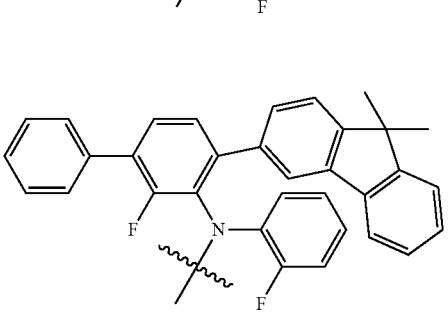
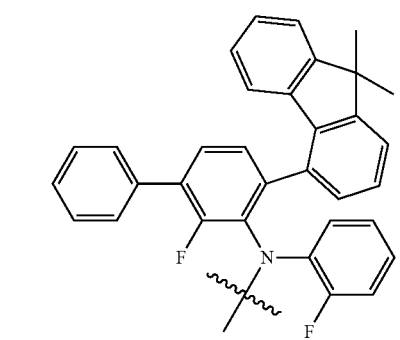
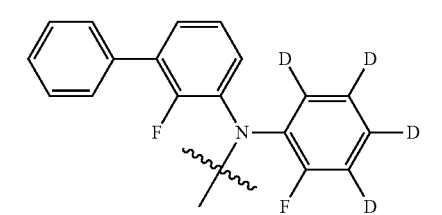

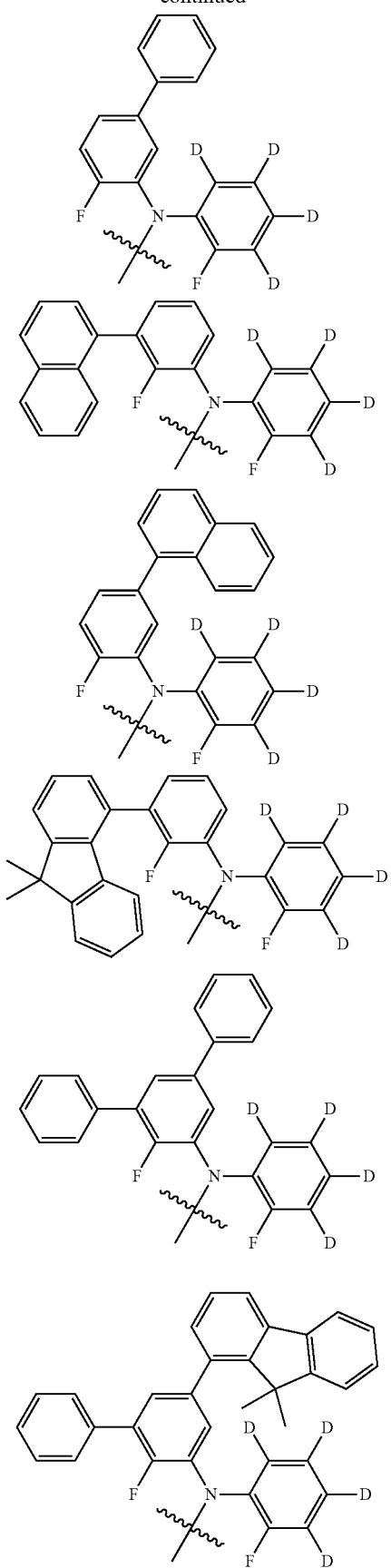
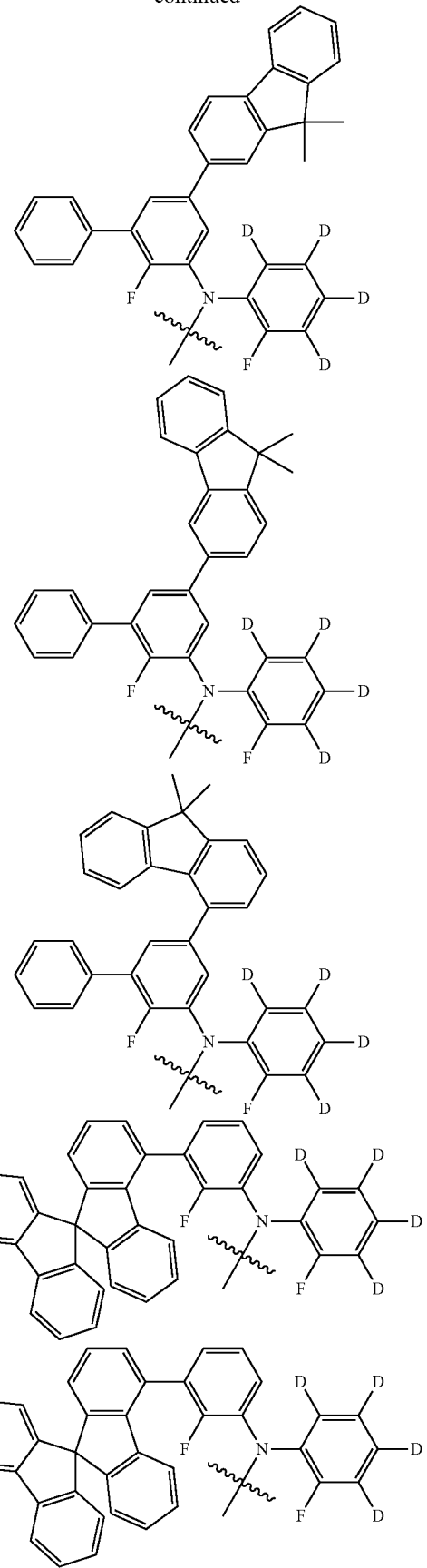

163
-continued
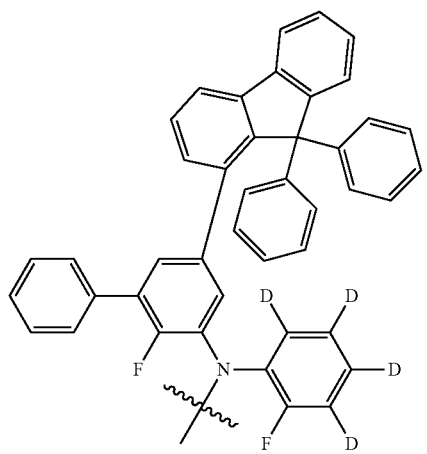
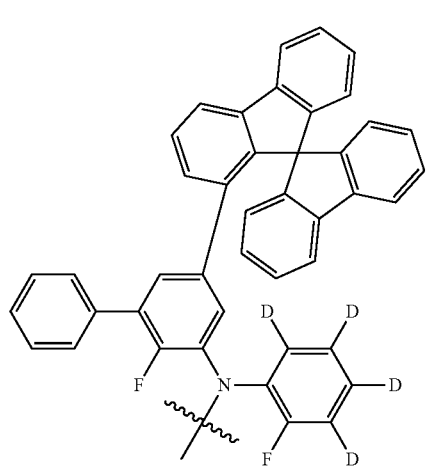
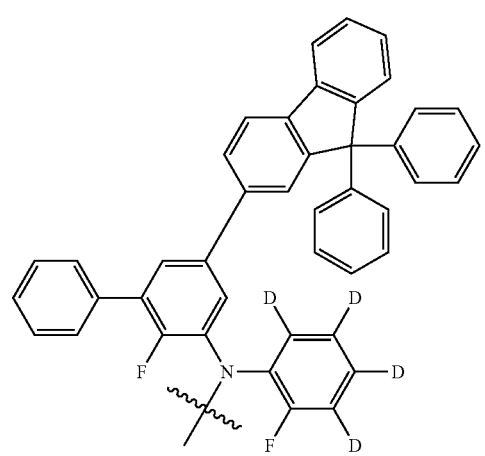
164
-continued
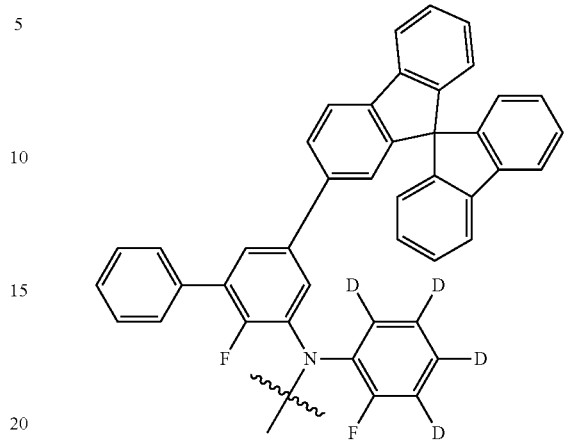
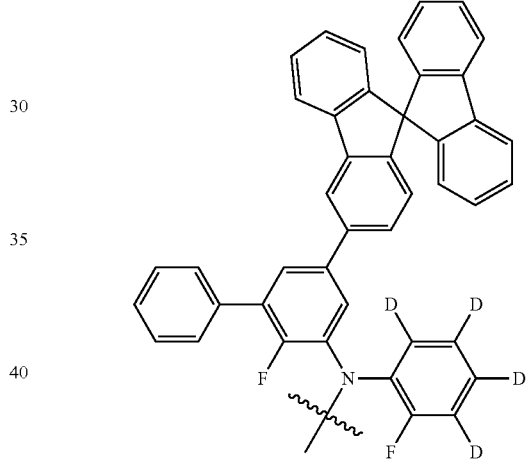
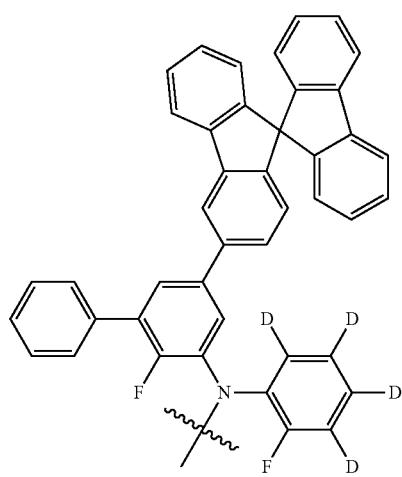

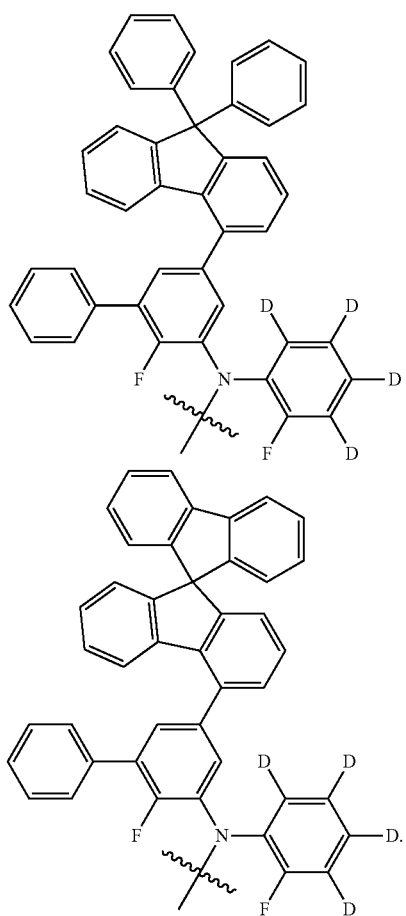
10. The pyrene-based compounds of claim 1, wherein, in Formula 1, the group represented by
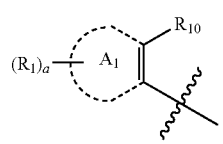
in the represented by
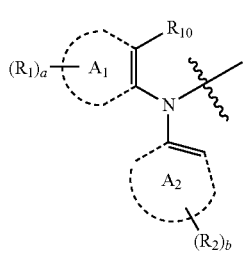
is selected from the groups represented by the following formulae:
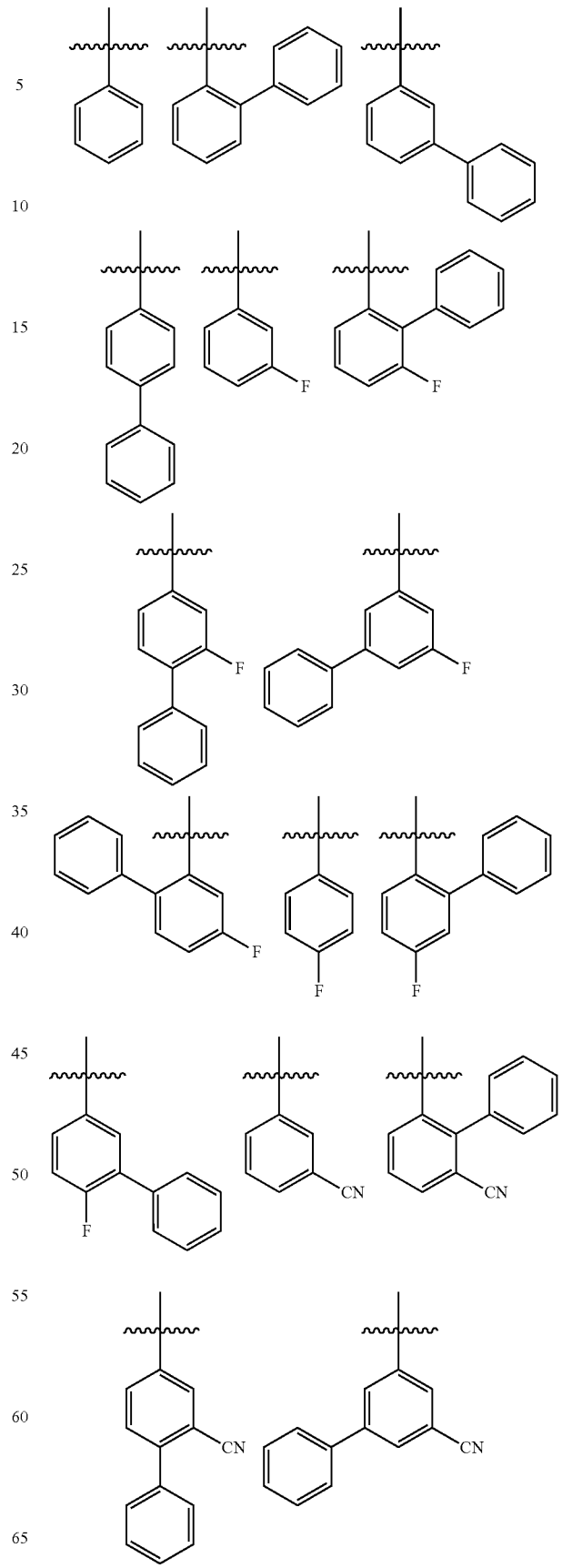

-continued
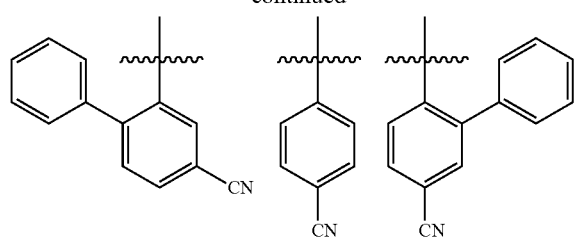
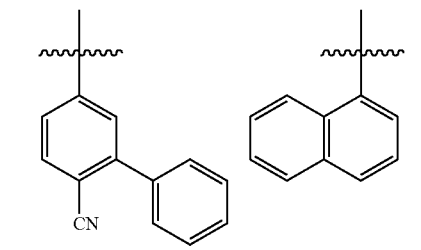
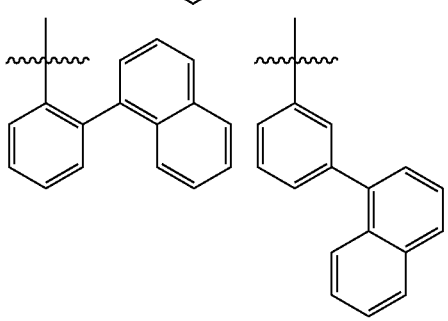
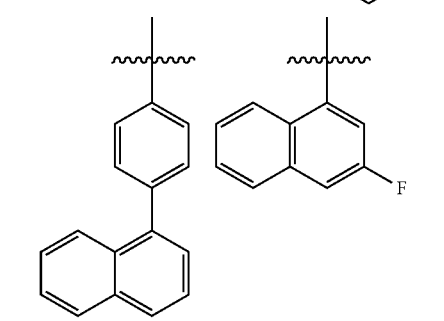
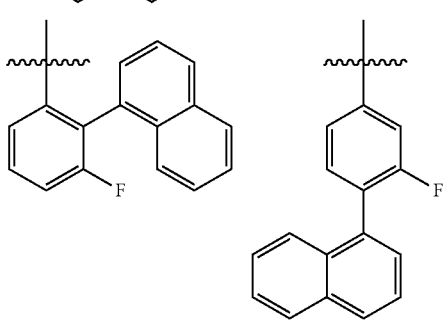
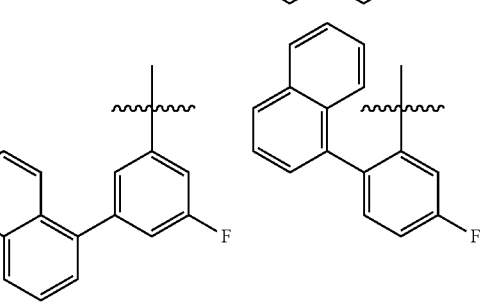
-continued
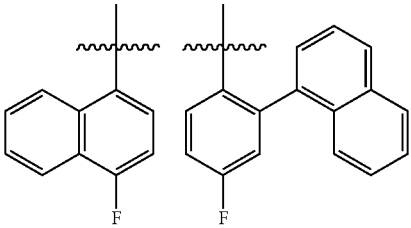
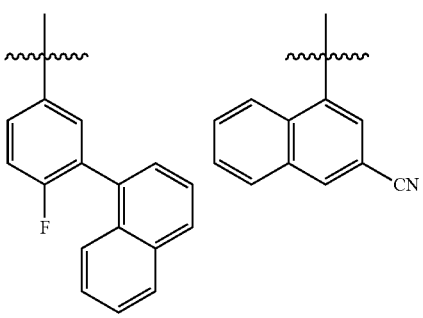
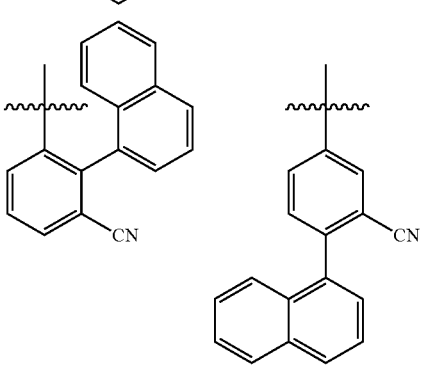
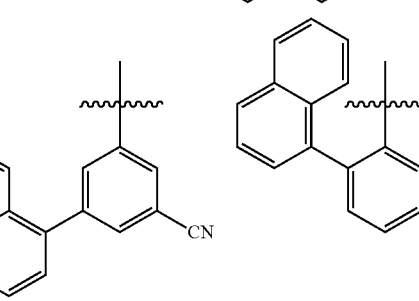
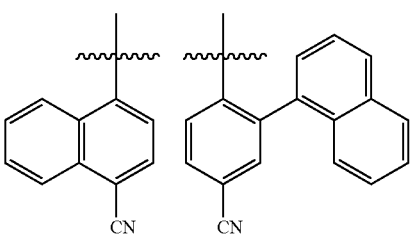
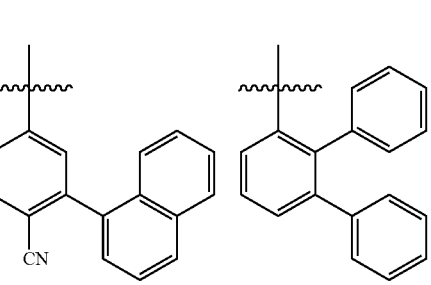

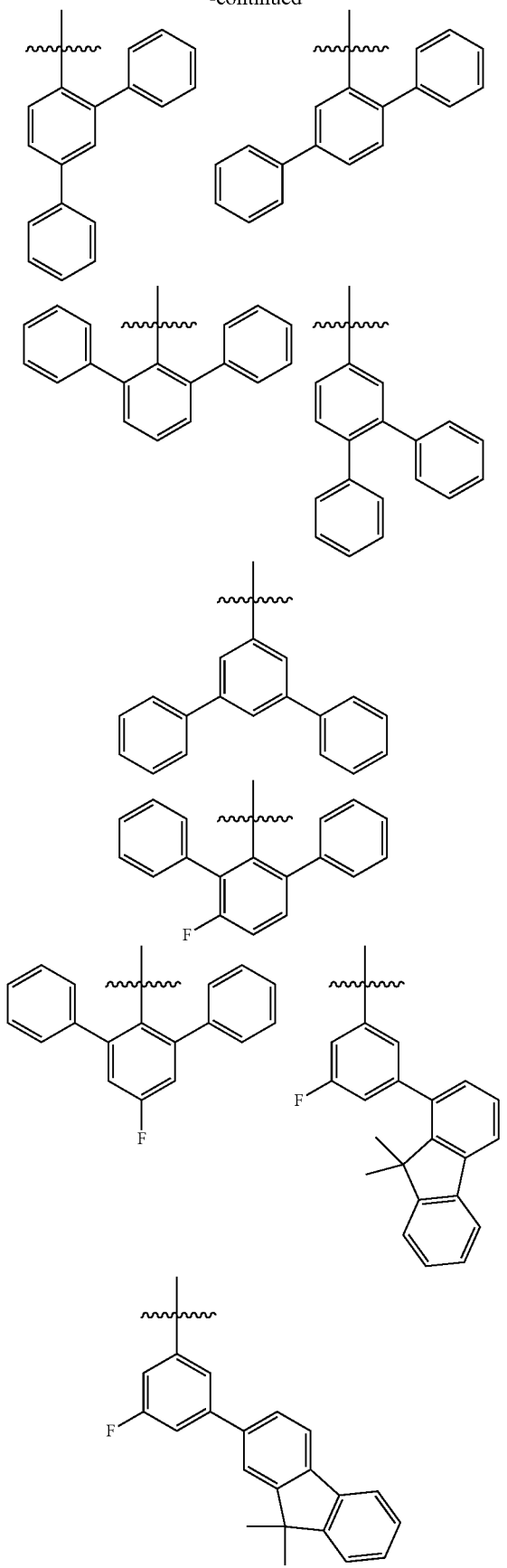
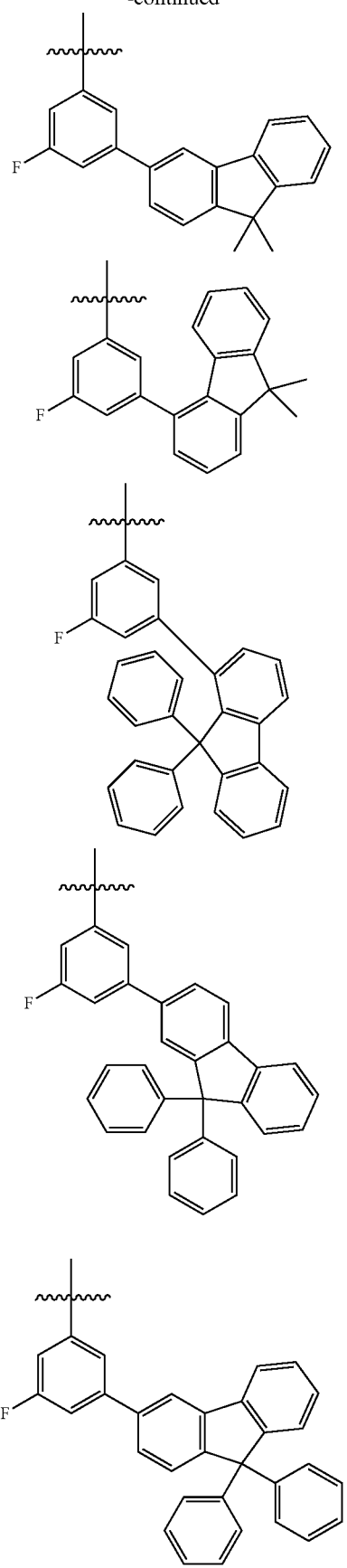

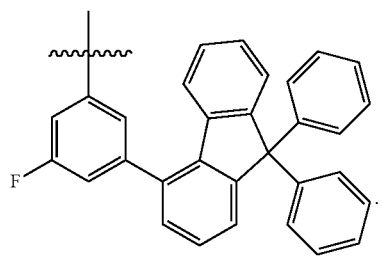
11. The pyrene-based compounds of claim 1, wherein, in Formula 1, the group represented by
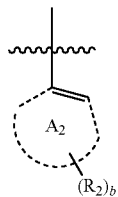
in the group represented by
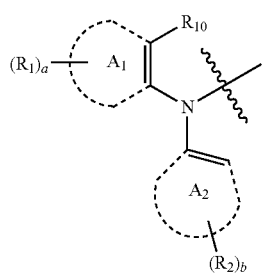
is selected from the groups represented by the following formulae:
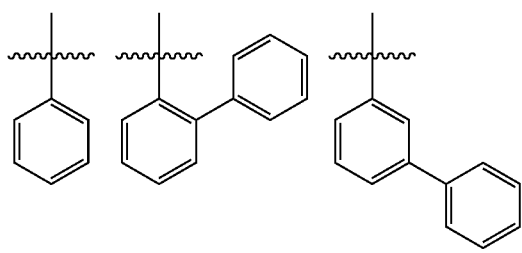
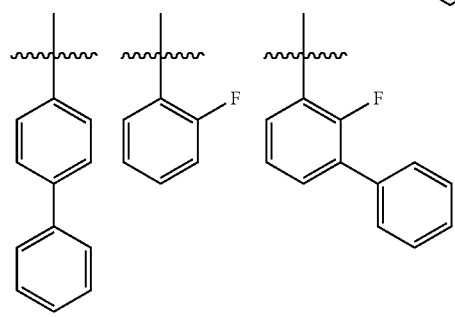
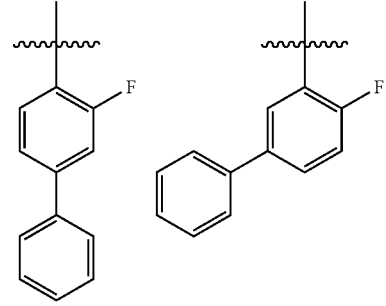
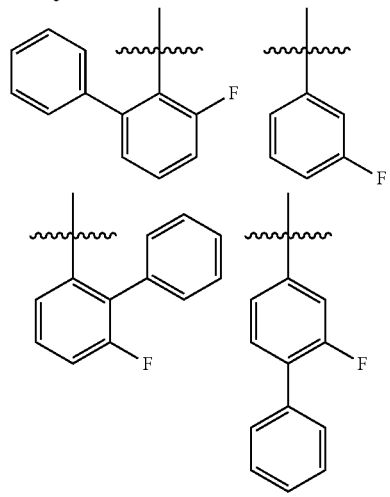
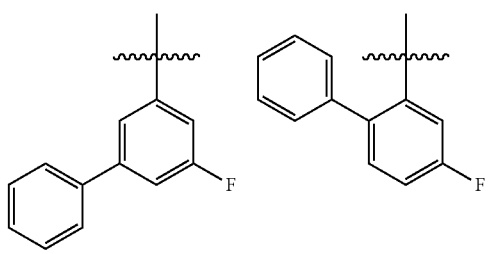
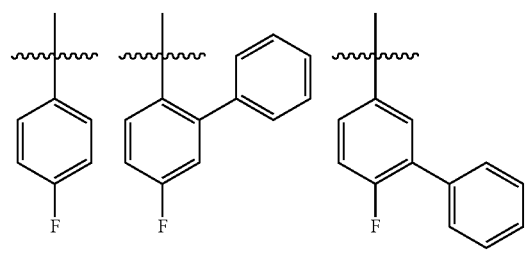
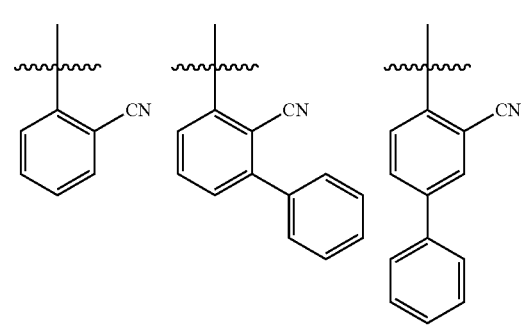

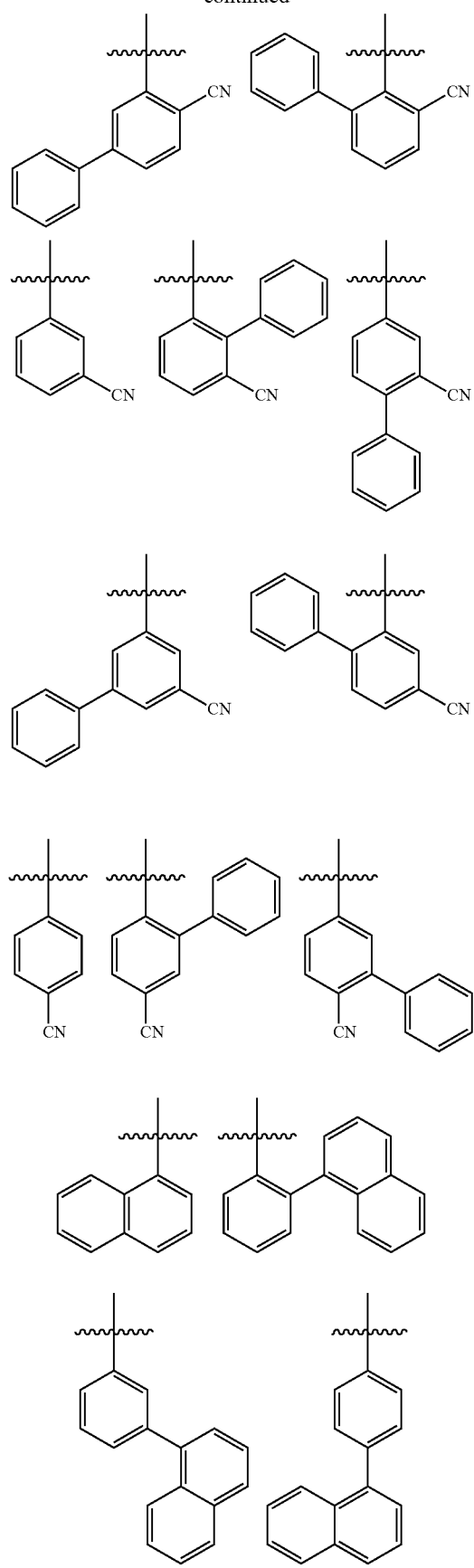
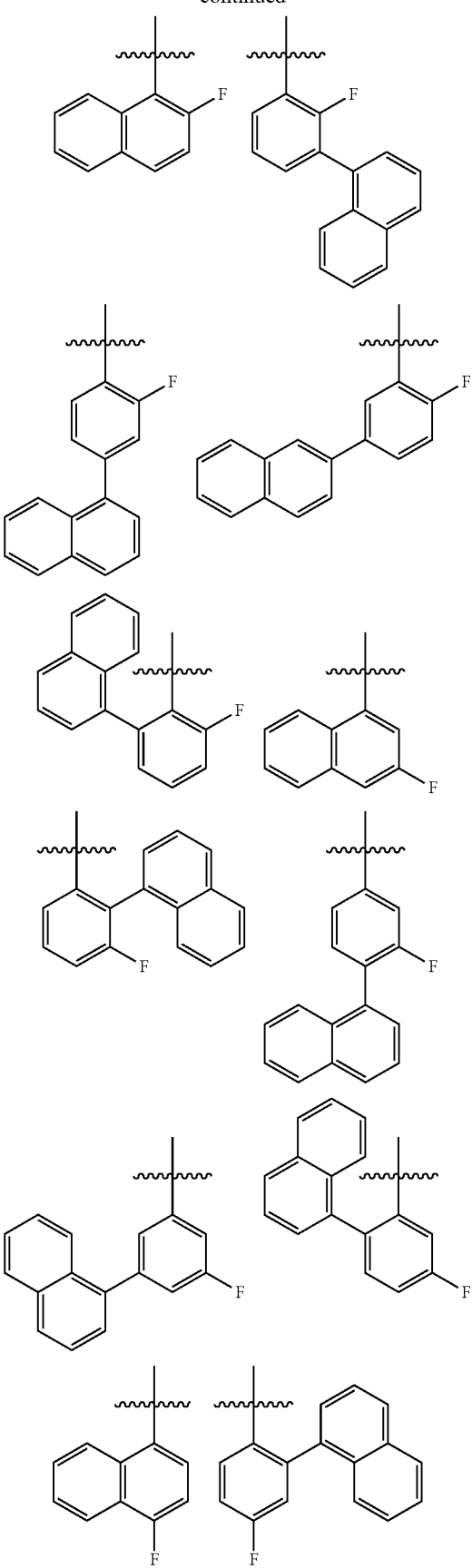

-continued
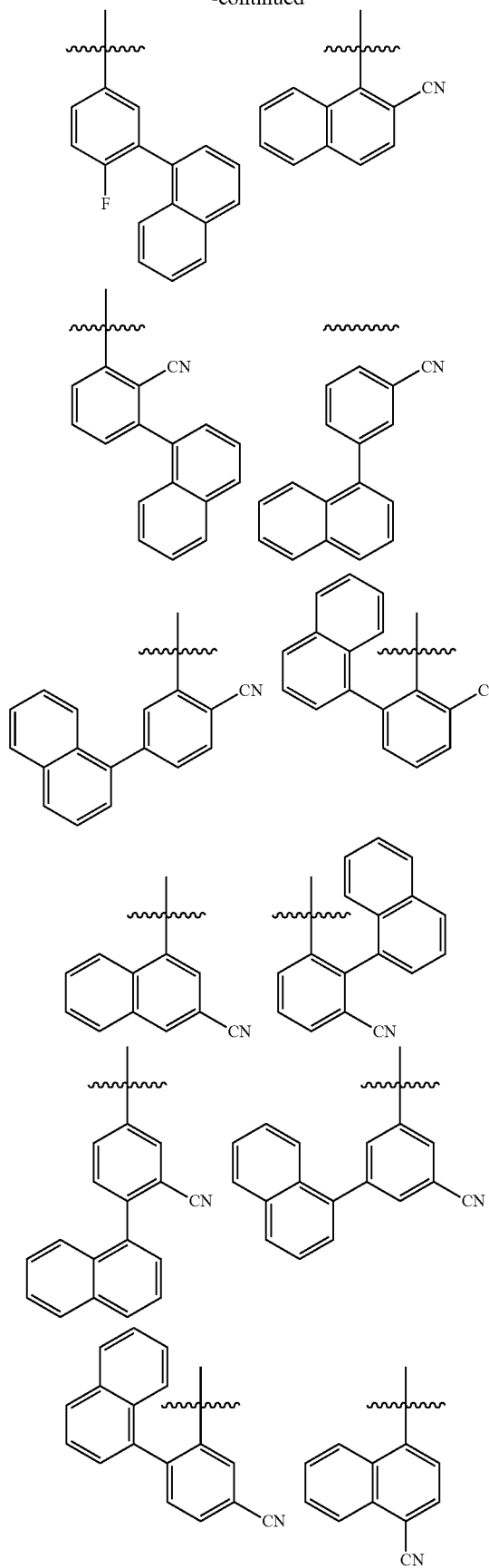
-continued
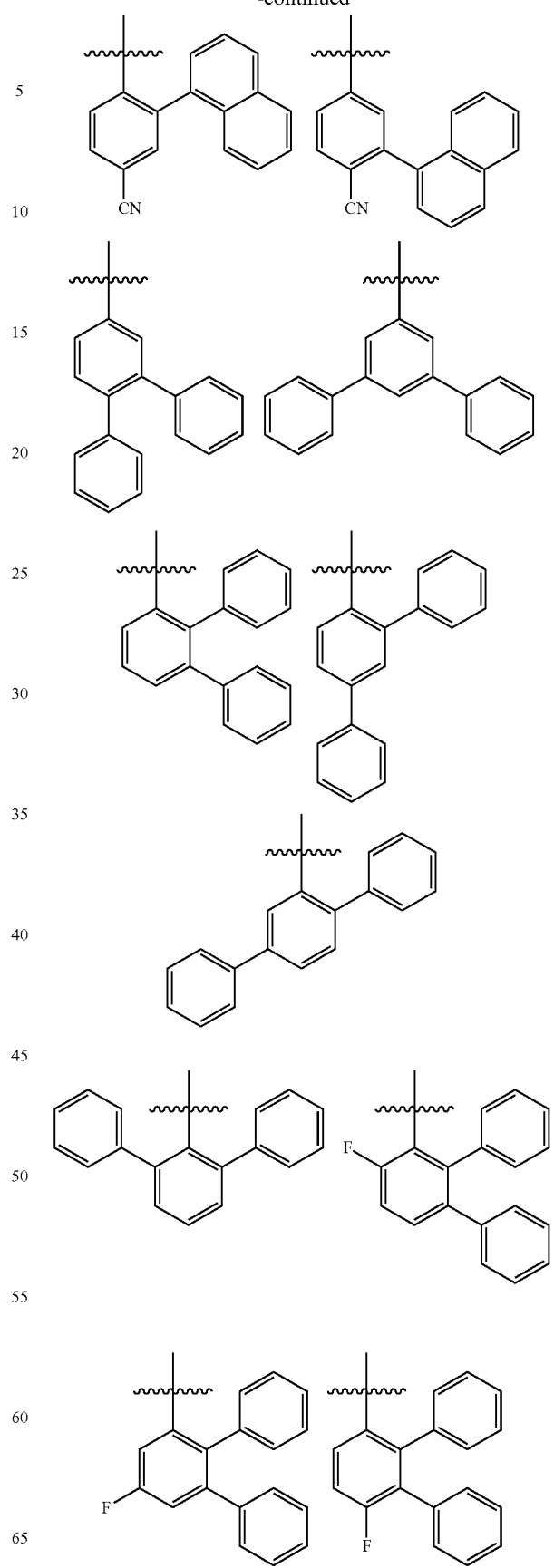

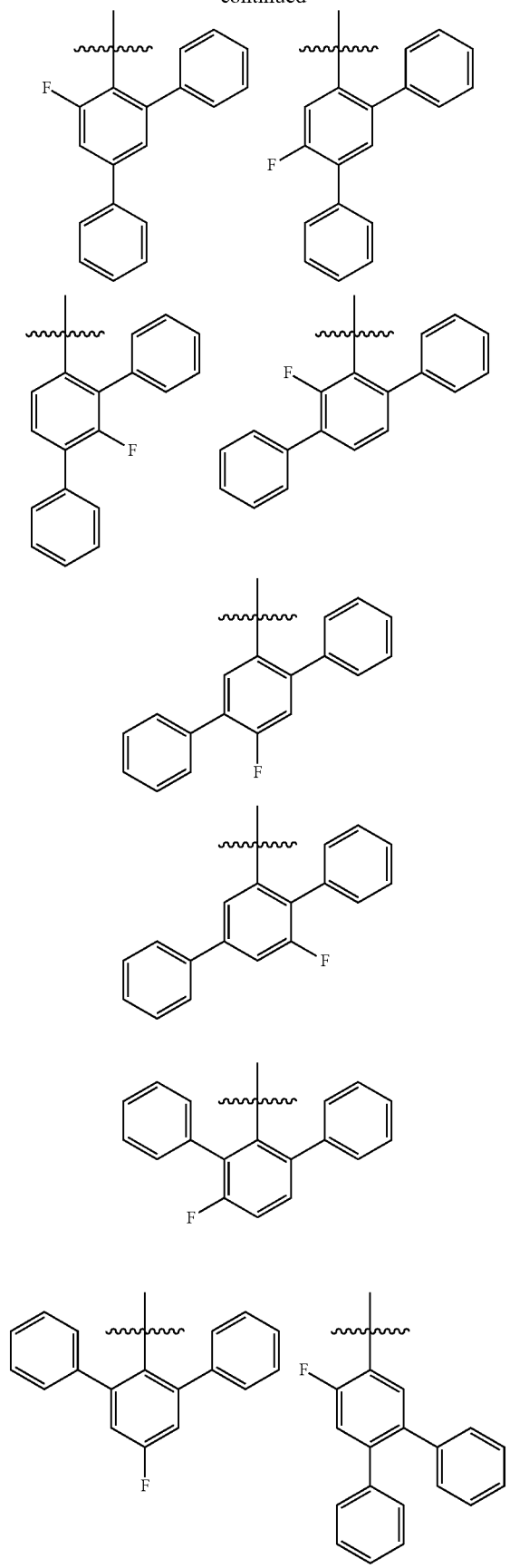
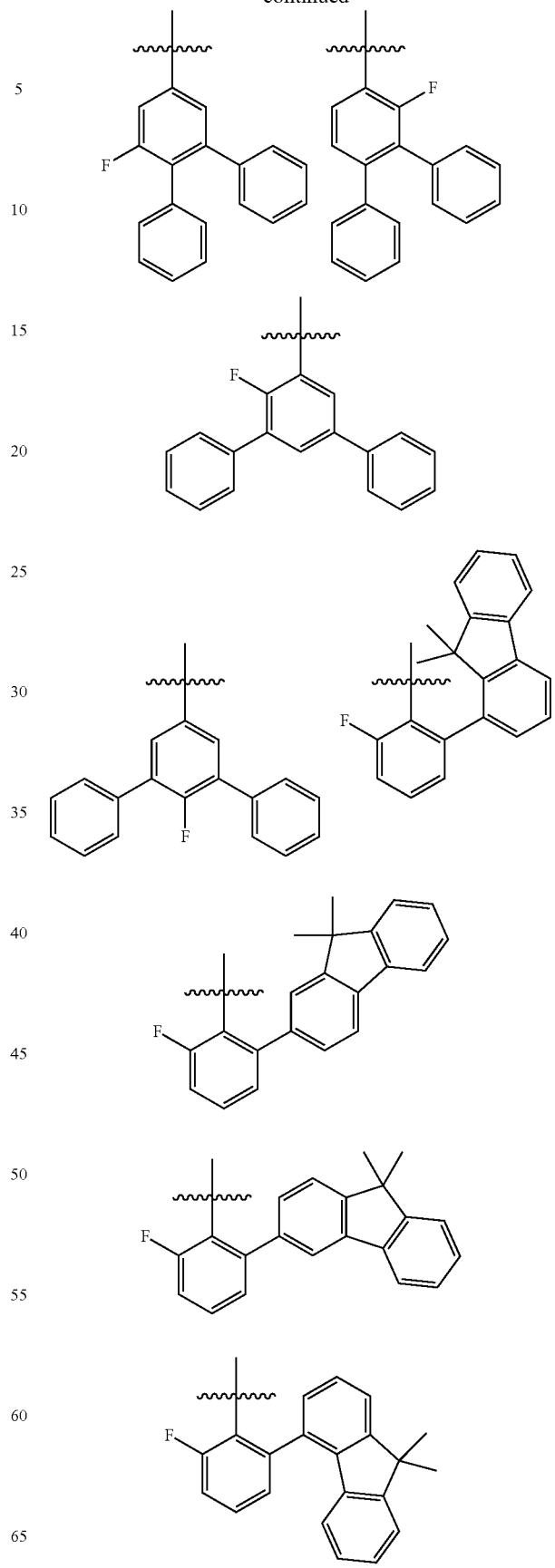

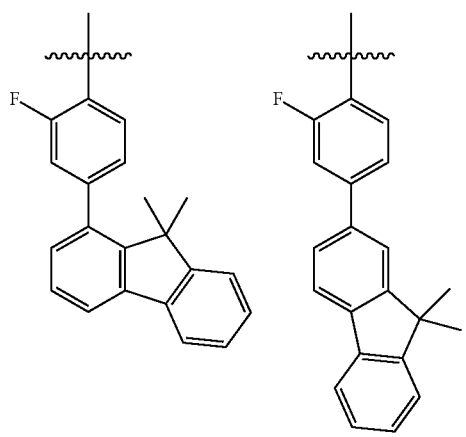
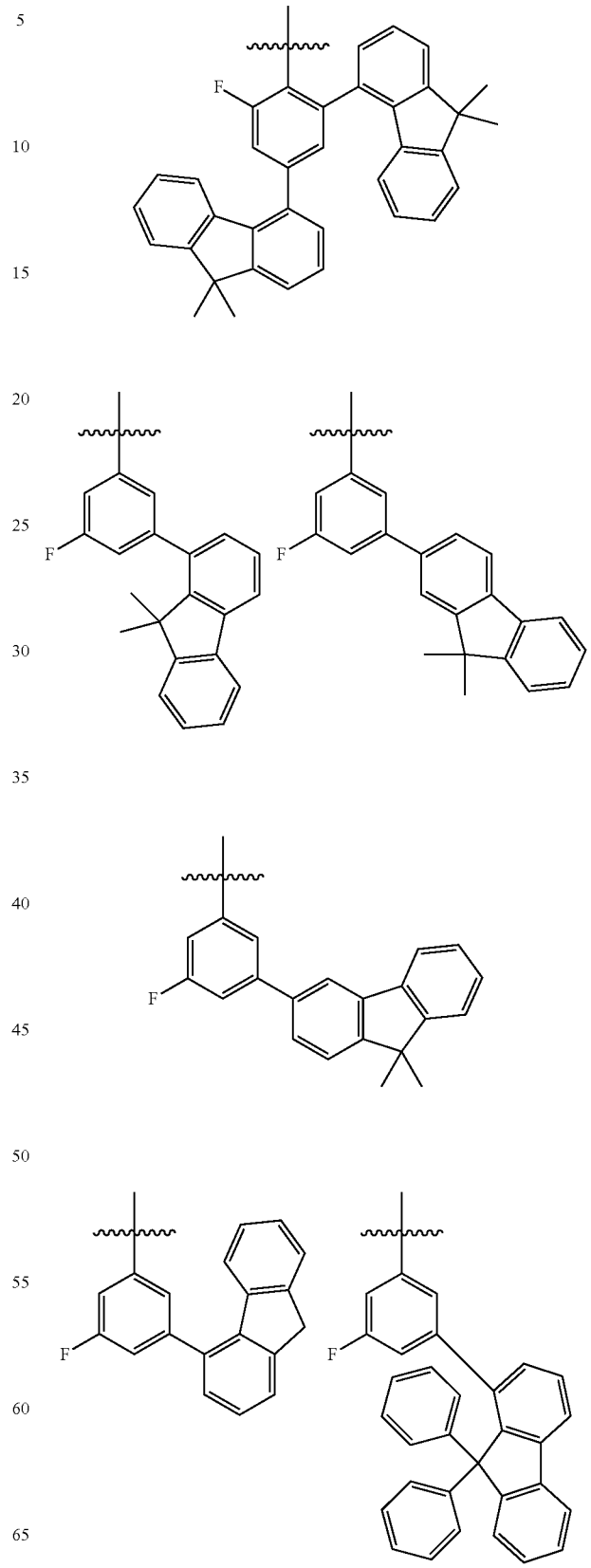

181
-continued
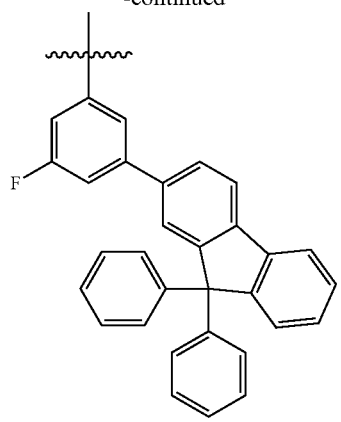
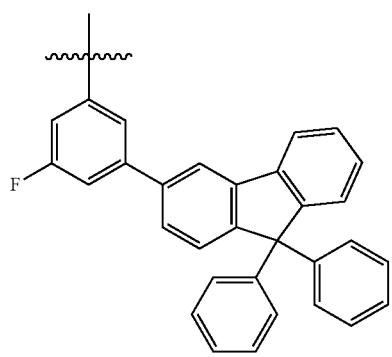
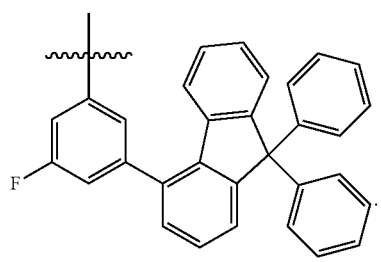
12. The pyrene-based compounds of claim 1, wherein the pyrene-based compound is one of Compounds 1 to 9 below:
1
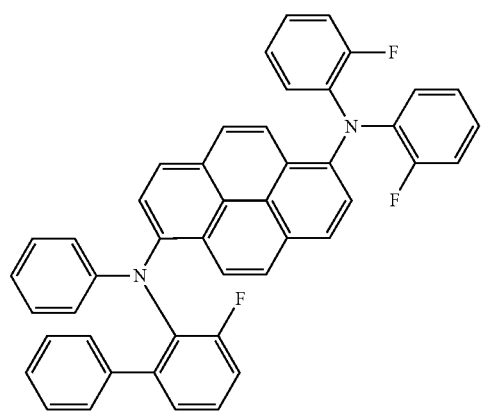
182
-continued
2
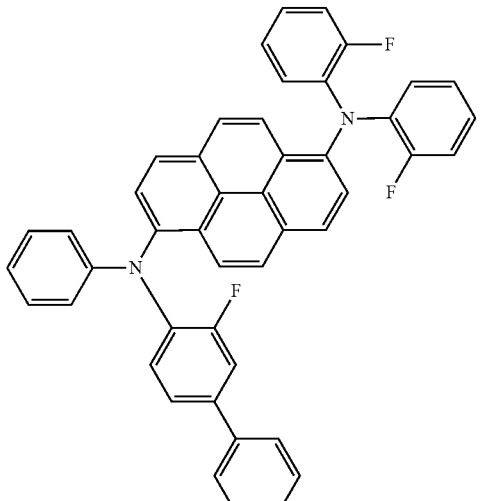
3
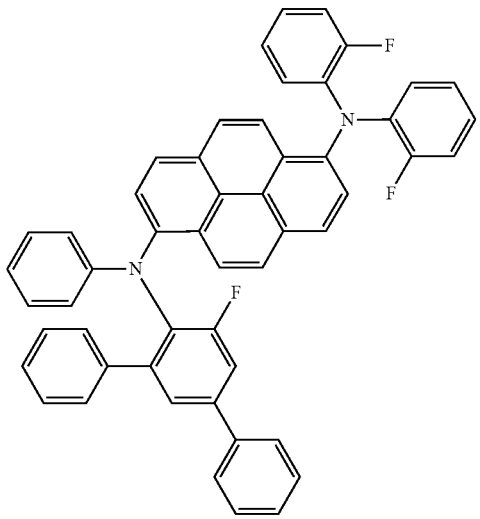
4
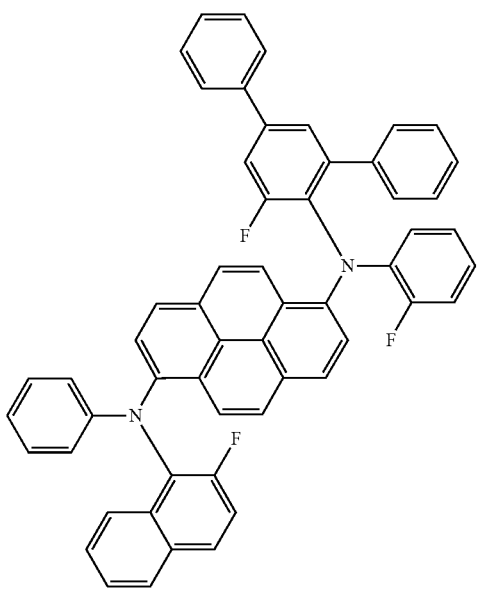

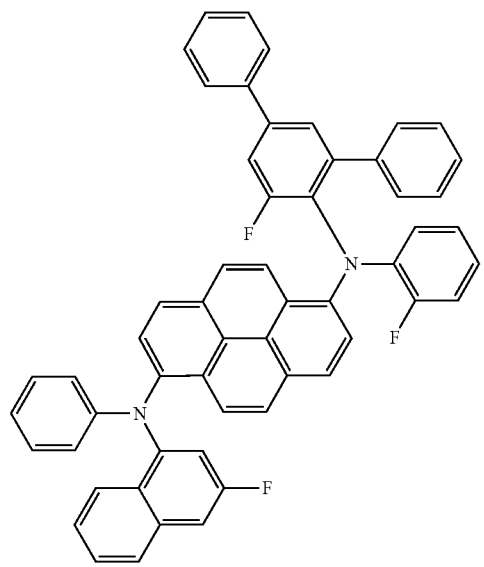
5
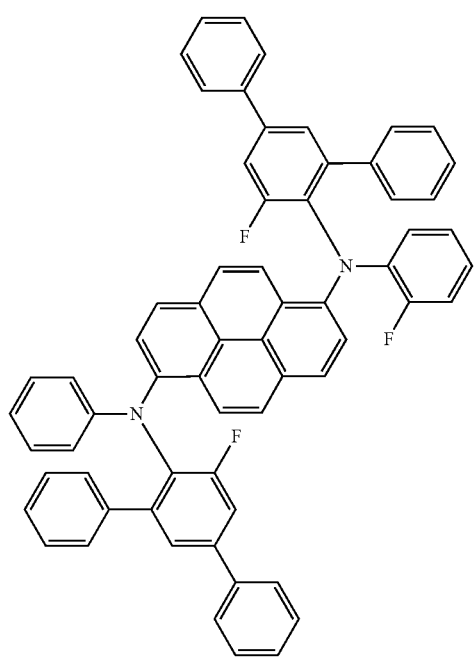
6
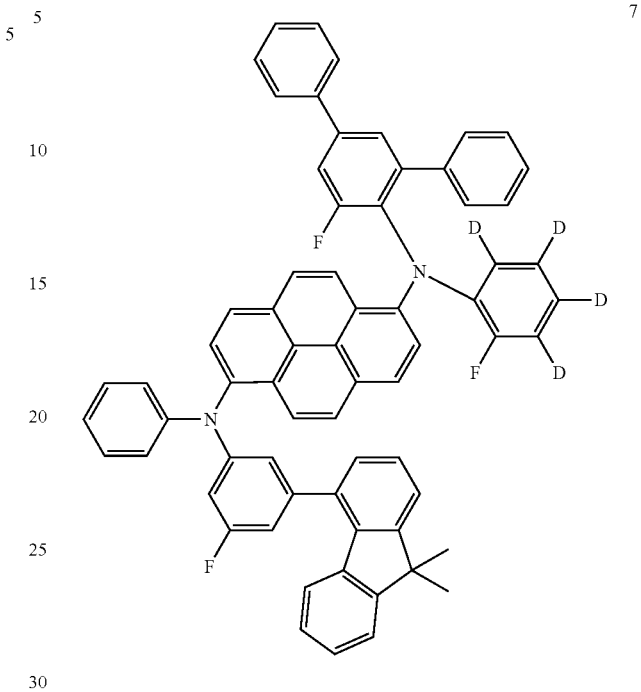
7
8

-continued

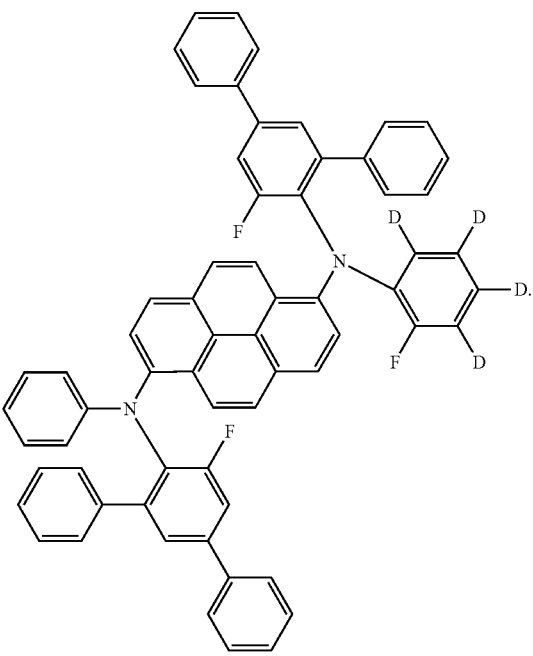

9

13. An organic light-emitting diode comprising: a first electrode; a second electrode disposed opposite to the first electrode; and an organic layer disposed between the first electrode and the second electrode and comprising an emission layer, the organic layer comprising at least one pyrene-based compound of claim 1.

14. The organic light-emitting diode of claim 13, wherein the organic layer further comprises at least one of a hole injection layer, a hole transport layer, a functional layer having both hole injection and hole transport capabilities, a buffer layer, or an electron blocking layer between the first electrode and the emission layer, and further comprises at least one of a hole blocking layer, an electron transport layer, or a functional layer having both electron injection and electron transport capabilities between the emission layer and the second electrode.

15. The organic light-emitting diode of claim 13, wherein the pyrene-based compound is in the emission layer, and the emission layer further comprises a host.

16. The organic light-emitting diode of claim 15, wherein the host comprises at least one anthracene-based compound represented by Formula 400 below, or an anthracene-based compound represented by Formula 401 below:

<Formula 400>

$$Ar_{114}\!-\!(Ar_{112})_h\!-\!\overset{(Ar_{115})_i}{\underset{(Ar_{116})_j}{\text{anthracene}}}\!-\!(Ar_{111})_g\!-\!Ar_{113}$$

<Formula 401>

(structure with $Ar_{122}$, $Ar_{123}$, $Ar_{126}$, $Ar_{127}$, $(Ar_{124})_l$, $(Ar_{125})_k$)

wherein, in Formulae 400 and 401, $Ar_{111}$ and $Ar_{112}$ are each independently a substituted or unsubstituted $C_6$-$C_{60}$ arylene group;

$Ar_{113}$ to $Ar_{116}$, and $Ar_{122}$ to $Ar_{125}$ are each independently a substituted or unsubstituted $C_1$-$C_{10}$ alkyl group or a substituted or unsubstituted $C_6$-$C_{60}$ aryl group;

$Ar_{126}$ and $Ar_{127}$ are each independently a $C_1$-$C_{10}$ alkyl group; and g, h, i, j, k, and l are each independently an integer from 0 to 4.

* * * * *